US010738310B2

(12) United States Patent
D'Andrea et al.

(10) Patent No.: US 10,738,310 B2
(45) Date of Patent: Aug. 11, 2020

(54) TREATING CANCER DEFICIENT IN FANCA, FANCD2, FANCE, OR FANCG WITH AN ATM INHIBITOR

(71) Applicants: Dana-Farber Cancer Institute, Inc., Boston, MA (US); Oregon Health Sciences University, Portland, OR (US); The DNA Repair Company, Boston, MA (US)

(72) Inventors: Alan D'Andrea, Winchester, MA (US); David T. Weaver, Newton, MA (US); Markus Grompe, Portland, OR (US); Richard Kennedy, Belfast (IE)

(73) Assignee: Dana-Faber Cancer Institute, Inc., Boston, MA (US)

(*) Notice: Subject to any disclaimer, the term of this patent is extended or adjusted under 35 U.S.C. 154(b) by 55 days.

(21) Appl. No.: 14/948,914

(22) Filed: Nov. 23, 2015

(65) Prior Publication Data

US 2016/0152985 A1 Jun. 2, 2016

Related U.S. Application Data

(63) Continuation of application No. 11/975,997, filed on Oct. 22, 2007, now abandoned.

(60) Provisional application No. 60/853,208, filed on Oct. 20, 2006, provisional application No. 60/895,606, filed on Mar. 19, 2007.

(51) Int. Cl.
| | |
|---|---|
| *A61K 6/00* | (2020.01) |
| *C12N 15/113* | (2010.01) |
| *C12Q 1/6886* | (2018.01) |
| *A61K 31/713* | (2006.01) |
| *A61K 45/06* | (2006.01) |
| *G01N 33/574* | (2006.01) |

(52) U.S. Cl.
CPC ........ *C12N 15/1137* (2013.01); *A61K 31/713* (2013.01); *A61K 45/06* (2013.01); *C12Q 1/6886* (2013.01); *G01N 33/57496* (2013.01); *C12N 2310/14* (2013.01); *C12N 2320/30* (2013.01); *C12N 2320/31* (2013.01); *C12Q 2600/106* (2013.01); *C12Q 2600/136* (2013.01); *C12Q 2600/158* (2013.01); *G01N 2333/4716* (2013.01)

(58) Field of Classification Search
CPC .............................. C12N 15/1137; A61K 6/00
USPC ...................................................... 435/6, 6.1
See application file for complete search history.

(56) References Cited

U.S. PATENT DOCUMENTS 8,227,434 B1 7/2012 Dalton et al.

FOREIGN PATENT DOCUMENTS

| WO | WO 2003/039327 A2 | 5/2003 |
|---|---|---|
| WO | WO 2005/012524 A1 | 2/2005 |
| WO | WO 2005/053662 A1 | 6/2005 |
| WO | WO 2006/127978 A2 | 11/2006 |
| WO | WO 2008/066624 | 6/2008 |

OTHER PUBLICATIONS

Kang et al (Mol Cell Biol, 2005, 25(2): 661-670).*
Collis et al (Cancer Research, 2003, 63: 1550-1554).*
Collis et al (World J Urol, 2003, 21: 275-289).*
Jian et al (Int J Gynecol Cancer, 2006, 16: 1620-1603).*
Yan et al (Mol Cancer Ther, 2004, 3(9): 1147-1157).*
Huber et al (DNA Repair, 2004, 1103-1108).*
Abderkader, M. E., et al., Journal of Clinical Oncology, vol. 25, No. 18S, 6081.
Bakkenist et al., *Nature*, 421(6922):499-506 (2003).
Bernstein et al., *Mutation Res.*, 511:145-178 (2002).
Boeckman et al., Mol Cancer Res, 2005, 3: 277-285.
Boehle et al., Langenbeck's Arch Surg, 2002, 387: 234-239.
Brody L.C., *N. Eng. J. Med.*, 353:949-950 (2005).
Bryant et al., *Nature*, 434 (7035):913-917 (2005).
Bryant et al., *Nucl. Acids Res.*, 34(6):1685-1691 (2006).
Carmichael, Br J Cancer, 1998, 78 Suppl 3:21-25.
Chen et al., Cancer Research, 2007, 67:9077-9083.
Chin, D. et al., International Journal of Cancer, vol. 113, No. 5, pp. 789-797, 2005.
Chin D. et al., British Journal of Plastic Surgery, vol. 57, No. 7, pp. 595-602, Oct. 1, 2004.
Chirnomas D. et al., Mol Cancer Ther. Apr. 2006 5(4):952-61.
Collis et al., *Oncogene*, 24(6):949-961 (2005).
Currie et al., Cancer Chemother Pharmacal, 1990, 25(5): Abstract.
Curtin et al., *Clin. Cancer Res.*, 10:881-889 (2004).
Dermer, Bio/Technology, 1994, 12:320.
Farley et al., *J. Surg. Res.*, 133(1):29-37 (2006).
Farmer et al., *Nature*, 434(7035):917-921 (2005).
Ferrer et al., Clinical Lung Cancer, 2005, 6(4): 250-254.
Frederico, M.H. et al., Journal of Clinical Oncology, vol. 25, No. 18S, 21127, 2007.
Freshney, Culture of Animal Cells, A Manual of Basic Technique, Alan R. Liss, Inc., 1983, New York, p. 4.
Gallmeier et al., *Cancer Res.*, 67(5):2169-2177 (2007).
Garcia-Higuera et al., *Mol. Cell*, 7(2):249-262 (2001).
Garcia-Higuera et al., *Blood*, 96(9):3224-3230 (2000).
Gura, Science, 1997, 278:1041-1042.
Hegi et al., *Clin. Cancer Res.*, 10:1871-1874 (2004).
Heiger-Bernays, Biochemistry, 1990, 29(36): Abstract.
Hickson et al., *Cancer Res.*, 64:9152-9159 (2004).
Ho et al., *Mol. Cell. Biol.*, 26(18):7005-7015 (2006).
Hu et al., *J. Biol. Chem.*, 279(38):39736-39744 (2004).
Kennedy et al., *J. Clin. Invest.*, 117(5):1440-1449 (2007).
Liu et al., *Curr. Opin. Investig. Drugs*, 5(6):623-627 (2004).

(Continued)

*Primary Examiner* — Sean E Aeder
(74) *Attorney, Agent, or Firm* — Fish & Richardson P.C.

(57) ABSTRACT

This present invention compositions and methods of treating cancer and methods of accessing/monitoring the responsiveness of a cancer cell to a therapeutic compound.

13 Claims, 53 Drawing Sheets

Specification includes a Sequence Listing.

(56) References Cited

OTHER PUBLICATIONS

Madhusudan et al., *Cancer Treat. Rev.*, 31:603-617 (2005).
Madhusudan et al., *Nucleic Acids Res.*, 33(15):4711-4724 (2005).
McCabe et al., *Cancer Res.*, 66(16):8109-8115 (2006).
Mudhusudan S. et al., Clinical Cancer Research 10: 2986 (2004).
Mudhusudan S. and Ganesa T.S., Clin. Biochem 37: 618 (2004).
Mudhusudan S. et al., Clinical Cancer Research 10: 6528 (2004).
Narayan et al., Cancer Research, 2004, 64: 2994-2997.
Nemunaitis J. J. et al., Journal of Clinical Oncology, vol. 25, No. 18S, 2007.
Ohnishi et al., Radiat Res, 2006, 166(3): 454-462.
Parsels et al., Mol Cancer Ther, 2009, 8(1): 45-54.
Paz et al., *Clin. Cancer Res.*, 10:4933-4938 (2004).
Ratnam et al., *Clin. Cancer Res.*, 13(5):1383-1388 (2007).
Riballo et al., Mol. Cell 16:715 (2004).
Roberg, K. B. et al., Journal of Clinical Oncology, vol. 25, No. 18S, 6082, 2007.
Schafer et al., PLoS One, 2010, 5(11):e14060.
Scharer et al., *Bioessays*, 23(3):270-281 (2001).
Seiwert, T.Y. et al., Journal of Clinical Oncology, vol. 26, No. 15S, 6003, 2008.
Seiwert, T.Y. et al., Journal of Clinical Oncology, vol. 25, No. 18S, 6021, 2007.
Sobeck et al., *Mol. Cell Biol.*, 26(2):425-437 (2006).
Spankuch-Schmitt et al., J Natl Cancer Inst, 2002, 94(24): 1863-1877.
Stubbert et al., BMC Cancer, 2010, 10:207, 6-10.
Sugimori et al., Gynecol Oncol, 1989, 34(2): Abstract.
Taniguchi et al., *Cell*, 109(4):459-472 (2002).
Taniguchi et al., Nat Med, 2003, 9: 568-574.
Teicher et al., Cancer Research, 1986, 46(9): 4379-4383.
Turner et al., *Curr. Opin. Pharmacol.*, 5:388-393 (2005).
Van de Heijden et al. Clinical Cancer Research, 2005, 11(20): 7508-7515.
Wang et al., *Mol.Cell. Biol.*, 27(8):3098-3108 (2007).
Xiao et al., Int J Cancer, 2005, 115: 528-535.

\* cited by examiner

APPLICATION OF PRESENT DNAR MARKERS IN DECISION
FOR CHEMOTHERAPEUTIC AGENTS IN BREAST CANCER

| POSSIBLE CANCER INDICATIONS | STAGE OF MANAGEMENT | POSSIBLE SPECIMEN | EXAMPLES OF POSSIBLE RESULTS FROM DNAR'S MARKERS (ACTIVE (+) OR INACTIVE (-) DNA REPAIR PATHWAYS) | | | | | | PREDICTED DRUG ACTIVITY | |
|---|---|---|---|---|---|---|---|---|---|---|
| | | | BER | MMR | NER | HR | NHEJ | TLS | SENSITIVITY | RESISTANCE |
| BREAST | INITIAL EVALUATION, PREOPERATIVE CT, POSTOPERATIVE CT, CT IN METASTASIS AND RECURRENCE | BIOPSY | | | | + | | + | CISPLATIN | MITO C, BLEOMYCIN, ETOPSIDE |
| | | | | | | + | | - | | CISPLATIN |
| | | | | | | - | | + | CISPLATIN, MITO C, BLEOMYCIN, ETOPSIDE | |
| | | | | | | - | | - | MITO C, BLEOMYCIN, ETOPSIDE | CISPLATIN |

ASSUMPTIONS:
1. PRESENT SINGLE MARKER FOR EACH OF THE TWO PATHWAYS, HR AND TLS, IS SUFFICIENT TO ACCURATELY ASSESS PATHWAY ACTIVITY AND, THEREFORE, SENSITIVITY/RESISTANCE OF CANCER TO CHEMOTHERAPEUTIC AGENT.
2. UP REGULATION OF OTHER PATHWAYS DOES NOT COMPENSATE FOR LOW ACTIVITY OR LACK OF ACTIVITY OF HR AND TLS PATHWAYS.

Fig. 16

APPLICATION OF PRESENT DNAR MARKERS IN
DECISIONS FOR CHEMOTHERAPEUTIC AGENTS

| POSSIBLE THERAPEUTIC AGENTS | POSSIBLE CANCERS AFFECTED | POSSIBLE SPECIMEN | EXAMPLES OF POSSIBLE RESULTS FROM DNAR'S MARKERS (ACTIVE (+) OR INACTIVE (-) DNA REPAIR PATHWAYS) | | | | | | PREDICTED DRUG ACTIVITY | |
|---|---|---|---|---|---|---|---|---|---|---|
| | | | BER | MMR | NER | HR | NHEJ | TLS | SENSITIVITY | RESISTANCE |
| CISPLATIN, MITO C, BLEOMYCIN, ETOPOSIDE | BREAST PROSTATE LUNG (NSC) LUNG (SC) ENDOMETRIAL GASTRIC OVARIAN HODGKIN'S L. MELANOMA PANCREAS | BIOPSY, ASCITES, CIRCULATING TUMOR CELLS | | | | + | | + | CISPLATIN | MITO C, BLEOMYCIN, ETOPSIDE |
| | | | | | | + | | - | | CISPLATIN |
| | | | | | | - | | + | CISPLATIN, MITO C, BLEOMYCIN, ETOPSIDE | |
| | | | | | | - | | - | MITO C, BLEOMYCIN, ETOPSIDE | CISPLATIN |

ASSUMPTIONS:
1. PRESENT SINGLE MARKER FOR EACH OF THE TWO PATHWAYS, HR AND TLS, IS SUFFICIENT TO ACCURATELY ASSESS PATHWAY ACTIVITY AND, THEREFORE, SENSITIVITY/RESISTANCE OF CANCER TO CHEMOTHERAPEUTIC AGENT.
2. UP REGULATION OF OTHER PATHWAYS DOES NOT COMPENSATE FOR LOW ACTIVITY OR LACK OF ACTIVITY OF HR AND TLS PATHWAYS.

Fig. 17

**APPLICATION OF MARKERS FOR THE SIX DNA REPAIR PATHWAYS
IN DECISION FOR CHEMOTHERAPEUTIC AGENTS: BREAST CANCER**

| POSSIBLE CANCER INDICATIONS | STAGE OF MANAGEMENT | POSSIBLE SPECIMEN | EXAMPLES OF POSSIBLE RESULTS FROM DNAR'S MARKERS (ACTIVE (+) OR INACTIVE (-) DNA REPAIR PATHWAYS) | | | | | | PREDICTED DRUG ACTIVITY | |
|---|---|---|---|---|---|---|---|---|---|---|
| | | | BER | MMR | NER | HR | NHEJ | TLS | SENSITIVITY | RESISTANCE |
| BREAST | INITIAL EVALUATION, PREOPERATIVE CT, POSTOPERATIVE CT, CT IN METASTASIS AND RECURRENCE | BIOPSY, CIRCULATING TUMOR CELLS | + | + | + | + | + | + | CISPLATIN | |
| | | | + | − | + | + | + | + | CISPLATIN (?) | MITO C |
| | | | + | − | + | + | + | − | | MITO C, CISPLATIN |
| | | | + | + | − | + | + | + | CISPLATIN | |
| | | | + | + | + | − | + | + | BLEOMYCIN, MITO C | |
| | | | + | + | + | + | − | + | BLEOMYCIN, ETOPSIDE | |

ASSUMPTIONS:
1. DNAR WILL DISCOVER/ACQUIRE ALL OF THE NECESSARY MARKERS FOR ACCURATE ASSESSMENT OF THE SIX DNA REPAIR PATHWAYS.
2. DNAR WILL DEVELOP A DATABASE, FROM ASSESSMENT OF CLINICAL MATERIAL, THAT PROVIDES ASSOCIATIONS BETWEEN ACTIVITY/INACTIVITY OF DNA REPAIR PATHWAYS AND SENSITIVITY OR RESISTANCE TO CHEMOTHERAPEUTIC AGENTS.
3. THE DATABASE WILL PROVIDE *PROBABILITIES* OF SENSITIVITY OR RESISTANCE TO CHEMOTHERAPEUTIC AGENTS BASED ON THE *PATTERN* OF ACTIVITY OF DNA REPAIR PATHWAYS.

Fig. 18

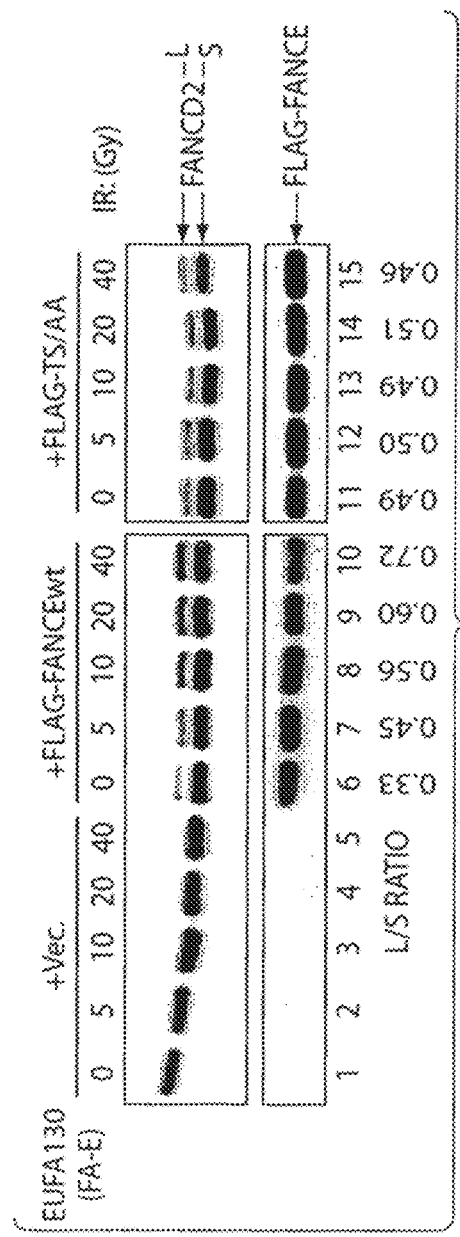
Fig. 19C
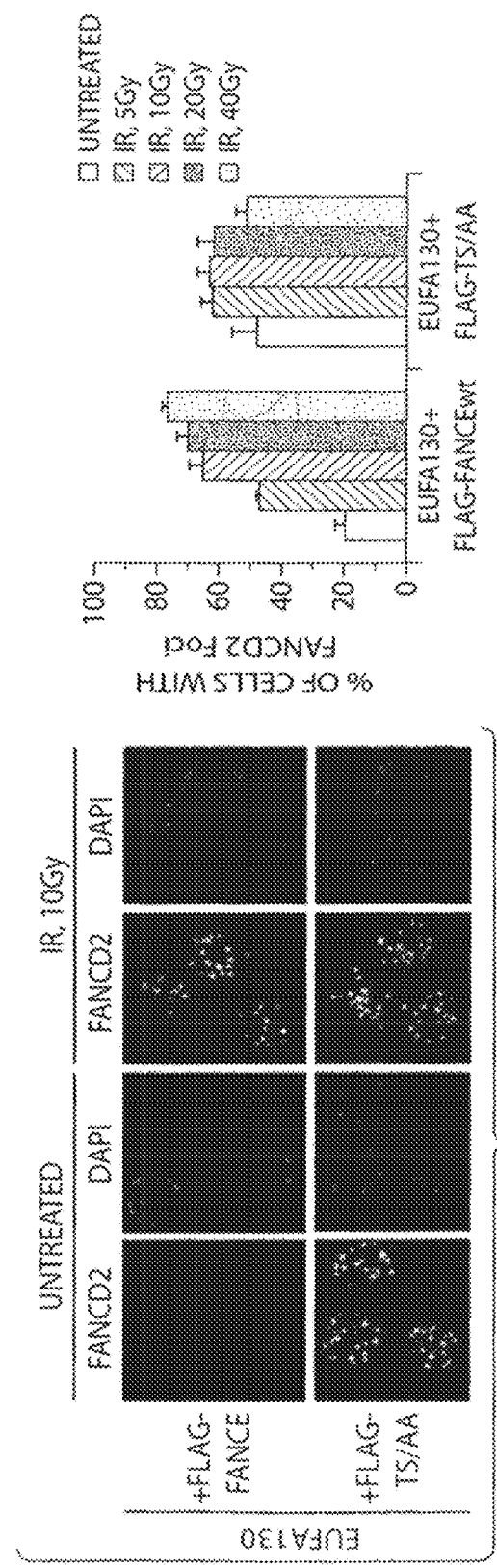
Fig. 19E
Fig. 19D

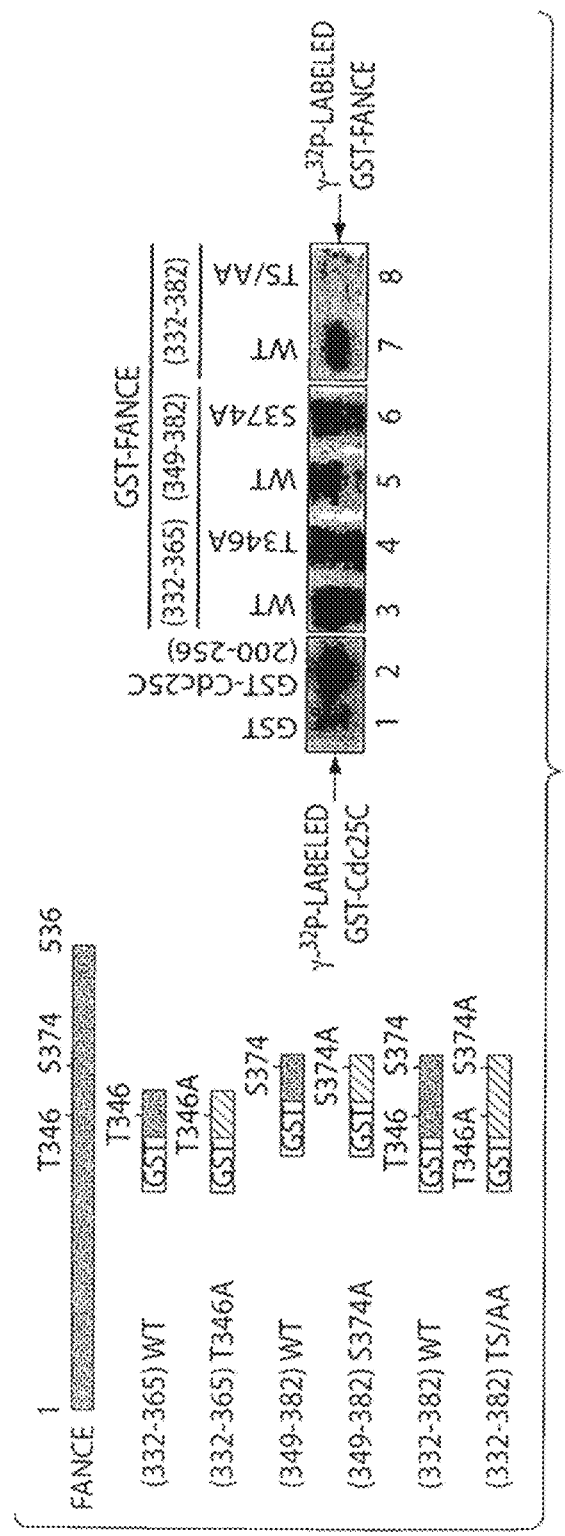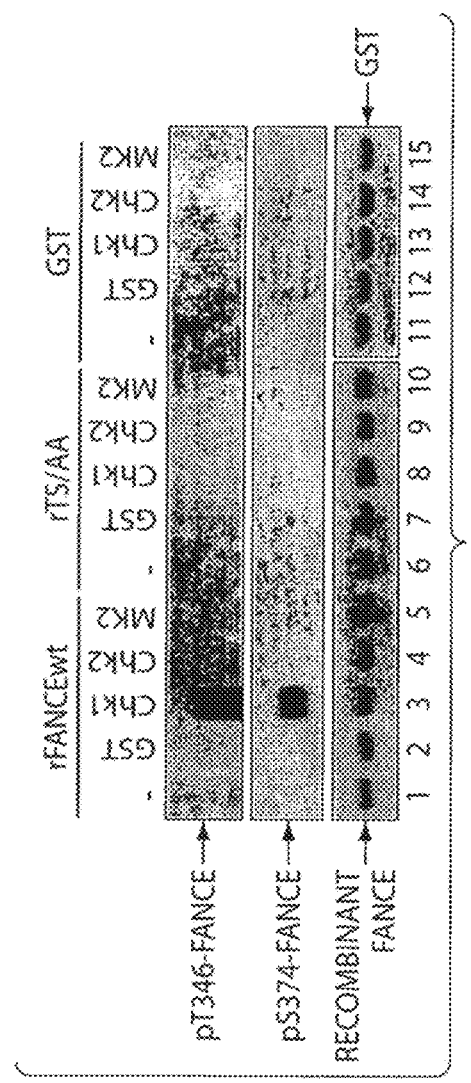
Fig. 20A
Fig. 20B

FANCE MUTATION IN DF1179 (FA-E) CELLS

| FANCE MUTATION | NUCLEOTIDE CHANGE | CONSEQUENCE | AA CHANGE | EXON/INTRON | DOMAIN | TYPE |
|---|---|---|---|---|---|---|
| c.1111 C>T | CGG-to-TGG | Arg-to-Trp | R371W | Exon 5 | C-TERMINAL | MISSENSE MUTATION |

FA PATHWAY DISRUPTED IN EXAMPLE SPORADIC TUMORS:
1) OVARIAN CANCER: BRCA2/FANCD1 (MUTATED/METHYLATED), FANCF (METHYLATED), FANCD2 (?TRANSCRIPTIONAL).
2) BREAST CANCER: BRCA2 (MUTATED/METHYLATED).
3) PANCREATIC CANCER: FANCC FANCG BRCA2 (MUTATED).
4) HEAD AND NECK CANCER: FANCF (METHYLATED).
5) TESTICULAR GERM CELL TUMORS: FANCF (METHYLATED).
6) CERVICAL CANCER: FANCF (METHYLATED).
7) NON-SMALL CELL LUNG CANCER: FANCF (METHYLATED).
8) AML: FANCA, FANCC, FANCF, FANCG (METHYLATED).

Fig. 32

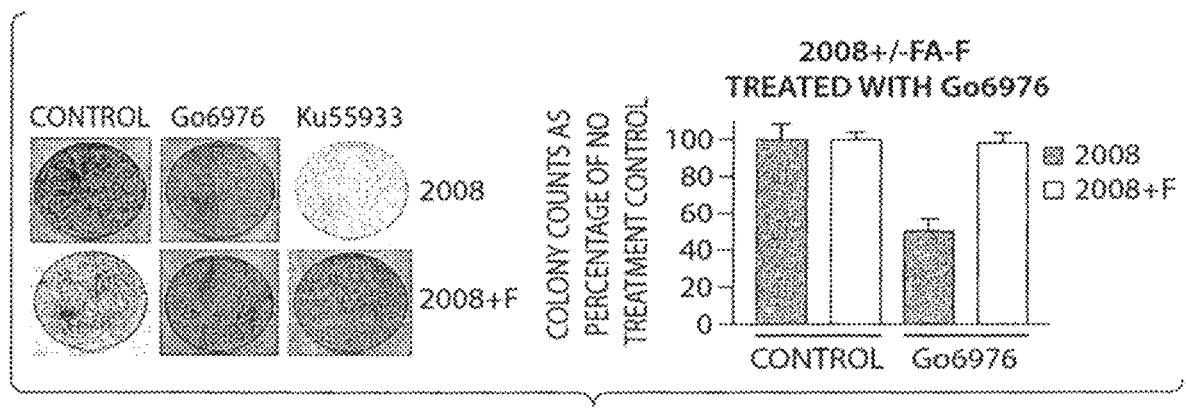

Fig. 33

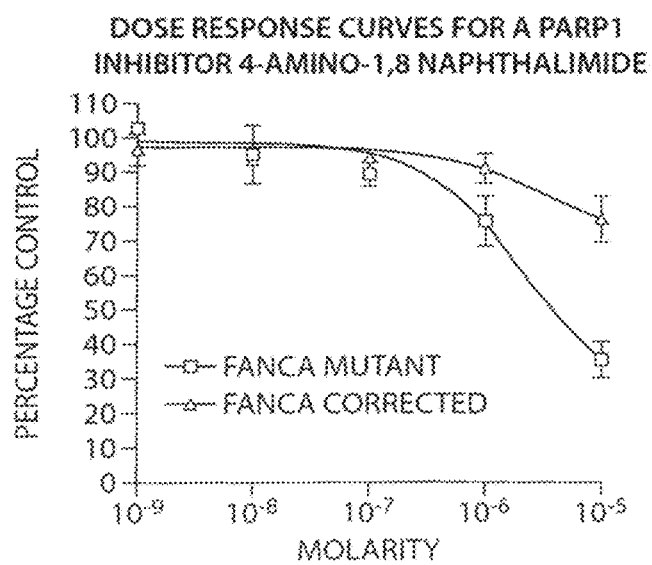

Fig. 34

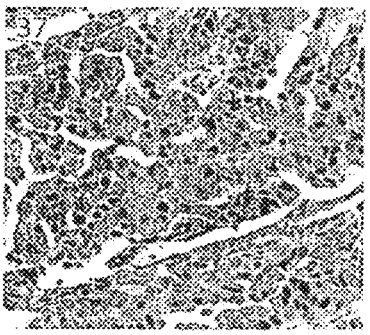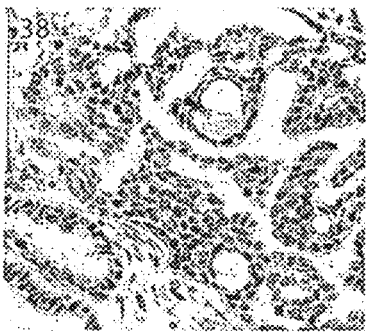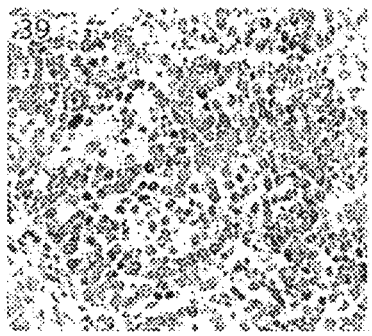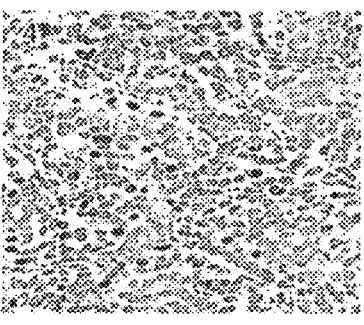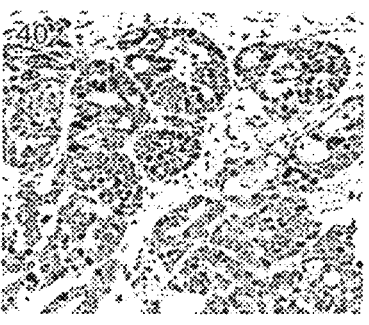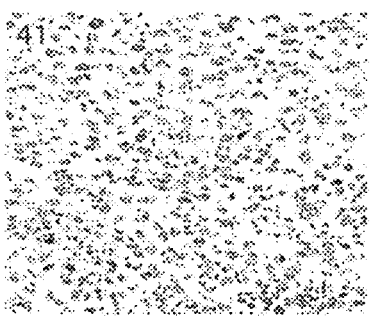
Fig. 41A
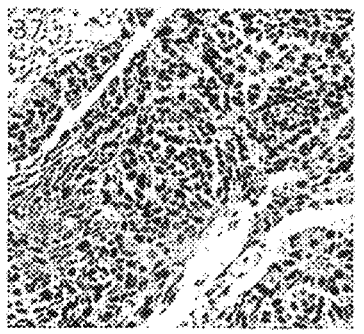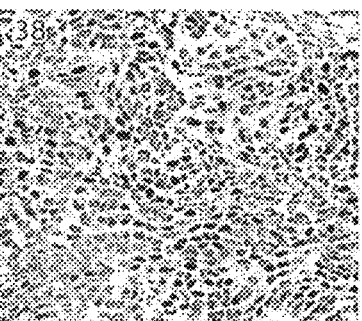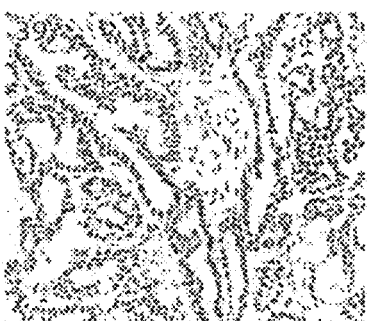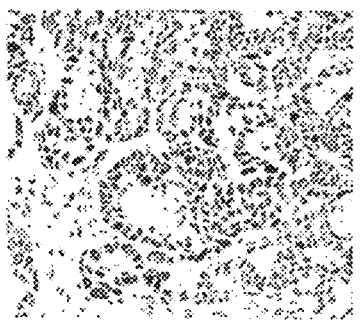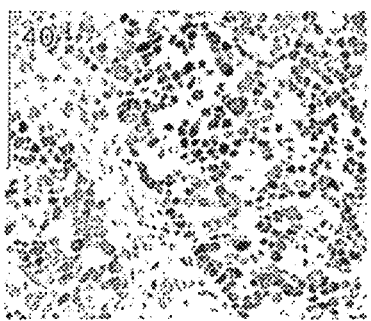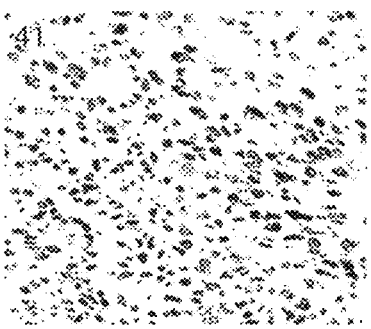
Fig. 41B

TREATING CANCER DEFICIENT IN FANCA, FANCD2, FANCE, OR FANCG WITH AN ATM INHIBITOR

RELATED APPLICATIONS

This application is a continuation of U.S. patent application Ser. No. 11/975,997, filed Oct. 22, 2007, which claims priority to U.S. Provisional Application No. 60/853,208, filed Oct. 20, 2006 and to U.S. Provisional Application No. 60/895,606, filed Mar. 19, 2007, the contents of each of which are incorporated by reference in their entireties.

STATEMENT AS TO FEDERALLY SPONSORED RESEARCH

This invention was made with government support under grant numbers RO1HL052725, RO1DK043889, PO1HL054785, and CA009361 awarded by The National Institutes of Health. The government has certain rights in the invention.

INCORPORATION-BY-REFERENCE OF SEQUENCE LISTING

The contents of the file named "DFCI-070C01US_ST25.txt", which was created on Nov. 23, 2015 and is 6 KB in size, are hereby incorporated by reference in their entirety.

FIELD OF THE INVENTION

This invention relates generally to methods of methods of treating cancer. More specifically, the invention relates to methods of accessing the responsiveness of a cancer cell to a therapeutic compound.

BACKGROUND OF THE INVENTION

DNA repair refers to a collection of processes by which a cell identifies and corrects damage to the DNA molecules that encode its genome. In human cells, both normal metabolic activities and environmental factors such as UV light can cause DNA damage, resulting in as many as 1 million individual molecular lesions per cell per day. Many of these lesions cause structural damage to the DNA molecule and can alter or eliminate the cell's ability to transcribe the gene that the affected DNA encodes. Other lesions induce potentially harmful mutations in the cell's genome, which will affect the survival of its daughter cells after it undergoes mitosis. Consequently, the DNA repair process must be constantly active so it can respond rapidly to any damage in the DNA structure.

The rate of DNA repair is dependent on many factors, including the cell type, the age of the cell, and the extracellular environment. A cell that has accumulated a large amount of DNA damage, or one that no longer effectively repairs damage incurred by its DNA, can enter one of three possible states: an irreversible state of dormancy, known as senescence; cell suicide, also known as apoptosis or programmed cell death or unregulated cell division, which can lead to the formation of a tumor.

SUMMARY OF THE INVENTION

The present invention is based on the discovery that tumor cells have altered DNA repair and DNA damage response pathways and that loss of one of these pathways renders the cancer more sensitive to a particular class of DNA damaging agents. More particularly, the invention is based in part upon the discovery that a defect in two DNA repair pathways in a cell is lethal.

The present invention provides methods of treating cancer in a subject. In one embodiment, the method of treating cancer includes (a) determining whether the cancer cell is deficient in a DNA repair pathway and (b) administering a DNA damaging agent or inhibitor specific for at least one different DNA repair pathway than that identified in step (a) to the subject. In another embodiment, the method of treating cancer in a subject includes (a) determining whether the cancer cell is deficient in a DNA repair pathway, (b) identifying a DNA repair pathway protein or gene that is upregulated in the cancer cell and (c) administering a DNA damaging agent or inhibitor specific for the DNA repair pathway protein or gene identified in step (b) to the subject.

The present invention also provides methods for selecting a therapeutic agent for a particular cancer cell including (a) determining a deficiency in one or more DNA repair pathways in the cancer cell relative to a normal cell and (b) selecting a DNA damaging agent or inhibitor specific for at least one DNA repair pathway other than the DNA pathway identified in step (a).

The present invention also provides methods of determining the resistance or sensitivity of a cancer cell to a chemotherapeutic agent. In one embodiment, the method of determining the resistance of a cancer cell to a chemotherapeutic agent includes identifying a deficiency in a DNA repair pathway, where the presence of the deficiency indicates the cell is resistant to a chemotherapeutic agent specific for the DNA repair pathway. In another embodiment, the method of determining the sensitivity of a cancer cell to a chemotherapeutic agent includes identifying a deficiency in a DNA repair pathway, where the absence of the deficiency indicates the cell is sensitive to a chemotherapeutic agent specific for the DNA repair pathway.

The present invention also provides methods of identifying and modulating the responsiveness of a cancer cell to treatment. In one embodiment, the method of identifying the responsiveness of a cancer cell to a DNA crosslinking agent or ionizing radiation includes identifying a deficiency in the homologous recombination and crosslinking repair (FA/HR) DNA repair pathway, where the presence of the deficiency indicates the cell is sensitive to DNA cross linking agent or ionizing radiation, whereas an absence if the efficiency indicates the cell is resistant to DNA crosslinking agent or ionizing radiation. In another embodiment, a method of increasing the responsiveness of a cancer cell to a DNA crosslinking agent or ionizing radiation includes contacting the cancer cell with an inhibitor of the homologous recombination and crosslinking repair (FA/HR) DNA repair pathway. In another embodiment, the method of identifying the responsiveness of a cancer cell to a MAP2KAP2 inhibitor includes detecting phosphorylation of MAP2KAP2, where the presence of the phosphorylation indicates the cell is sensitive to a MAP2KAP2 inhibitor, whereas an absence of the phosphorylation indicates the cell is resistant to a MAP2KAP2 inhibitor. In another embodiment, the method of identifying the responsiveness of a cancer cell to a FA/HR DNA repair pathway inhibitor includes identifying a deficiency in the mismatch repair (MMR) DNA repair pathway, where the presence of the deficiency indicates the cell is sensitive to a FA/HR DNA repair pathway inhibitor whereas an absence if the efficiency indicates the cell is resistant to a FA/HR DNA repair pathway inhibitor.

The present invention also provides methods of assessing the effectiveness or monitoring the treatment of a subject with cancer. In one embodiment, the method of accessing the effectiveness of a treatment of a subject with cancer includes (a) measuring the level of an effective amount of two or more DNARMARKERS selected from DNARMARKERS 1-259 in a sample from the subject, and (b) comparing the level of the effective amount of the two or more DNARMARKERS to a reference value. In another embodiment, the method of monitoring the treatment of a subject with cancer includes (a) detecting the level of an effective amount of two or more DNARMARKERS from DNARMARKERS 1-259 in a first sample from the subject at a first period of time, (b) detecting the level of an effective amount of two or more DNARMARKERS in a second sample from the subject at a second period of time, and (c) comparing the level of the effective amount of the two or more DNARMARKERS detected in step (a) to the amount detected in step (b), or to a reference value. In another embodiment, the method of monitoring the treatment of a subject with cancer includes (a) determining whether the cancer cell is deficient in a DNA repair pathway at a first period of time, (b) determining whether the cancer cell is deficient in the DNA repair pathway identified in step (a) at a second period of time; where a decrease in the deficiency in the DNA repair pathway indicates the treatment is not efficacious, whereas a increase or no change in the DNA repair pathway indicates the treatment is efficacious The present invention also provides a panel with at least two proteins from two or more DNA repair pathways including base excision repair (BER), homologous recombination and crosslinking repair (FA/HR), mismatch repair (MMR), non-homologous endjoining repair (NHEJ), nucleotide excision repair (NER), translesion DNA synthesis (TLS), and DNA damage responsiveness (DDR). In one embodiment, the panel includes at least one Fanconi Anemia protein and at least one Mismatch Repair protein. In another embodiment, the panel includes one or more DNARMARKERS that are indicative of a pathway associated to DNA repair or DNA damage recognition and regulatory proteins.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the invention will be apparent from the following detailed description and claims.

BRIEF DESCRIPTION OF THE DRAWINGS

FIG. 16 is a schematic graphical representation of the use of DNARMARKERS in assessing the use of chemotherapeutic agents in breast cancer treatment regimens.

FIG. 17 is a schematic graphical representation of the use of DNARMARKERS in assessing the use of chemotherapeutic agents in various cancer treatment regimens.

FIG. 18 is a schematic graphical representation of the use of DNARMARKERS and the functionality of the six DNA repair pathways in assessing the use of chemotherapeutic agents in breast cancer treatment regimens.

FIG. 19 C is a photograph of a Western blot showing restoration of monoubiquitination of FANCD2. The indicated stably transduced FA-E lymphoblast cell lines were either untreated or exposed to ionizing radiation (IR) at different doses, as indicated, and harvested after 6 hours. Western blotting was performed with anti-FANCD2 or anti-FLAG antibodies.

FIG. 19D is a photograph of cell cultures showing restoration of FANCD2 nuclear foci formation. EUFA130 (FA-E) lymphoblasts stably expressing FLAG-FANCEwt (EUFA130+FLAG-FANCE) and the double mutant FLAG-TS/AA (EUFA130+FLAG-TS/AA) were either untreated or treated with IR (10 Gy) and fixed 6 hours later, immunofluorescence was performed using anti-FANCD2 (FI-17) antibody. Magnification, ×630.

FIG. 19E is a bar chart showing quantification of FANCD2 foci. Cells with more than four distinct foci were counted as positive. 200 cells/sample were analyzed. The values shown are the mean±SD from three separate experiments.

FIG. 20A is a schematic showing GST-FANCE peptide fusion proteins, containing the indicated regions of FANCE were generated and used as substrates for in vitro kinase assay, the threonine (346) and/or serine (374) residues that were mutated to alanine are shown (left panel). GST-FANCE peptide fusion proteins were incubated with [γ-$^{32}$P] ATP and purified recombinant Chk1. The reaction was stopped by addition of SDS sample buffer before analysis by SDS-PAGE and autoradiography (right panel). GST-Cdc25C (200-256) peptide fusion protein and GST were used as positive and negative control substrates for Chk1 to demonstrate efficient in vitro kinase assays.

FIG. 20B is a photograph showing In vitro kinase assays using GST, purified recombinant Chk1, Chk2 or MK2 to phosphorylate recombinant FANCE proteins (149-536) of wild-type (rFANCEwt) and the double mutant (rTS/AA) were performed and analyzed by SDS-PAGE, followed by immunoblotting with the phospho-T346-FANCE (pT346-FANCE), phospho-S374-FANCE (pS374-FANCE) antibodies. GST-Cdc25C (200-256) peptide fusion protein and GST were used as positive and negative control substrates for Chk1, Chk2 and MK2 to demonstrate efficient in vitro kinase assays.

FIGS. 26A and 26B. Phospho-T346-FANCE foci formation in response to lower dose of DNA damage. HeLa cells were exposed to lower dose of DNA damage: UV (10 J/m²), IR (2 Gy) or MMC (40 ng/ml) and incubated for different periods of time as indicated before fixation, immunofluorescence was performed using anti-pT346-FANCE antibody. Magnification×400 (FIG. 26A). Cells with more than four distinct pT346-FANCE foci were counted as positive. 200 cells/sample were analyzed. The values shown are the mean±SD from three separate experiments (FIG. 26B). FIGS. 26C and 26D. Effects of Chk1 inhibitors on phospho-T346-FANCE foci formation. HeLa cells were pretreated without or with Chk1 inhibitors Gö6976 and SB218078 (5 μM) for 30 min, and then were exposed to UV at (60 J/m²) and incubated for 3 hr before fixation, immunofluorescence was performed using anti-pT346-FANCE antibody. Magnification, ×400 (FIG. 26C). Cells with more than four distinct pT346-FANCE foci were counted as positive. 200 cells/sample were analyzed. The values shown are the mean±SD from three separate experiments (FIG. 26D).

FIG. 32 is a chart showing examples of disruption of the Fanconi Anemia pathway in spontaneous human tumors (not overtly associated with known BRCA1 or BRCA2-deficiency or with Fanconi Anemia-deficiency.

FIG. 33 is photograph and a bar chart showing that the human ovarian cell line, 2008, is hypersensitive to inhibition by a Chk1 inhibitor or an Atm inhibitor. Cell viability of 2008 and 2008+F cells were examined following treatment with the Chk1 kinase inhibitor, G06976, and the Atm kinase inhibitor, KU55933. Shown are the methylene blue staining of tissue culture plates following 7-10 days growth after incubation with control or the above inhibitors. Quantitation of the cell colony assay for G06976 treatment is shown in the right panel. G06796 causes a significant hypersensitivity of the 2008 ovarian cancer cells, but not the cells restored with the FANCF expression.

FIG. 34 is a bar chart showing FANCA-deficient cells are hypersensitive to a PARP1 inhibitor by comparison with the same cells that have been complemented with the FANCA gene. FANCA Mutant, is a human FANCA-deficient patient cell line. FANCA Corrected, is the same cell where the FANCA gene has been re-introduced by retroviral transduction. Cell survival is measured by clonogenic quantitation.

FIG. 35A (MSH2 (Mismatch Repair), PT2056 DNAPK (NonHomologous Endjoining), FANCDD2 (FA/Homologous Recombination)), FIG. 35B (PS HSP27 (MapKapKinase2 substrate), PT334 MAPKAPKinase2 (DNA damage signaling), MLH1 (Mismatch Repair)), FIG. 35C (MSH6 (Mismatch Repair), PAR (Base Excision Repair), PARP1 (Base Excision Repair), XPF (Nucleotide Excision Repair)). Image analysis was conducted on a group of 9 cancer specimens from the TMA as is illustrated in FIG. 36.

FIG. 37A. A representation of three patient tumor specimens is illustrated with five DNA repair and DNA damage signaling biomarkers from different pathways. Serial sections of the same TMA are IHC stained with each of the five biomarkers. The tumor core images are extracted from the TMA for a higher power view to interpret via image analysis. FIG. 37B. Variation per biomarker for Patient 1, 2, and 3. A colorized output displays the prostate cancer patient variation for these three example specimens.

FIG. 38A. A representation of four patient tumor specimens is illustrated with five DNA repair and DNA damage signaling biomarkers from different pathways. As above with other TMAs, serial sections of the NSCLC TMA are stained with each of the five biomarkers as shown in the figure. The tumor core images are extracted from the TMA for a higher power view to interpret via image analysis. FIG. 38B. Variation per biomarker for Patient 1-4 using a colorization scheme to describe the output.

FIGS. 41A-E. Comparison of six patients with ovarian cancer for IHC staining patterns of DNA repair and DNA damage signaling pathways. IHC staining of the four markers is as shown with FIG. 41A, FANCD2, FIG. 41B, MLH1, FIG. 41C, XPF, FIG. 41D, PT334 MapkapKinase2, and FIG. 41E, Ki67. In each of FIGS. 41A-E, the six head & neck cancer patients are as numbered 37, 38, and 39 (upper panel), and 4, 40, 41 (lower panel).

DETAILED DESCRIPTION OF THE INVENTION

Figure 15:
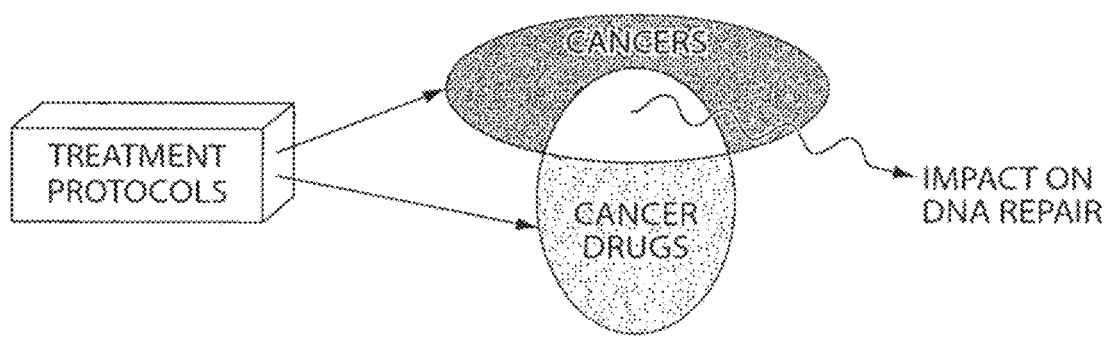
FIG. 15 is a schematic representation showing the impact of DNA repair on cancer treatment methodologies.

The invention relates to the observation that tumor cells have altered DNA repair and DNA damage response pathways and that loss of one of these pathways renders the cancer more sensitive to a particular class of DNA damaging agents. Cancer therapy procedures such as chemotherapy and radiotherapy work by overwhelming the capacity of the cell to repair DNA damage, resulting in cell death. More particularly, the invention is based in part upon the discovery that a defect in two DNA repair pathways in a cell is lethal. Thus, radiation and drug responsiveness of the tumor can be predicted by determining the integrity of the six major DNA repair pathways in a cancer cell (FIG. 15). Status of the DNA repair and DNA damage pathways might drive a treatment decision with one or more chemotherapeutics or radiation for breast cancer (FIG. 16 and FIG. 18). Also shown is an example of how the DNA repair and DNA damage biomarkers may be useful in monitoring specific sensitivity to defined agents and/or resistance to chemotherapy (FIGS. 16-18). Similarly, status of DNA repair and DNA damage pathways can be a means to assess decisions for types of chemotherapeutic agents in a variety of cancers (FIG. 17).

Accordingly, the invention provides methods of determining the responsiveness, e.g., sensitivity or resistance, of a cancer cell to a therapeutic agent by determining which DNA repair pathway is altered. These methods are also useful for monitoring subjects undergoing treatments and therapies for cancer or other cell proliferative disorders, and for selecting therapies and treatments that would be efficacious in subjects having cancer or other cell proliferative disorders, wherein selection and use of such treatments and therapies slow the progression of cancer or other cell proliferative disorders. The present invention further relates to biomarkers which are useful in detecting alterations in a DNA repair pathway.

There are six major DNA repair pathways distinguishable by several criteria which can be divided into three groups those that repair single strand damage and those that repair double stand damage. Single stranded damage repair pathways include Base-Excision Repair (BER); Nucleotide Excision Repair (NER); Mismatch Repair (MMR); Homologous Recombination/Fanconi Anemia pathway (HR/FA); Non-Homologous Endjoining (NHEJ), and Translesion DNA Synthesis repair (TLS).

BER, NER and MMR repair single strand DNA damage. When only one of the two strands of a double helix has a defect, the other strand can be used as a template to guide the correction of the damaged strand. In order to repair damage to one of the two paired molecules of DNA, there exist a number of excision repair mechanisms that remove the damaged nucleotide and replace it with an undamaged nucleotide complementary to that found in the undamaged DNA strand. BER repairs damage due to a single nucleotide caused by oxidation, alkylation, hydrolysis, or deamination. NER repairs damage affecting longer strands of 2-30 bases. This process recognizes bulky, helix-distorting changes such as thymine dimers as well as single-strand breaks (repaired with enzymes such UvrABC endonuclease). A specialized form of NER known as Transcription-Coupled Repair (TCR) deploys high-priority NER repair enzymes to genes that are being actively transcribed. MMR corrects errors of DNA replication and recombination that result in mispaired nucleotides following DNA replication.

NEHJ and HR repair double stranded DNA damage. Double stranded damage is particularly hazardous to dividing cells. The NHEJ pathway operates when the cell has not yet replicated the region of DNA on which the lesion has occurred. The process directly joins the two ends of the broken DNA strands without a template, losing sequence information in the process. Thus, this repair mechanism is necessarily mutagenic. However, if the cell is not dividing and has not replicated its DNA, the NHEJ pathway is the cell's only option. NHEJ relies on chance pairings, or microhomologies, between the single-stranded tails of the two DNA fragments to be joined. There are multiple independent "failsafe" pathways for NHEJ in higher eukaryotes. Recombinational repair requires the presence of an identical or nearly identical sequence to be used as a template for repair of the break. The enzymatic machinery responsible for this repair process is nearly identical to the machinery responsible for chromosomal crossover during meiosis. This pathway allows a damaged chromosome to be repaired using the newly created sister chromatid as a template, i.e. an identical copy that is also linked to the damaged region via the centromere. Double-stranded breaks repaired by this mechanism are usually caused by the replication machinery attempting to synthesize across a single-strand break or unrepaired lesion, both of which result in collapse of the replication fork.

Translesion synthesis Translesion synthesis is an error-prone (almost error-guaranteeing) last-resort method of repairing a DNA lesion that has not been repaired by any other mechanism. The DNA replication machinery cannot continue replicating past a site of DNA damage, so the advancing replication fork will stall on encountering a damaged base. The translesion synthesis pathway is mediated by specific DNA polymerases that insert extra bases at the site of damage and thus allow replication to bypass the damaged base to continue with chromosome duplication. The bases inserted by the translesion synthesis machinery are template-independent, but not arbitrary; for example, one human polymerase inserts adenine bases when synthesizing past a thymine dimmer.

Cancer cells, like normal human cells, can arrest their growth in response to DNA damage. Cell cycle arrest is accomplished, at least in part, by a complex array of intracellular checkpoint kinases. Checkpoint kinases, such as Chk1 (CHEK1), Chk2 (CHEK2), and MapKapKinase2 (MK2, Chk3), once activated, terminate cell growth by arresting the cell cycle in discrete stages, say, at the G1/S, G2/M, or mitotic spindle stage. Cell cycle arrest provides an opportunity to repair DNA damage, before resuming growth.

Cells activate the Chk1 kinase in response to DNA damage. Chk1 phosphorylates multiple protein substrates (effector proteins), which subsequently contribute to the checkpoint response. For instance, Chk1 phosphorylates the protein, Cdc25c, leading to a block in the transition from G2 to M phase of the cell cycle. This checkpoint allows cells (both normal cells and cancer cells) to repair their DNA before entering mitosis (M).

Cancer cells accumulate high levels of DNA damage. This damage may result from their heightened proliferative activity or from exposure to chemotherapy or ionizing radiation. Cancer cells are often hyperdependent on the Chk1-kinase-mediated G2/M cell cycle checkpoint. Increased reliance on Chk1 also results from the tumor cell's loss of another important checkpoint mediator, the p53 protein. Inhibition of Chk1 therefore knocks out a vital checkpoint of tumor cells. Without this checkpoint, tumor cells progress into mitosis, despite the persistence of un-repaired DNA damage, leading to a "mitotic catastrophe" and cell death. Based on this principle, Chk1 inhibitors have been developed. 7-hy-droxy-staurosporine (UCN01) is furthest along with clinical development, as it is in phase II clinical trials. However, UCN01 has a clinical problem because of its prolonged half-life that may manifest in unwanted toxicities. Therefore, identifying the patients that are most appropriately treatable with inhibitors is an important clinical problem. In the case of Chk1 inhibitors broadly, it would be critical to identify the patient responders as a subgroup, so that these patients could be better directed to the therapy that is likely to work. Similarly, patients could also be identified where there would be no apparent benefit to Chk1 inhibitor treatments, and thus these patients may be able to avoid Chk1 inhibitor-associated toxicities. As demonstrated herein, in response to DNA damage, Chk1 directly phosphorylates the FANCE subunit of the FA core complex on two conserved sites (Threonine 346 and Serine 374). Phosphorylated FANCE assembles in nuclear foci and colocalizes with FANCD2. A nonphosphorylated mutant form of FANCE (FANCE-T346A/S374A), when expressed in a FANCE-deficient cell line, allows FANCD2 monoubiquitination, FANCD2 foci assembly, and normal S phase progression. However, the mutant FANCE protein fails to complement the mitomycin C hypersensitivity of the transfected cells. Taken together, these results elucidate a novel role of Chk1 in the regulation of the FA/BRCA pathway and in DNA crosslink repair. Chk1-mediated phosphorylation of FANCE is required for a function independent of FANCD2 monoubiquitination.

DNA Repair and DNA Damage Response Markers

Patients have varying degrees of responsiveness to therapy and methods are needed to distinguish the capability of the treatment in a dynamic manner. Identification of changes (e.g., active, hyperactive, repressed, downmodulated, or inactive) to the cellular DNA repair pathways are useful in monitoring and predicting the response to a therapeutic compound. Accordingly, included in the invention are biomarkers associated with DNA repair and DNA damage response. The invention features methods for identifying subjects who either are or are pre-disposed to developing resistance or are sensitive to a therapeutic compound, e.g., a chemotherapeutic drug by detection of the biomarkers disclosed herein. These biomarkers are also useful for monitoring subjects undergoing treatments and therapies for cancer and cell proliferative disorders, and for selecting therapies and treatments that would be efficacious in subjects having cancer and cell proliferative disorders.

The term "biomarker" in the context of the present invention encompasses, without limitation, proteins, nucleic acids, polymorphisms of proteins and nucleic acids, elements, metabolites, and other analytes. Biomarkers can also include mutated proteins or mutated nucleic acids. The term "analyte" as used herein can mean any substance to be measured and can encompass electrolytes and elements, such as calcium.

Proteins, nucleic acids, polymorphisms, and metabolites whose levels are changed in subjects who have resistance or sensitivity to therapeutic compound, or are predisposed to developing resistance or sensitivity to therapeutic compound are summarized in Table 1 and are collectively referred to herein as, inter alia, "DNA Repair and DNA damage response proteins or DNARMARKER".

Expression of the DNARMARKERS is determined at the protein or nucleic acid level using any method known in the art. For example, at the nucleic acid level Northern hybridization analysis using probes which specifically recognize one or more of these sequences can be used to determine gene expression. Alternatively, expression is measured using reverse-transcription-based PCR assays, e.g., using primers specific for the differentially expressed sequence of genes. Expression is also determined at the protein level, i.e., by measuring the levels of peptides encoded by the gene products described herein, or activities thereof. Such methods are well known in the art and include, e.g., immunoassays based on antibodies to proteins encoded by the genes, aptamers or molecular imprints. Any biological material can be used for the detection/quantification of the protein or its activity. Alternatively, a suitable method can be selected to determine the activity of proteins encoded by the marker genes according to the activity of each protein analyzed.

The DNARMARKER proteins are detected in any suitable manner, but is typically detected by contacting a sample from the patient with an antibody which binds the DNARMARKER protein and then detecting the presence or absence of a reaction product. The antibody may be monoclonal, polyclonal, chimeric, or a fragment of the foregoing, as discussed in detail above, and the step of detecting the reaction product may be carried out with any suitable immunoassay. The sample from the subject is typically a biological fluid as described above, and may be the same sample of biological fluid used to conduct the method described above. The sample may also be in the form of a tissue specimen from a patient where the specimen is suitable for immunohistochemistry in a variety of formats such as paraffin-embedded tissue, frozen sections of tissue, and freshly isolated tissue. The immunodetection methods are antibody-based but there are numerous additional techniques that allow for highly sensitive determinations of binding to an antibody in the context of a tissue. Those skilled in the art will be familiar with various immunohistochemistry strategies.

Immunoassays carried out in accordance with the present invention may be homogeneous assays or heterogeneous assays. In a homogeneous assay the immunological reaction usually involves the specific antibody (e.g., anti-DNARMARKER protein antibody), a labeled analyte, and the sample of interest. The signal arising from the label is modified, directly or indirectly, upon the binding of the antibody to the labeled analyte. Both the immunological reaction and detection of the extent thereof are carried out in a homogeneous solution. Immunochemical labels which may be employed include free radicals, radioisotopes, fluorescent dyes, enzymes, bacteriophages, or coenzymes.

In a heterogeneous assay approach, the reagents are usually the sample, the antibody, and means for producing a detectable signal. Samples as described above may be used. The antibody is generally immobilized on a support, such as a bead, plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the sample. Means for producing a detectable signal include the use of radioactive labels, fluorescent labels, or enzyme labels. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are radioimmunoassays, immunofluorescence methods, chemilumenescence methods, electrochemiluminescence or enzyme-linked immunoassays.

Those skilled in the art will be familiar with numerous specific immunoassay formats and variations thereof which may be useful for carrying out the method disclosed herein. See generally E. Maggio, Enzyme-Immunoassay, (1980) (CRC Press, Inc., Boca Raton, Fla.); see also U.S. Pat. No. 4,727,022 to Skold et al. titled "Methods for Modulating Ligand-Receptor Interactions and their Application," U.S. Pat. No. 4,659,678 to Forrest et al. titled "Immunoassay of Antigens," U.S. Pat. No. 4,376,110 to David et al., titled "Immunometric Assays Using Monoclonal Antibodies," U.S. Pat. No. 4,275,149 to Litman et al., titled "Macromolecular Environment Control in Specific Receptor Assays," U.S. Pat. No. 4,233,402 to Maggio et al., titled "Reagents and Method Employing Channeling," and U.S. Pat. No. 4,230,767 to Boguslaski et al., titled "Heterogenous Specific Binding Assay Employing a Coenzyme as Label."

Antibodies are conjugated to a solid support suitable for a diagnostic assay (e.g., beads, plates, slides or wells formed from materials such as latex or polystyrene) in accordance with known techniques, such as passive binding. Antibodies as described herein may likewise be conjugated to detectable groups such as radiolabels (e.g., 35 S, 125 I, 131 I), enzyme labels (e.g., horseradish peroxidase, alkaline phosphatase), and fluorescent labels (e.g., fluorescein) in accordance with known techniques.

The skilled artisan can routinely make antibodies, nucleic acid probes, e.g., oligonucleotides, aptamers, siRNAs against any of the DNARMARKERS in Table 1.

The invention also includes a DNARMARKER-detection reagent, e.g., nucleic acids that specifically identify one or more DNARMARKER nucleic acids by having homologous nucleic acid sequences, such as oligonucleotide sequences, complementary to a portion of the DNARMARKER nucleic acids or antibodies to proteins encoded by the DNARMARKER nucleic acids packaged together in the form of a kit. The oligonucleotides are fragments of the DNARMARKER genes. For example the oligonucleotides are 200, 150, 100, 50, 25, 10 or less nucleotides in length. The kit may contain in separate containers a nucleic acid or antibody (either already bound to a solid matrix or packaged separately with reagents for binding them to the matrix), control formulations (positive and/or negative), and/or a detectable label. Instructions (e.g., written, tape, VCR, CD-ROM, etc.) for carrying out the assay may be included in the kit. The assay may for example be in the form of a Northern hybridization or a sandwich ELISA as known in the art.

For example, DNARMARKER detection reagent, is immobilized on a solid matrix such as a porous strip to form at least one DNARMARKER detection site. The measurement or detection region of the porous strip may include a plurality of sites containing a nucleic acid. A test strip may also contain sites for negative and/or positive controls. Alternatively, control sites are located on a separate strip from the test strip. Optionally, the different detection sites may contain different amounts of immobilized nucleic acids, i.e., a higher amount in the first detection site and lesser amounts in subsequent sites. Upon the addition of test sample, the number of sites displaying a detectable signal provides a quantitative indication of the amount of DNARMARKER present in the sample. The detection sites may be configured in any suitably detectable shape and are typically in the shape of a bar or dot spanning the width of a test strip.

Alternatively, the kit contains a nucleic acid substrate array comprising one or more nucleic acid sequences. The nucleic acids on the array specifically identify one or more nucleic acid sequences represented by DNARMARKER 1-259. In various embodiments, the expression of 2, 3, 4, 5, 6, 7, 8, 9, 10, 15, 20, 25, 40 or 50 or more of the sequences represented by DNARMARKER 1-259. are identified by virtue of binding to the array. The substrate array can be on, e.g., a solid substrate, e.g., a "chip" as described in U.S. Pat. No. 5,744,305. Alternatively the substrate array can be a solution array, e.g., Luminex, Cyvera, Vitra and Quantum Dots' Mosaic.

Preferably, the kit contains antibodies for the detection of DNARMARKERS.

TABLE 1

| Name | DNARMARKER No. | DNA repair and DNA Damage Pathway |
|---|---|---|
| hOGG1 | 1. | BER |
| hNTH1 | 2. | BER |
| hNEIL1 | 3. | BER |
| hNEIL2 | 4. | BER |
| hNEIL3 | 5. | BER |
| AAG | 6. | BER |
| UNG1 | 7. | BER |
| TDG | 8. | BER |
| MUTY | 9. | BER |
| MTH1 | 10. | BER |
| MBD4 | 11. | BER |
| APE1 | 12. | BER |
| XPG | 13. | BER |
| DNAPOLβ | 14. | BER |
| XRCC1 | 15. | BER |
| PARP1 | 16. | BER |
| DNAPOLδ1 | 17. | BER |
| DNAPOLδ2 | 18. | BER |
| DNAPOLδ3 | 19. | BER |
| DNAPOLδ4 | 20. | BER |
| DNAPOLδ5 | 21. | BER |
| DNAPOLε1 | 22. | BER |
| DNAPOLε2 | 23. | BER |
| DNAPOLε3 | 24. | BER |
| DNAPOLε4 | 25. | BER |
| DNAPOLε5 | 26. | BER |
| DNALigaseI | 27. | BER |
| PCNA | 28. | BER |
| UBC13 | 29. | BER |
| MMS2 | 30. | BER |
| FEN1 | 31. | BER |
| RFC1 | 32. | BER |
| RFC2 | 33. | BER |
| RFC3 | 34. | BER |
| RFC4 | 35. | BER |
| RFC5 | 36. | BER |
| DNALigase1 | 37. | BER |
| DNAligase3 | 38. | BER |
| Aprataxin (Aptx) | 39. | BER |
| XRCC1 | 40. | HR |
| PARP1 | 41. | HR |
| FEN1 | 42. | HR |
| DNA ligase1 | 43. | HR |
| SNM1 | 44. | HR |
| H2A | 45. | HR |
| RPA1 | 46. | HR |
| RPA2 | 47. | HR |
| RPA3 | 48. | HR |
| RAD51 | 49. | HR |
| XRCC2 | 50. | HR |
| XRCC3 | 51. | HR |
| RAD51L1 | 52. | HR |
| RAD51L2 | 53. | HR |
| RAD51L3 | 54. | HR |
| DMC1 | 55. | HR |
| RAD52 | 56. | HR |
| RAD54 | 57. | HR |
| MUS81 | 58. | HR |
| MMS4 | 59. | HR |
| EMSY | 60. | HR |
| BRCA1 | 61. | HR |
| BARD1 | 62. | HR |
| BLM | 63. | HR |
| BLAP75 | 64. | HR |
| SRS2 | 65. | HR |
| SAE2 | 66. | HR |
| ERCC1 | 67. | HR |
| TRF2 | 68. | HR/FA |
| BRCA2/FANCD1 | 69. | HR/FA |
| FANCA | 70. | HR/FA |
| FANCB | 71. | HR/FA |
| FANCC | 72. | HR/FA |
| FANCD1 | 73. | HR/FA |
| FANCD2 | 74. | HR/FA |
| FANCE | 75. | HR/FA |
| FANCF | 76. | HR/FA |
| FANCG | 77. | HR/FA |

TABLE 1-continued

| Name | DNARMARKER No. | DNA repair and DNA Damage Pathway |
|---|---|---|
| FANCJ | 78. | HR/FA |
| FANCL | 79. | HR/FA |
| FANCM | 80. | HR/FA |
| hHef1 | 81. | HR/FA |
| FANCI | 82. | HR/FA |
| USP1 | 83. | HR/FA |
| PALB2/FANCN | 84. | HR/FA |
| DNMT1 | 85. | MMR |
| hMLH1 | 86. | MMR |
| hPMS2 | 87. | MMR |
| hPMS1 | 88. | MMR |
| GTBP (hMSH6) | 89. | MMR |
| hMSH2 | 90. | MMR |
| hMSH3 | 91. | MMR |
| HMGB1 | 92. | MMR |
| MSH4 | 93. | MMR |
| MSH5 | 94. | MMR |
| EXO1 | 95. | MMR |
| DNAPOLδ1 | 96. | MMR |
| DNAPOLδ2 | 97. | MMR |
| DNAPOLδ3 | 98. | MMR |
| DNAPOLδ4 | 99. | MMR |
| DNAPOLδ5 | 100. | MMR |
| DNAPOLε1 | 101. | MMR |
| DNAPOLε2 | 102. | MMR |
| DNAPOLε3 | 103. | MMR |
| DNAPOLε4 | 104. | MMR |
| DNAPOLε5 | 105. | MMR |
| DNA Ligase I | 106. | MMR |
| PCNA | 107. | MMR |
| RPA1 | 108. | MMR |
| RPA2 | 109. | MMR |
| RPA3 | 110. | MMR |
| MUTY | 111. | MMR |
| MRE11 | 112. | DDR |
| RAD50 | 113. | DDR |
| NBS1 | 114. | DDR |
| H2A | 115. | DDR |
| ATM | 116. | DDR |
| P53 | 117. | DDR |
| SMC1 | 118. | DDR |
| ATF2 | 119. | DDR |
| CHK1 | 120. | DDR |
| CHK2 | 121. | DDR |
| MAPKAP Kinase2 | 122. | DDR |
| RPA1 | 123. | DDR |
| RPA2 | 124. | DDR |
| RPA3 | 125. | DDR |
| RAD17 | 126. | DDR |
| RFC1 | 127. | DDR |
| RFC2 | 128. | DDR |
| RFC3 | 129. | DDR |
| RFC4 | 130. | DDR |
| RFC5 | 131. | DDR |
| RAD9 | 132. | DDR |
| RAD1 | 133. | DDR |
| HUS1 | 134. | DDR |
| ATRIP | 135. | DDR |
| ATR | 136. | DDR |
| MDC1 | 137. | DDR |
| CLASPIN | 138. | DDR |
| TOPB1 | 139. | DDR |
| BRCC36 | 140. | DDR |
| BLM | 141. | DDR |
| SRS2 | 142. | DDR |
| SAE2 | 143. | DDR |
| P53BP1 | 144. | DDR |
| ING1 | 145. | DDR |
| ING2 | 146. | DDR |
| SMC1 | 147. | DDR |
| BLAP75 | 148. | DDR |
| BACH1 | 149. | DDR |
| BRCA1 | 150. | DDR |
| BRCA2 | 151. | DDR |
| BARD1 | 152. | DDR |
| RAP80 | 153. | DDR |
| Abraxas | 154. | DDR |

TABLE 1-continued

| Name | DNARMARKER No. | DNA repair and DNA Damage Pathway |
|---|---|---|
| CDT1 | 155. | DDR |
| RPB8 | 156. | DDR |
| PPM1D | 157. | DDR |
| GADD45 | 158. | DDR |
| DTL/CDT2 | 159. | DDR |
| HCLK2 | 160. | DDR |
| CTIP | 161. | DDR |
| BAAT1 | 162. | DDR |
| HDM2/MDM2 | 163. | DDR |
| APLF (aprataxin- and PNK-like factor) | 164. | DDR |
| 14-3-3 σ | 165. | DDR |
| Cdc25A | 166. | DDR |
| Cdc25B | 167. | DDR |
| Cdc25C | 168. | DDR |
| PBIP1 | 169. | DDR |
| H2A | 170. | NER |
| XPC | 171. | NER |
| HR23A | 172. | NER |
| HR23B | 173. | NER |
| DDB1 | 174. | NER |
| DDB2 | 175. | NER |
| XPD | 176. | NER |
| XPB | 177. | NER |
| XPG | 178. | NER |
| CSA | 179. | NER |
| CSB | 180. | NER |
| XPA | 181. | NER |
| XPF | 182. | NER |
| ERCC1 | 183. | NER |
| RNAPolymerase2 | 184. | NER |
| GTF2H1 | 185. | NER |
| GTF2H2 | 186. | NER |
| GTF2H3 | 187. | NER |
| GTF2H4 | 188. | NER |
| GTF2H5 | 189. | NER |
| MNAT1 | 190. | NER |
| MAT1 | 191. | NER |
| CDK7 | 192. | NER |
| CyclinH | 193. | NER |
| PCNA | 194. | NER |
| RFC1 | 195. | NER |
| RFC2 | 196. | NER |
| RFC3 | 197. | NER |
| RFC4 | 198. | NER |
| RFC5 | 199. | NER |
| DNAPOLδ1 | 200. | NER |
| DNAPOLδ2 | 201. | NER |
| DNAPOLδ3 | 202. | NER |
| DNAPOLδ4 | 203. | NER |
| DNAPOLδ5 | 204. | NER |
| DNAPOLε1 | 205. | NER |
| DNAPOLε2 | 206. | NER |
| DNAPOLε3 | 207. | NER |
| DNAPOLε4 | 208. | NER |
| DNAPOLε5 | 209. | NER |
| DNALigaseI | 210. | NER |
| DNAPOLη | 211. | TLS |
| DNAPOLι | 212. | TLS |
| DNAPOLκ | 213. | TLS |
| REV1 | 214. | TLS |
| DNAPOLζ | 215. | TLS |
| DNAPOLθ | 216. | TLS |
| PCNA | 217. | TLS |
| UBC13 | 218. | TLS |
| MMS2 | 219. | TLS |
| RAD5 | 220. | TLS |
| hRAD6A | 221. | TLS |
| hRAD6B | 222. | TLS |
| RAD18 | 223. | TLS |
| WRN | 224. | TLS |
| USP1 | 225. | TLS |
| SIRT6 | 226. | NHEJ |
| H2A | 227. | NHEJ |
| ARP4 | 228. | NHEJ |
| ARP8 | 229. | NHEJ |
| Ino80 | 230. | NHEJ |
| SWR1 | 231. | NHEJ |
| KU70 | 232. | NHEJ |
| KU80 | 233. | NHEJ |
| DNAPKcs | 234. | NHEJ |
| Artemis | 235. | NHEJ |
| PSO2 | 236. | NHEJ |
| XRCC4 | 237. | NHEJ |
| DNA LIGASE4 | 238. | NHEJ |
| XLF | 239. | NHEJ |
| DNAPOLλ | 240. | NHEJ |
| PNK | 241. | NHEJ |
| METNASE | 242. | NHEJ |
| TRF2 | 243. | NHEJ |
| MGMT | 244. | Non-classified |
| TDP1 | 245. | Non-classified |
| DNAPOLμ | 246. | Non-classified |
| hABH1 | 247. | Non-classified |
| hABH2 | 248. | Non-classified |
| hABH3 | 249. | Non-classified |
| hABH4 | 250. | Non-classified |
| hABH5 | 251. | Non-classified |
| hABH6 | 252. | Non-classified |
| hABH7 | 253. | Non-classified |
| hABH8 | 254. | Non-classified |
| TOPO1 | 255. | Non-classified |
| TOPOII | 256. | Non-classified |
| UBC9 | 257. | Non-classified |
| UBL1 | 258. | Non-classified |
| MMS21 | 259. | Non-classified |

Therapeutic Methods

Responsiveness (e.g., resistance or sensitivity) of a cell to an agent is determined by identifying a deficiency in a DNA repair pathway in the cell. The cell is for example a cancer cell. The DNA repair pathway is Base Excision Repair, Nucleotide Excision Repair, Mismatch Repair, Homologous Recombination/Fanconi Anemia (FA) pathway, Non-Homologous Endjoining, or Translesion DNA Synthesis repair (FIGS. 16-18).

The presence of a deficiency in a particular DNA repair pathway indicates that the cell is resistant to agents that are specific for that DNA pathway. Whereas, the absence of a deficiency indicates that the cell is sensitive to agents that are specific for that DNA pathway.

By resistance is meant that the failure if a cell to respond to an agent. For example, resistance to a chemotherapeutic drug means the drug is not damaged or killed by the drug. By sensitivity is meant that that the cell responds to an agent. For example, sensitivity to a chemotherapeutic drug means the drug is damaged or killed by the drug.

For example, responsiveness of a cell to a DNA crosslinking agent or ionizing radiation is identified by identifying a deficiency in the Homologous Recombination/FA pathway. The presence of a deficiency in Homologous Recombination/FA pathway indicates that the cell is sensitive to a DNA crosslinking agent or ionizing radiation. Whereas, the absence of a deficiency indicates that the cell is resistant to DNA crosslinking agent or ionizing radiation. Cross linking reagent include for example cisplatin. Responsiveness of a cancer cell to a Homologous Recombination/FA pathway inhibitor is identified by identifying a deficiency in the mismatch repair DNA pathway. The presence of a deficiency in the mismatch repair DNA pathway indicates that the cell is sensitive to a Homologous Recombination/FA pathway inhibitor. Whereas, the absence of a deficiency indicates that the cell is resistant to a Homologous Recombination/FA pathway inhibitor. Homologous Recombination/FA pathway inhibitors include for example curcumin, velcade or alsterpaulone.

Sensitivity of a cancer cell to a therapeutic drug is increased by inhibiting or reducing the activity one or more DNA repair pathway protein or gene. By increasing the number of inoperative DNA repair pathways, the number of mechanisms by which mechanisms by which the cancer cell can repair DNA damages decreases, which makes the cell more sensitive to the affects of a therapeutic drug. For example, the sensitivity of a cancer cell to DNA cross linking agents or ionizing radiation by contacting the cancer cell with an inhibitor of the Homologous Recombination/FA pathway. Suitable inhibitors include MAP2KAP2 inhibitors.

Therapeutic agents capable of inducing cell death or damage for a particular cell by determining a deficiency in a DNA repair pathway in the cell. Suitable therapeutic agents for that cell would specifically target a DNA pathway other that the deficient pathway. The pathway that is targeted is a pathway that repairs a different type of DNA damage. For example, if the pathway that is deficient is repairs single stranded breaks then the pathway that is targeted repairs double stranded breaks. Likewise if the if the pathway that is deficient is repairs double stranded breaks then the pathway that is targeted repairs single stranded breaks.

Alternatively, the pathway that is targeted is a redundant pathway of the deficient pathway. By redundant pathway it is meant that the pathway repairs similar DNA damage. For example, BER, NER, and MMR all repair single stranded breaks, and therefore are redundant pathways. Thus, if the BER pathway is the deficient pathway it is advantageous to target the NER or MMR pathway. Likewise if the NER pathway is the deficient pathway it is advantageous to target the BER or MMR pathway. If the MMR pathway is the deficient pathway it is advantageous to target the NER or BER pathway Likewise, if the NHEJ pathway is the deficient pathway it is advantageous to target the HR/FA pathway. Similarly, HR/FA and NHEJ both repair double stranded breaks and therefore are redundant pathways. Thus, if the HR/FA pathway is the deficient pathway it is advantageous to target the NHEJ pathway. Likewise, if the NHEJ pathway is the deficient pathway it is advantageous to target the HR/FA pathway.

Drugs that target specific DNA repair pathways are known in the art and include for example the drugs listed on Table 2.

Temozolomide is an alkylating that causes the formation of a critical toxic lesion, O-6 methyl guanine (O-6MG). Inactivation of a DNA repair protein that repairs this lesion, MGMT, was shown to be associated with longer survival in brain cancer patients (Hegi M E, et al. Clin Cancer Res 2004; 10:1871-4.). Additional studies in inoperable glioblastoma have also indicated that response to temozolomide is associated with MGMT (Paz M F, et al. Clin Cancer Res 2004; 10:4933-8).

PARP1 inhibitors are now one of the most widely investigated drug classes for oncology indications. Several companies are progressing PARP1 inhibitors of distinctive chemotypes into clinical trials (reviewed in Ratnam and Low, 2007). It was shown that deficiency in BRCA1 or BRCA2, such as occurs with genetically typed women as a prognostic factor for breast and ovarian cancer, and these being two key factors in the HR pathway, allows tumor cells hypersensitive to PARP1 inhibitors (Bryant et al., 2005; Farmer et al., 2005). These studies have been followed up with the use of PARP1 inhibitors in clinical trials (Brody, L. C. (2005) Treating cancer by targeting a weakness. N. Engl. J. Med. 353, 949-950; Turner, N. et al. (2005) Targeting the DNA repair defect of BRCA tumours. Curr. Opin. Pharmacol. 5, 388-393) raising the possibility of selective cancer therapy against a DNA repair component that targets this tumor weakness. Identifying the spectrum of deficiencies in HR presumably extends beyond BRCA1 and BRCA2, and is likely to involve any of the HR DNA repair proteins and FA DNA repair proteins.

The ATM serine threonine kinase has several known substrates in homologous recombination pathway. Inhibition of this enzyme has been demonstrated to target an inactivation of Homologous recombination (an example paper is Hickson, I. et al. (2004) Identification and characterization of a novel and specific inhibitor of the ataxia-telangiectasia mutated kinase ATM. Cancer Res. 64, 9152-9159).

The DNAPK enzyme is a serine threonine kinase in the Non-homologous endjoining DNA repair pathway. The kinase activity of DNAPK supplies an essential step in this pathway. Inhibition of DNAPK by loss of activity of the enzyme, or by drug treatment, leads to a sensitivity of treated cells to radiation and other forms of DNA damage that are strand breakers.

TABLE 2

| Drug | Target protein | Pathways targeted | Reference |
| --- | --- | --- | --- |
| Methoxyamine | APE1 | Base Excision repair | Liu et al., (2004) |
| E3330 | APE1 | Base Excision repair | Madhusudan et al., (2004) |
| Temzolomide | MGMT | Alkylation repair | Hegi et al. (2004) |
| Abasic site analogs | DNA glycosylase | Base Excision repair | Scharer, O D et al., (2001) |
| UCN01 | Chk1, MapkapKinase2 | DNA damage response | Hawkings (2005) |
| Pamoic acid | DNA polymerase beta | Base excision repair | Hu et al., (2004) |
| INO-1001 & 8 chemical classes | PARP1 | Base excision repair | Ratnam and Low (2007) |
| CRT0044876 | APE1 | Base excision repair | Madhusudan, S. et al. (2005) |
| 80136342 | Unknown | Fanconi anemia/HR | Gallmeier (2007) |
| KU-55933 | ATM | Homologous Recombination | Hickson et al. (2004) |
| Wortmannin & 6 chemical classes | DNAPK | Non-Homologous End joining | Collis, S J (2005) |
| 3indo_2_lyl indazole | Chk1 | DNA damage response | Fraley et al 2006 |

Compounds that target ubiquitin and sumo ligases are also thought to be relevant to inhibition of DNA repair because target enzymes for these agents are known to modify other DNA repair proteins. Ubiquitin and SUMO ligases are important components of homologous recombination, translesion synthesis, nucleotide excision repair, and base excision repair steps. Therefore, inhibitory agents against this class of enzymes will interrupt the designated DNA repair pathways.

The methods are useful to treat, alleviate the symptoms of, monitor the progression of or delay the onset of cancer or a cell proliferative disease in a subject. Cancers and cell proliferative disorders are treated for example by determining if the cancer cell is deficient in a DNA repair pathway and administering a DNA damaging agent or inhibitor specific for at least one different DNA repair pathway. Optionally, a DNA repair pathway protein or gene that is upregulated is identified in the cell and administering a DNA damaging agent or inhibitor specific for a the DNA repair pathway in which the protein or gene is upregulated.

Expression of an effective amount of DNARMARKER proteins, nucleic acids or metabolites also allows for the course of treatment of cancer or a cell proliferative disorder to be monitored. In this method, a biological sample is provided from a subject undergoing treatment, e.g., chemotherapeutic treatment, for cancer or a cell proliferative disorder. If desired, biological samples are obtained from the subject at various time points before, during, or after treatment. Expression of an effective amount of DNARMARKER proteins, nucleic acids or metabolites is then determined and compared to a reference, e.g. a control individual or population whose cancer or a cell proliferative disorder state is known or an index value. The reference sample or index value may be taken or derived from one or more individuals who have been exposed to the treatment. Alternatively, the reference sample or index value may be taken or derived from one or more individuals who have not been exposed to the treatment. For example, samples may be collected from subjects who have received initial treatment for cancer or a cell proliferative disorder and subsequent treatment for diabetes to monitor the progress of the treatment.

Differences in the genetic makeup of individuals can result in differences in their relative abilities to metabolize various drugs. Accordingly, the DNARMARKER disclosed herein allow for a putative therapeutic or prophylactic to be tested from a selected subject in order to determine if the agent is a suitable for treating or preventing cancer or a cell proliferative disorder in the subject.

To identify therapeutic that is appropriate for a specific subject a the expression of one or more of DNARMARKER proteins, nucleic acids or metabolites is in a test sample form the subject is determined.

The pattern of DNARMARKER expression in the test sample is measured and compared to a reference profile, e.g., a therapeutic compound reference expression profile. Comparison can be performed on test and reference samples measured concurrently or at temporally distinct times. An example of the latter is the use of compiled expression information, e.g., a sequence database, which assembles information about expression levels of DNARMARKERS.

If the reference sample, e.g., a control sample is from cells that are sensitive to a therapeutic compound then a similarity in the amount of the DNARMARKER proteins in the test sample and the reference sample indicates that treatment with that therapeutic compound will be efficacious. However, a change in the amount of the DNARMARKER in the test sample and the reference sample indicates treatment with that compound will result in a less favorable clinical outcome or prognosis. In contrast, if the reference sample, e.g., a control sample is from cells that are resistant to a therapeutic compound then a similarity in the amount of the DNARMARKER proteins in the test sample and the reference sample indicates that the treatment with that compound will result in a less favorable clinical outcome or prognosis. However, a change in the amount of the DNARMARKER in the test sample and the reference sample indicates that treatment with that therapeutic compound will be efficacious.

By "efficacious" is meant that the treatment leads to an decrease in the amount of a DNARMARKER protein, or a decrease in size, prevalence, or metastatic potential of cancer in a subject. When treatment is applied prophylactically, "efficacious" means that the treatment retards or prevents cancer or a cell proliferative disorder from forming. Assessment of cancer and cell proliferative disorders is made using standard clinical protocols.

Cancer includes solid tumors such as breast, ovarian, prostate, lung, kidney, gastric, colon, testicular, head and neck, pancreas, brain, melanoma, and other tumors of tissue organs and cancers of the blood cells, such as lymphomas and leukemias, including acute myelogenous leukemia, chronic lymphocytic leukemia, T cell lymphocytic leukemia, and B cell lymphomas.

A "cellular proliferative disorder" includes those disorders that affect cell proliferation, activation, adhesion, growth, differentiation, or migration processes. As used herein, a "cellular proliferation, activation, adhesion, growth, differentiation, or migration process" is a process by which a cell increases in number, size, activation state, or content, by which a cell develops a specialized set of characteristics which differ from that of other cells, or by which a cell moves closer to or further from a particular location or stimulus. Disorders characterized by aberrantly regulated growth, activation, adhesion, differentiation, or migration. cell proliferative disorders" include autoimmune diseases and inflammation. for example, an inflammatory or immune system disorder, and/or a cellular proliferative disorder.

The subject is preferably a mammal. The mammal is, e.g., a human, non-human primate, mouse, rat, dog, cat, horse, or cow. The subject has been previously diagnosed as having cancer or a cell proliferative disorder, and possibly has already undergone treatment for the cancer or a cell proliferative disorder.

The subject is suffering from or at risk of developing cancer or a cell proliferative disorder. Subjects suffering from or at risk of developing cancer or a cell proliferative disorder are identified by methods known in the art.

By agents that are specific for a particular DNA repair pathway is meant the agent induces the type of DNA damage that the particular DNA repair pathway corrects.

By deficiency is meant that that cell has a reduced or abrogated ability to repair DNA damage through that pathway. Activity may be determined relative to normal (i.e. non-cancer) cells, preferably from the same tissue. A deficiency in a pathway is determined by methods known in the art. For example, activity of the HR repair pathway may be determined by measuring the formation of foci containing Rad51 in the nucleus in response to DNA damaging agents. Cells deficient in the HR repair pathway lack the ability to produce such foci. The presence of Rad51 foci may be determined using standard immunofluorescent techniques. Alternatively, the deficiency is determined by measuring the expression (e.g. increase or decrease relative to a control), detecting a sequence variation or posttranslational modification of one or more DNARMARKERS described herein.

Posttranslational modification include for example, phosphorylation, ubiquitination, sumo-ylation, acetylation, alkylation, methylation, glycylation, glycosylation, isoprenylation, lipoylation, phosphopantetheinylation, sulfation, selenation and C-terminal amidation. For example, a deficiency in the Homologous Recombination/FA pathway is determined by detecting the monoubiquitination of FANCD2. Similarly, responsiveness of cancer cell to a MAP2KAP2 inhibitor is determined by detecting phosphorylation of a MAP2KAP2 protein. Phosphorylation indicates the cell is sensitive to a MAP2KAP2 inhibitor. In contrast the absence of phosphorylation indicates the cell is resistant to a MAP2KAP2 inhibitor.

Sequence variations such as mutations and polymorphisms may include a deletion, insertion or substitution of one or more nucleotides, relative to the wild-type nucleotide sequence. The one or more variations may be in a coding or non-coding region of the nucleic acid sequence and, may reduce or abolish the expression or function of the DNA repair pathway component polypeptide. In other words, the variant nucleic acid may encode a variant polypeptide which has reduced or abolished activity or may encode a wild-type polypeptide which has little or no expression within the cell, for example through the altered activity of a regulatory element. A variant nucleic acid may have one, two, three, four or more mutations or polymorphisms relative to the wild-type sequence.

The presence of one or more variations in a nucleic acid which encodes a component of a DNA repair pathway, is determined for example by detecting, in one or more cells of a test sample, the presence of an encoding nucleic acid sequence which comprises the one or more mutations or polymorphisms, or by detecting the presence of the variant component polypeptide which is encoded by the nucleic acid sequence.

Various methods are available for determining the presence or absence in a sample obtained from an individual of a particular nucleic acid sequence, for example a nucleic acid sequence which has a mutation or polymorphism that reduces or abrogates the expression or activity of a DNA repair pathway component. Furthermore, having sequenced nucleic acid of an individual or sample, the sequence information can be retained and subsequently searched without recourse to the original nucleic acid itself. Thus, for example, scanning a database of sequence information using sequence analysis software may identify a sequence alteration or mutation.

Methods according to some aspects of the present invention may comprise determining the binding of an oligonucleotide probe to nucleic acid obtained from the sample, for example, genomic DNA, RNA or cDNA. The probe may comprise a nucleotide sequence which binds specifically to a nucleic acid sequence which contains one or more mutations or polymorphisms and does not bind specifically to the nucleic acid sequence which does not contain the one or more mutations or polymorphisms, or vice versa. The oligonucleotide probe may comprise a label and binding of the probe may be determined by detecting the presence of the label.

A method may include hybridization of one or more (e.g. two) oligonucleotide probes or primers to target nucleic acid. Where the nucleic acid is double-stranded DNA, hybridization will generally be preceded by denaturation to produce single-stranded DNA. The hybridization may be as part of a PCR procedure, or as part of a probing procedure not involving PCR. An example procedure would be a combination of PCR and low stringency hybridization.

Binding of a probe to target nucleic acid (e.g. DNA) may be measured using any of a variety of techniques at the disposal of those skilled in the art. For instance, probes may be radioactively, fluorescently or enzymatically labeled. Other methods not employing labeling of probe include examination of restriction fragment length polymorphisms, amplification using PCR, RN'ase cleavage and allele specific oligonucleotide probing. Probing may employ the standard Southern blotting technique. For instance, DNA may be extracted from cells and digested with different restriction enzymes. Restriction fragments may then be separated by electrophoresis on an agarose gel, before denaturation and transfer to a nitrocellulose filter. Labeled probe may be hybridized to the DNA fragments on the filter and binding determined.

Those skilled in the art are well able to employ suitable conditions of the desired stringency for selective hybridization, taking into account factors such as oligonucleotide length and base composition, temperature and so on. Suitable selective hybridization conditions for oligonucleotides of 17 to 30 bases include hybridization overnight at 42° C. in 6×SSC and washing in 6×SSC at a series of increasing temperatures from 42° C. to 65° C. Other suitable conditions and protocols are described in Molecular Cloning: a Laboratory Manual: 3rd edition, Sambrook & Russell (2001) Cold Spring Harbor Laboratory Press NY and Current Protocols in Molecular Biology, Ausubel et al. eds. John Wiley & Sons (1992).

Nucleic acid, which may be genomic DNA, RNA or cDNA, or an amplified region thereof, may be sequenced to identify or determine the presence of polymorphism or mutation therein. A polymorphism or mutation may be identified by comparing the sequence obtained with the database sequence of the component, as set out above. In particular, the presence of one or more polymorphisms or mutations that cause abrogation or loss of function of the polypeptide component, and thus the DNA repair pathway as a whole, may be determined.

Sequencing may be performed using any one of a range of standard techniques. Sequencing of an amplified product may, for example, involve precipitation with isopropanol, resuspension and sequencing using a TaqFS+Dye terminator sequencing kit. Extension products may be electrophoresed on an ABI 377 DNA sequencer and data analyzed using Sequence Navigator software.

A specific amplification reaction such as PCR using one or more pairs of primers may conveniently be employed to amplify the region of interest within the nucleic acid sequence, for example, the portion of the sequence suspected of containing mutations or polymorphisms. The amplified nucleic acid may then be sequenced as above, and/or tested in any other way to determine the presence or absence of a mutation or polymorphism which reduces or abrogates the expression or activity of the DNA repair pathway component. Suitable amplification reactions include the polymerase chain reaction (PCR) (reviewed for instance in "PCR protocols; A Guide to Methods and Applications", Eds. Innis et al, 1990, Academic Press, New York, Mullis et al, Cold Spring Harbor Symp. Quant. Biol., 51:263, (1987), Ehrlich (ed), PCR technology, Stockton Press, N Y, 1989, and Ehrlich et al, Science, 252:1643-1650, (1991)).

Mutations and polymorphisms associated with cancer may also be detected at the protein level by detecting the presence of a variant (i.e. a mutant or allelic variant) polypeptide.

A method of identifying a cancer cell in a sample from an individual as deficient in DNA repair may include contacting a sample with a specific binding member directed against a variant (e.g. a mutant) polypeptide component of the pathway, and determining binding of the specific binding member to the sample. Binding of the specific binding member to the sample may be indicative of the presence of the variant polypeptide component of the DNA repair pathway in a cell within the sample. Preferred specific binding molecules for use in aspects of the present invention include antibodies and fragments or derivatives thereof ('antibody molecules').

The reactivities of a binding member such as an antibody on normal and test samples may be determined by any appropriate means. Tagging with individual reporter molecules is one possibility. The reporter molecules may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding binding molecule (e.g. antibody) and reporter molecule.

Examples are provided below to further illustrate different features of the present invention. The examples also illustrate useful methodology for practicing the invention. These examples do not limit the claimed invention.

EXAMPLES

Example 1

Identification of siRNA Targets Selectively Toxic to FA Pathway Deficient Cells

The EUFA 326 cell line is a patient derived FA-G fibroblast line. This cell line was previously corrected with a FANCG expressing construct to make the isogenic EUFA326G cell line (Garcia-Higuera et al., Blood 96(9): 3224-3230, 2000). These cell lines were selected for screening purposes as they grow at comparable rates and were found to demonstrate equal levels of gene knockdown with siRNA oligonucleotides.

Figure 1A:
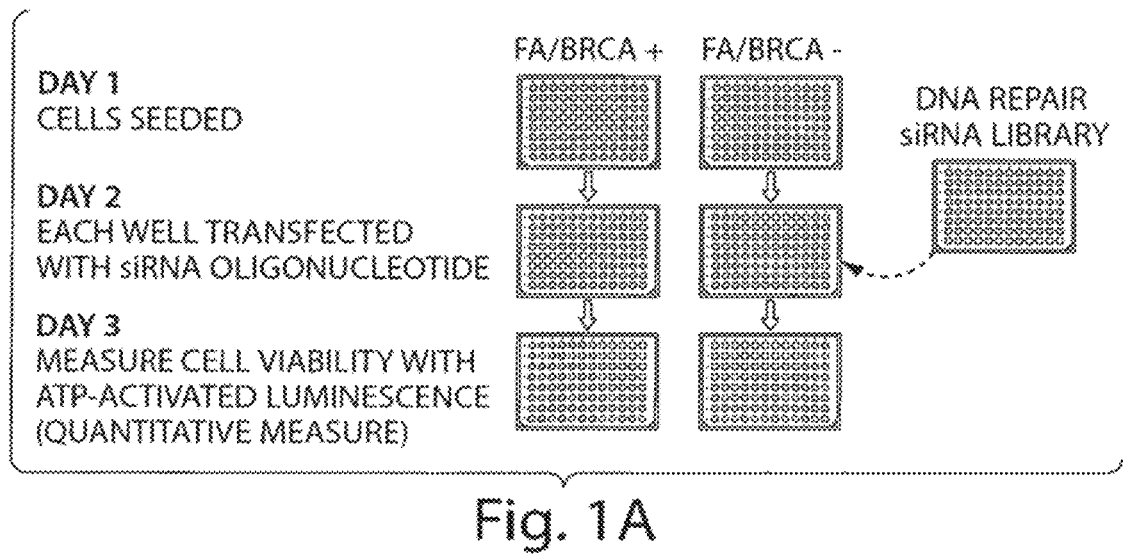
FIG. 1A is schematic showing the siRNA screen.
Figure 1B:
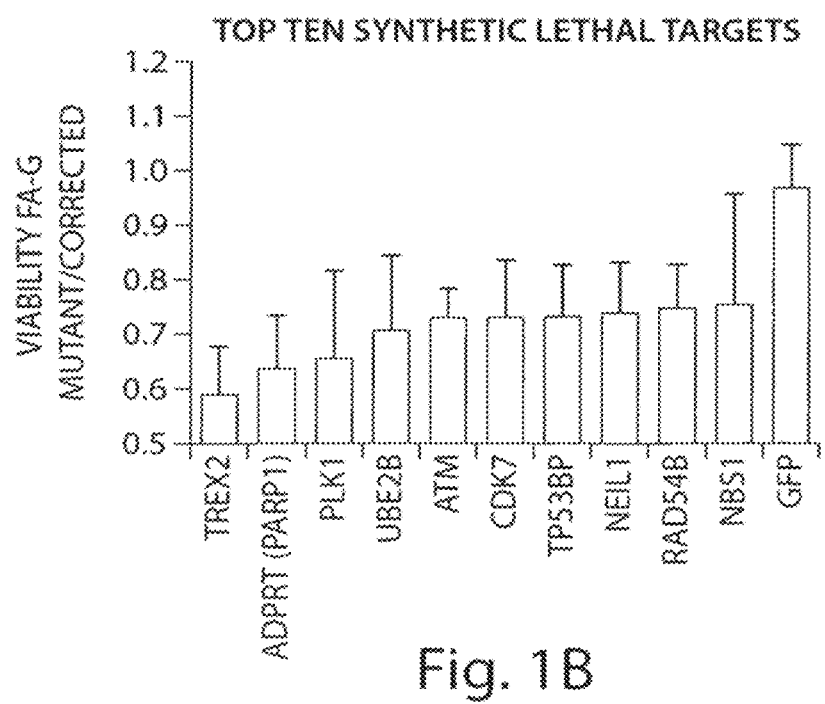
FIG. 1B is a graph showing the top ten siRNA targets that are selectively toxic to the FA pathway deficient cells.

The Qiagen DNA repair siRNA library that contains siRNA oligonucleotides targeting 356 DNA damage response genes was used for the screening assays. A feature of this library is the inclusion of two individual siRNA oligonucleotides targeting each individual gene in order to reduce the risk of off target effects. FIGS. 1A and 1B depict the identification of DNA Damage Response Genes required in FA pathway deficient cells. FIG. 1A shows a schematic of the siRNA screen. Cells were plated in 96 well plates at 1000 cells per well on day 1. On day 2 each well was transfected with an siRNA oligonucleotide directed towards one DNA damage response gene. On day 6 cellular viability was measured using an ATP activated bioluminescence assay. The screen was repeated twice.

After siRNA transfection, the relative survival between the EUFA326 and the EUFA326G cell line was calculated for each oligonucleotide. The assay was repeated twice and the mean relative survival in the EUFA326 versus the EUFA326G cell line was calculated for each gene target. The mean relative survival between the EUFA326 and EUFA326E cell line along with the standard error of the mean (SEM) for each gene target was calculated from 4 individual measurements. The 4 survival values for each siRNA target represent duplicate results from the two oligonucleotides targeting each gene. Table 3 shows that the top ten siRNA oligonucleotide targets that are selectively toxic to FA pathway deficient EUFA326 cells when compared to the corrected EUFA326G cell line. In FIG. 1B the top ten siRNA targets that are selectively toxic to the FA pathway deficient EUFA326 cell line when compared to the EUFA326C corrected cell line are represented graphically. The Y axis represents the relative survival of the EUFA326 cell line compared to the EUFA326 corrected cell line. The SEM from 4 measurements is given for target. GFP is a control siRNA with no mammalian target.

Importantly, it was found that knockdown of either of the base excision repair genes PARP1 or NEIL1 was selectively toxic to FA pathway deficient cells, with a relative survival of 64% for PARP1 knockdown and 74% for NEIL1 knockdown compared to the corrected cell line. This is in keeping with a recent study reporting that FA pathway deficient MEF cells are selectively sensitive to disruption of BER by PARP inhibitors (McCabe et al., Cancer Res 66(16): 8109-8115, 2006) and indicated that the screening assay is a valid approach for identifying novel targets and associations between DNA repair pathways. In addition, depletion of other proteins in DNA repair pathways also leads to reduction in cell survival in the above experiments. For example, the ratio of EUFA326/EUFA326G viability was also changed for siRNA knockdown of other DNA repair and DNA damage response genes (Table 3).

Therefore inhibitors of PARP1 and other BER enzymes, such as NEIL1, other Uracil Deglycosylases, DNA polymerase beta, and inhibitors of BER acting by disruption of protein:protein associations may have utility in the clinic by implementing a biomarker strategy that involves surveying the activity/depletion of DNA repair and DNA damage response pathways as described in this invention. DNAR biomarkers that identify DNA repair and DNA damage signaling modulation and/or protein levels are particularly relevant to drugs and classes of drugs that inhibit one or more target protein member of one of the DNA repair and/or DNA damage signaling pathways.

Shown in this example, one type of a PARP1 inhibitor (siRNA for PARP1) is used to define an hypersensitivity of cells that are depleted in a FA gene. In addition to siRNA experiments, it would be assumed that selective inhibitors of PARP1 (such as small molecules, peptides, therapeutic antibodies and other biotherapeutics) would have a similar outcome. A PARP1 inhibitor may have select utility when applied to clinical specimens being evaluated for treatment decisions in oncology, be it as monotherapies or as combination therapies with other chemotherapeutic agents or radiation. Patients with cancers that have been defined by the DNAR biomarkers for the Fanconi Anemia pathway would be expected to identify the patient subset particularly sensitive or resistant to PARP1 inhibitors. Understanding the DNA repair status of one or more of the DNA repair and damage pathways is an important determinant of responsiveness versus resistance of the drug class.

Monitoring DNA repair deficiency as shown here is a means to evaluate the responsiveness of a tumor to target-directed therapies in addition to chemotherapies. To further evaluate the connection between identifying a DNA repair change by molecular monitoring of a DNA repair pathway (FA deficiency) and change to the other pathways, an incubation with an inhibitor of the second DNA repair or DNA damage protein was used. If cells of known changed DNA repair status are hypersensitive to inhibition of a protein in the other identified pathway, then the implication is that the cells become hyper-dependant on that second protein and pathway.

Therefore, the identification of a connection between FA-deficiency and PARP1 was also tested by examining the hypersensitivity of these cells to PARP1 inhibitors. FANCA-deficient cells were compared with FANCA-deficient cells that were complemented with the FANCA gene introduced by retroviral transduction. In the experiment shown in FIG. 34, the FANCA-deficient cells are specifically sensitive to the PARP1 inhibitor, 4-amino-1,8 naphthalimide. This finding shows that evaluation of one example of a DNA repair pathway change (FA deficiency) can be used to direct the application of an inhibitor in another protein or pathway. The application of this discovery will be a useful therapeutic strategy in oncology.

Example 2

Concomitant Loss of the FA Pathway and ATM Function is Toxic to Cells

Interestingly, knockdown of TP53BP1 or ATM was selectively toxic to FA pathway deficient EUFA326 cells, with a relative survival of 60% and 70% respectively when compared to the EUFA326G cell line (Table 3 and FIG. 1B). Knockdown of NBS1 also demonstrated selective toxicity in the EUFA326 cells although the SEM of survival overlapped with the control siGFP oligonucleotide (Table 3 and FIG. 1B). NBS1 and TP53BP1 have previously been reported to be involved in the ATM-mediated response to double strand DNA breaks (DSBs). Therefore, these data indicated a hyper-dependence on the ATM DSB signaling pathway in FA pathway deficient cells.

Figure 2A:
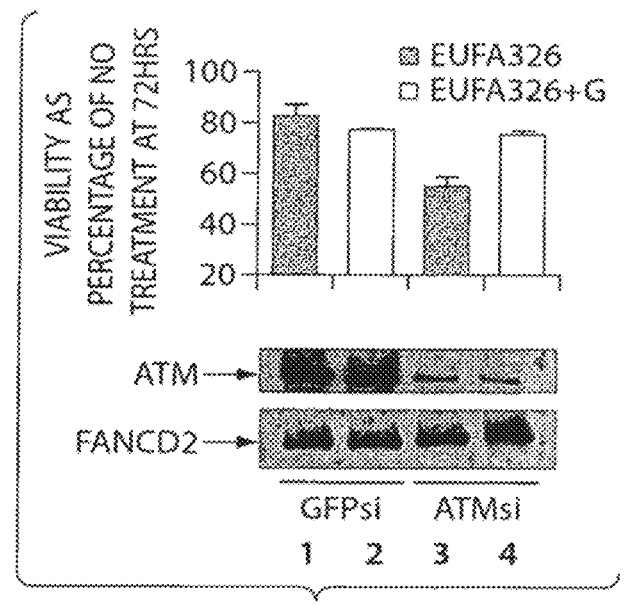
FIG. 2A is photograph of an immunoblot and an accompanying graphic representation showing the of cell viability following treatment with siRNA targeting ATM.
Figure 2B:
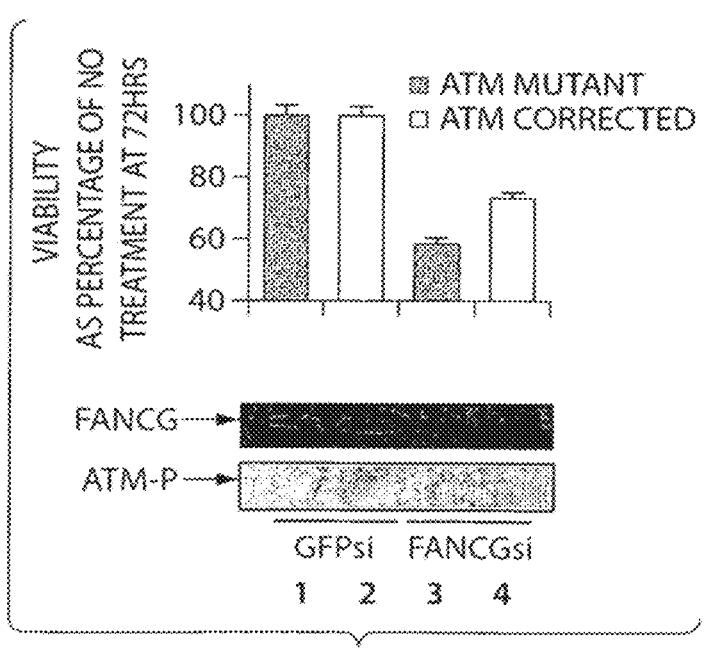
FIG. 2B is photograph of an immunoblot and an accompanying graphic representation showing the of cell viability following treatment with siRNA targeting FANCG.
Figure 2C:
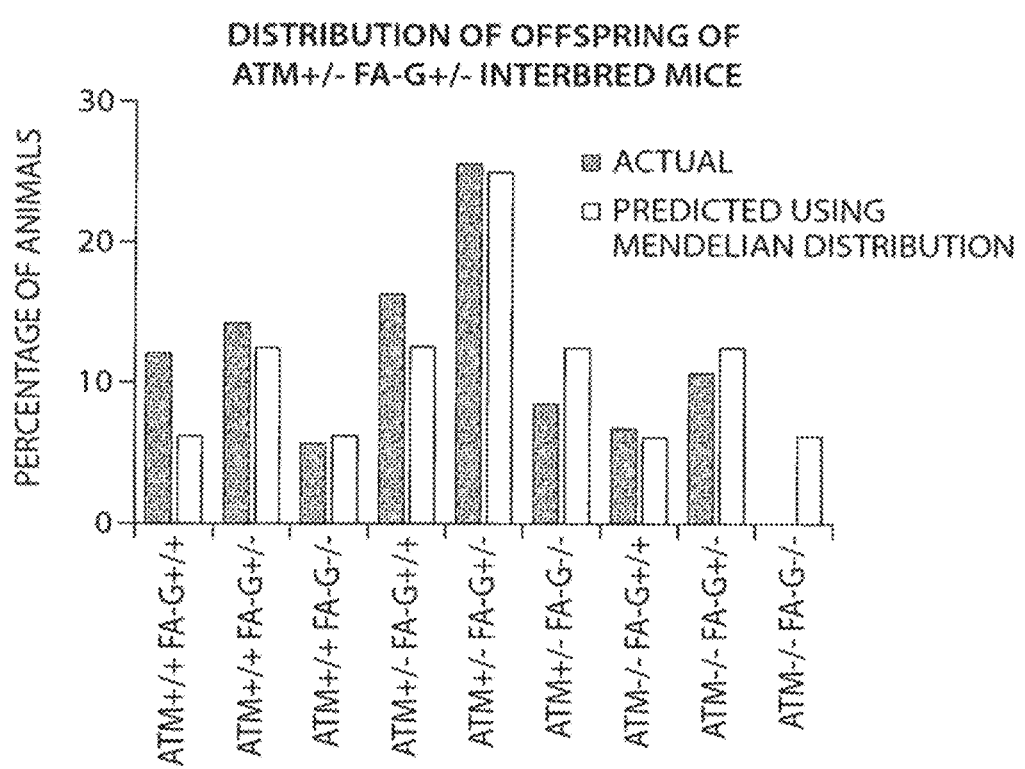
FIG. 2C is a graph showing the genotype frequency in the offspring of Fancg+/− ATM+/− interbred mice.

In order to confirm that FA pathway deficient cells required ATM function, the EUFA326 and EUFA326G cell lines were transfected with an alternative ATM siRNA oligonucleotide. FIGS. 2A-2C show the combined loss of the FA pathway and ATM function is toxic to cells. FIG. 2A, lanes 1 and 3 of the Western blot and bars 1 and 3 of the graph represent the FA pathway deficient EUFA326 cell line, lanes 2 and 4 of the Western blot and bars 2 and 4 of the 72 hr viability graph represent the corrected EUFA326G cell line. Each cell line was treated for 72 hrs with control GFP siRNA (lanes 1 and 2) or siRNA targeting ATM (lanes 3 and 4). Viability is given as a percentage of a no siRNA treatment control for each cell line. FIG. 2B, lanes 1 and 3 of the Western blot and bars 1 and 3 of the 72 hr viability graph represent the ATM deficient AT22 cell line, lanes 2 and 4 of the Western blot and bars 2 and 4 of the viability graph represent AT22-ATM corrected cell line. Each cell line was treated for 72 hrs with control GFP siRNA (lanes 1 and 2) or siRNA targeting FANCG (lanes 3 and 4). Viability is given as a percentage of a no siRNA treatment control for each cell line. FIG. 2C shows a graphical representation of the genotype frequency in the offspring of Fancg+/−ATM+/− interbred mice. The black bar represents the measured frequency for each genotype, whereas the white bar represents the calculated frequency by Mendelian genetics.

Consistent with the screen results, the EUFA326 cell line was more sensitive to ATM knockdown (viability 54.9% of GFPsi control) than the EUFA326G cell line (viability 75.5% of GFPsi control), (FIG. 2A). FANCD2 monoubiquitination is a marker of activation of the FA pathway (Garcia-Higuera et al., Mol Cell 7(2): 249-262, 2001). Treatment with ATM siRNA in the EUFA326G cell line resulted in FANCD2 monoubiquitination as measured by Western blotting (FIG. 2A, Lane 4) compared to GFPsi control (FIG. 2A, Lane 2), indicating that the FA pathway was activated by the loss of ATM expression, even in the absence of exogenous genotoxic stress.

Since FA pathway deficient cells did not tolerate loss of ATM expression, it was asked if the converse was true, namely, if ATM deficient cells were sensitive to loss of the FA pathway. ATM deficient AT22 cells and an isogenic ATM corrected cell line were transfected with siRNA targeting FANCG and cellular viability was measured at 72 hours (FIG. 2B). The ATM deficient cell line was more sensitive to loss of FANCG (viability 58.3% of GFPsi control) than the corrected cell line (viability 73.1% of GFPsi control) further supporting the hypothesis that the concomitant loss of both the FA pathway and ATM function is toxic to cells. Phosphorylation of serine 1981 on ATM has previously been reported as a marker of ATM activation (Bakkenist and Kastan, Nature 421(6922): 499-506, 2003). Treatment with siRNA to FANCG resulted in ATM auto-phosphorylation in the ATM corrected cell line as measured by Western blotting (FIG. 2B, Lane 4) when compared to the same cell line treated with GFP control siRNA (FIG. 2B, Lane 2). These results indicated that ATM is activated in response to loss of the FA pathway.

The validity of targeting DNA response pathways in cancer treatment has recently been demonstrated by two groups. In these preclinical studies, inhibition of PARP1, a component of base excision repair, resulted in specific toxicity to BRCA1 and BRCA2 deficient (and therefore homologous recombination defective) cells while having little effect on cells competent for DNA repair (Bryant et al., Nature 434(7035): 913-917, 2005; Farmer et al., Nature 434(7035): 917-921, 2005).

Loss of the FA pathway has been reported in a number of different tumor types, therefore it was asked if inhibition of alternative DNA damage response pathways could be selectively toxic to cells that have lost FA pathway function. An siRNA screening approach identified the ATM DNA damage response kinase as being required for the survival of FA pathway deficient cells. Moreover, ATM deficient cells were sensitive to loss of FANCG indicating that the combined loss of both ATM and FA pathway function is toxic to cells. Interestingly FA pathway deficient cells were found to have constitutive activation of ATM and this was predominantly during the S phase of the cell cycle. Although ATM was active in FA pathway deficient cells, the level of activation was relatively low when compared to irradiated cells. These data indicate that the endogenous DNA damage resulting in ATM activation is at a relatively low level, and occurs mostly during DNA synthesis. This is in keeping with recent studies that have demonstrated that xenopus egg cells immunodepleted for FANCA or FANCD2 have a higher level of spontaneous DS DNA breaks during DNA replication when compared to normal cells (Sobeck et al., Mol Cell Biol 26(2): 425-437, 2006). It is predicted that the low level of ATM activation observed in human FA cell lines is in response to these spontaneous S phase DNA breaks. The observation that inhibition of ATM by siRNA resulted in selective cell death in FA pathway deficient cells, indicates that this S phase activation of ATM, although relatively low, is critical for cell survival.

Therefore inhibitors of Atm kinase and other DNA damage signaling steps may have increased utility in the clinic by implementing a biomarker strategy that involves surveying the activity/depletion of DNA repair and DNA damage response pathways as described in this invention. DNAR biomarkers that identify DNA repair and DNA damage signaling modulation and/or protein levels are particularly relevant to drugs and classes of drugs that inhibit one or more target protein member of one of the DNA repair and/or DNA damage signaling pathways.

Shown in Examples 2-7, it would be assumed that selective inhibitors of Atm (such as small molecules, peptides, therapeutic antibodies and other biotherapeutics) would have a similar outcome. A Atm inhibitor may have select utility when applied to clinical specimens being evaluated for treatment decisions in oncology, be it as monotherapies or as combination therapies with other chemotherapeutic agents or radiation. Patients with cancers that have been defined by the DNAR biomarkers for the Fanconi Anemia pathway would be expected to identify the patient subset particularly sensitive or resistant to Atm inhibitors. Understanding the DNA repair status of one or more of the DNA repair and damage pathways is an important determinant of responsiveness versus resistance of the drug class.

Example 3

Double Knockout of Murine Fancg and Atm Results in Embryonic Lethality

The ATM pathway is known to converge with the FA pathway, following ionizing radiation treatment, through the ATM-mediated phosphorylation of FANCD2 (Taniguchi et al., Cell 109(4): 459-472, 2002). Therefore, the FA and ATM pathway was investigated though the interbreeding of Fancg+/− Atm+/− mice. A consistent observation has been the preimplantation lethality of Atm−/− Fancg−/− offspring (FIG. 2C). Table 4 shows the frequency of geneotypes of offspring from interbred FancG+/− Atm+/− mice compared to the predicted frequencies by Mendelian Genetics. Interestingly, Fancg+/−Atm−/− and Fancg−/− Atm+/− progeny have also been less frequent that would have been expected by Mendelian genetics (12.5% vs 16.47% and 8.54% vs 12.5% respectively). The non-viability of FANCG−/−ATM−/− mice (FIG. 2E and Table 4) further emphasizes the importance of ATM function in the context of an absent FA pathway. These data are consistent with the siRNA screen, indicating that cells will not tolerate a loss in both ATM and FA pathway function.

Example 4

FA Pathway Deficient Cells Demonstrate Constitutive Activation of ATM to Prevent DNA Breakage The mechanism underlying the sensitivity of FA pathway deficient cells to loss of ATM function was also investigated. The protein from isogenic pairs of FA pathway functional and deficient cells was extracted and auto-phosphorylation of ATM was measured by Western blotting.

Figure 3A:
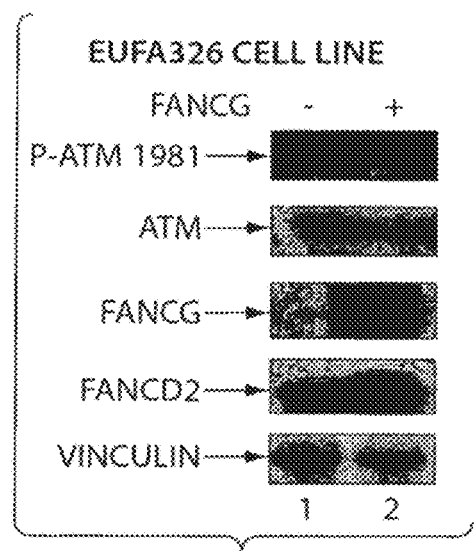
FIG. 3A is a photograph of an immunoblot showing the auto-phosphorylation of ATM in the FANCG deficient EUFA326 cell line.
Figure 3B:
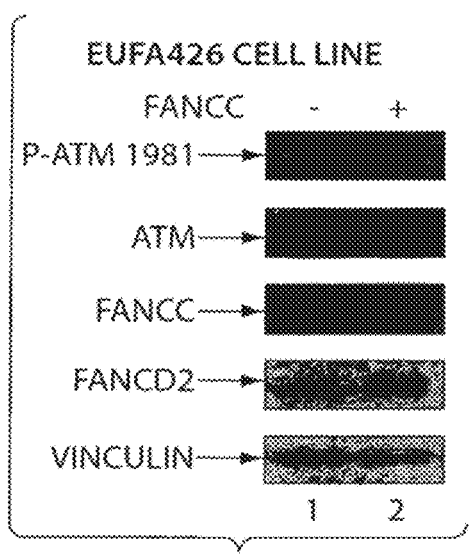
FIG. 3B is a photograph of an immunoblot showing the auto-phosphorylation of ATM in the FANCC deficient EUFA426 cell line.
Figure 3C:
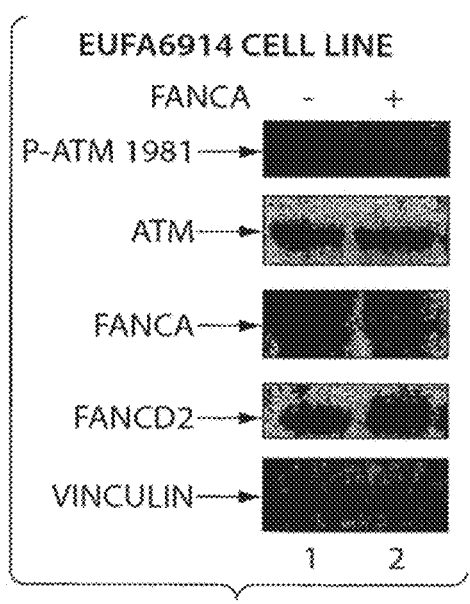
FIG. 3C is a photograph of an immunoblot showing the auto-phosphorylation of ATM in the FANCA deficient EUFA6914 cell line.
Figure 3D:
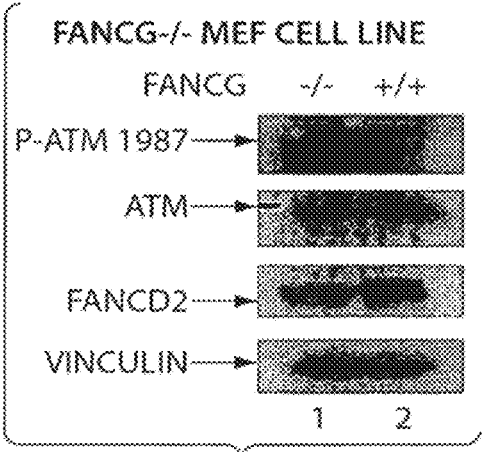
FIG. 3D is a photograph of an immunoblot showing the auto-phosphorylation of ATM in the FancG−/− MEF cell line and the FancG wildtype MEF cell line.
Figure 3E:
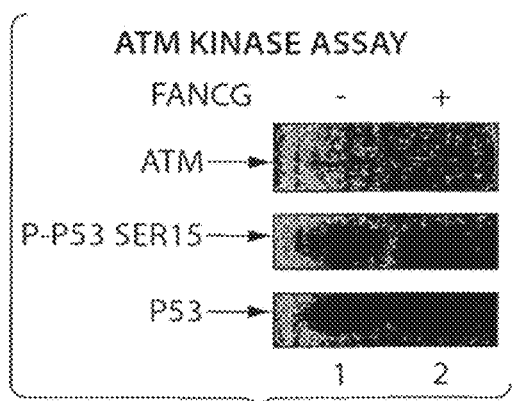
FIG. 3E is a photograph of an immunoblot showing an ATM kinase assay.
Figure 3F:
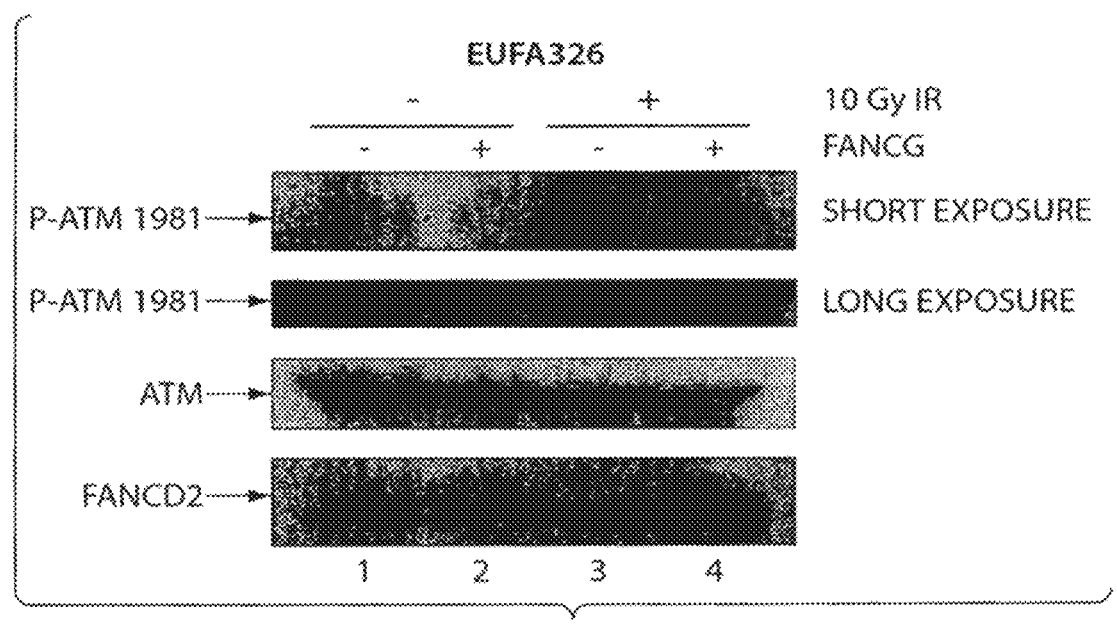
FIG. 3F is a photograph of an immunoblot showing ATM auto-phosphorylation and FANCD2 monoubiqitination before and after treatment with ionizing radiation.
Figure 3G:
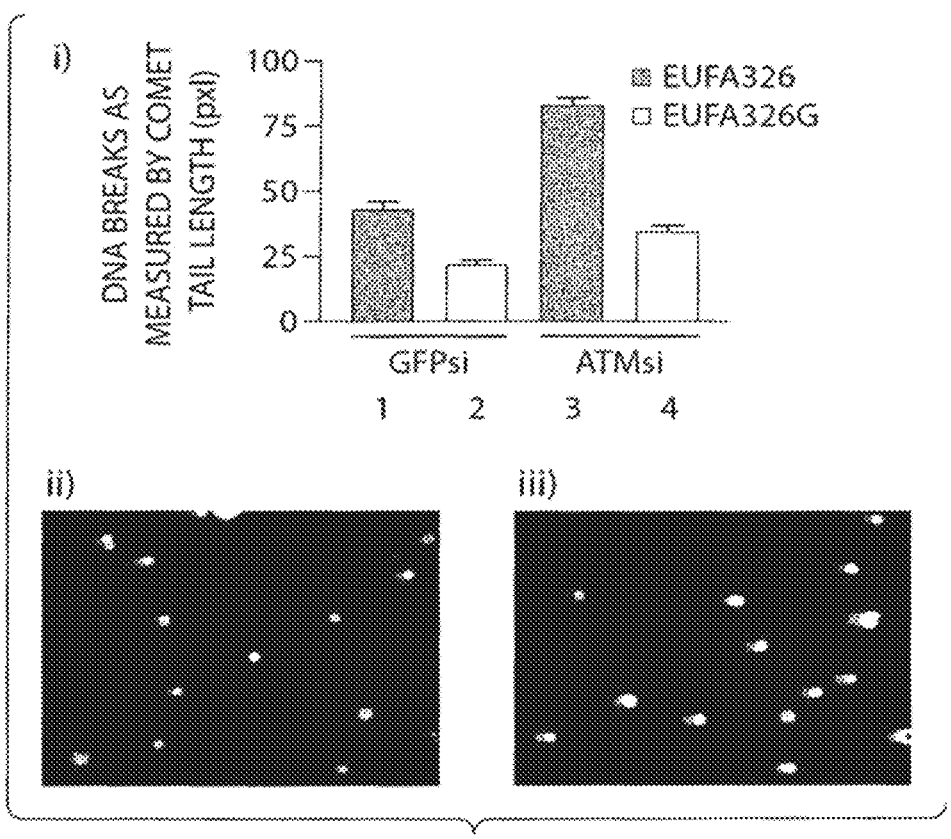
FIG. 3G is a graph and accompanying field photographs showing a Comet assay comparing DNA breaks following treatment with siRNA to ATM.

FIGS. 3A-3G show that FA pathway deficient cells demonstrate constitutive activation of ATM. FIG. 3, Panel A, shows a Western blot comparing auto-phosphorylation of ATM between the FANCG deficient EUFA326 cell line (lane 1) and the isogenic corrected cell line (lane 2). FIG. 3B shows a Western blot comparing auto-phosphorylation of ATM between the FANCC deficient EUFA426 cell line (lane 1) and the isogenic corrected cell line (lane 2). FIG. 3C shows a Western blot comparing auto-phosphorylation of ATM between the FANCA deficient EUFA6914 cell line (lane 1) and the isogenic corrected cell line (lane 2). FIG. 3D shows a Western blot comparing auto-phosphorylation of ATM between the FancG−/− MEF cell line (lane 1) and the FancG wildtype MEF cell line (lane 2). FIG. 3E shows an ATM kinase assay comparing the kinase activity of ATM immunoprecipitated from FA pathway deficient EUFA326 and FA pathway competent EUFA326G cells towards serine 15 on recombinant p53. FIG. 3F shows a Western blot assessing ATM auto-phosphorylation and FANCD2 monoubiqitination in FA pathway deficient EUFA326 cells (lanes 1 and 3) and FA pathway corrected EUFA326G cells (lanes 2 and 4) at baseline (lanes 1 and 2) and 6 hrs after 10 Gy ionizing radiation (lanes 3 and 4). FIG. 3G, shows a Comet assay comparing DNA breaks in EUFA326 versus EUFA326G cells 72 hrs after transfection with siRNA to ATM. Panel (i) shows a graphical description of DNA damage as measured by Comet assay. The Y axis represents mean comet tail length, a measure of DNA breaks. The black bars represent the EUFA326 cell line and the white bars represent the EUFA326G cell line. For bars 1 and 2 cells were treated with control siRNA to GFP. For bars 3 and 4 cells were treated with siRNA targeting ATM. The SEM is represented for each bar from 100 counts in 2 experiments. Panel (ii) shows a representative field of the 326G cell line treated with ATM siRNA at 72 hrs. Panel (iii) shows a representative field of the 326 cell line treated with ATM siRNA at 72 hrs.

In each case the FA deficient cell lines EUFA326 (FANCG deficient), EUFA426 (FANCC deficient), EUFA6914 (FANCA deficient) lines demonstrated constitutive activation of ATM (FIGS. 3A-C, Lane 1 of each blot) when compared to the isogenic corrected cell lines, EUFA326+FANCG, EUFA426+FANCC, EUFA6914+FANCA (FIGS. 3A-C, Lane 2 of each blot). A baseline level of FANCD2 monoubiquitination confirmed normal FA pathway function in each corrected cell line when compared to the corresponding FA pathway deficient cell line (FIGS. 3A-C, compare Lane 2 to Lane 1 in each blot). The autophosphorylation of Atm at serine 1987 was also studied as a measure of Atm activation in primary MEFS derived from the Fancg deficient versus MEFS taken from Fancg wildtype mice (FIG. 3D). Consistent with the human fibroblast lines, Fancg deficient MEFS had a baseline activation of Atm (FIG. 3D, Lane 2) when compared to Fancg wildtype MEFS (FIG. 3D, Lane 1). A baseline monoubiquitination of Fancd2 was also observed in the Fancg+/+ MEF cells when compared to the Fancg−/− cell line indicating a functional FA pathway in the wildtype cells (FIG. 3D, compare Lane 2 to Lane 1).

To further confirm constitutive activation of ATM in FA cells, an in vitro kinase assay was performed for ATM activity in lysates taken from EUFA326 and EUFA326G cell lines. In keeping with the Western blot data, ATM immunoprecipitated from the FANCG mutant EUFA326 cell line demonstrated increased ATM-mediated phosphorylation of recombinant p53 (FIG. 3E, Lane 1) when compared to the corrected EUFA326G cell line (FIG. 3E, Lane 2).

Next it was asked if the observed ATM activation in FA pathway deficient cells was due to dysregulation of ATM function. ATM is strongly activated by ionizing radiation; therefore the EUFA326 and EUFA326G cells were irradiated with 10 Gys of ionizing radiation and measured ATM auto-phosphorylation by Western blotting (FIG. 3F). In both the FA pathway deficient (EUFA326) and corrected cell line (EUFA326G), irradiation resulted in a marked increase in ATM autophosphorylation, indicating normal ATM activation (compare FIG. 3F, Lanes 1 and 2 with Lanes 3 and 4). Interestingly, the EUFA326 cell line demonstrated more ATM activation than the corrected cell line (compare FIG. 3F, Lanes 3 and 4), supporting the model that ATM can compensate for loss of FA pathway function following DNA damage.

ATM is involved in the response to double strand breaks (DSBs) in DNA. Therefore, it was asked if constitutive ATM activation in FA pathway deficient cells may be required for the repair of spontaneous DNA breaks. To address this question the FANCG deficient EUFA326 and the corrected EUFA326G cell lines were treated with siRNA targeting ATM or a control GFP sequence and performed single cell electrophoresis (Comet assay) on each cell line after 72 hours. The mean length of the Comet tail from each cell line is a measure of the mean number of DNA breaks per cell. With control siRNA the EUFA326 cell line demonstrated a two fold greater number of DNA breaks when compared to the corrected EUFA326G cell line. This is consistent with other studies that have reported that FA pathway deficient cells have a greater amount of spontaneous DNA breakage when compared to FA pathway functional cells. Following treatment with siRNA targeting ATM, the EUFA326 cell line demonstrated a 92.0% increase in DNA breaks compared to the EUFA326G cell line which had a 57.6% increase in DNA breaks. These data indicate that constitutive ATM activation in FA pathway deficient cells is necessary to prevent the accumulation of DNA breaks following endogenous DNA damage.

Example 5

FA Pathway Deficient Cells are Sensitive to the ATM Inhibitor KU55933

Figure 4A:
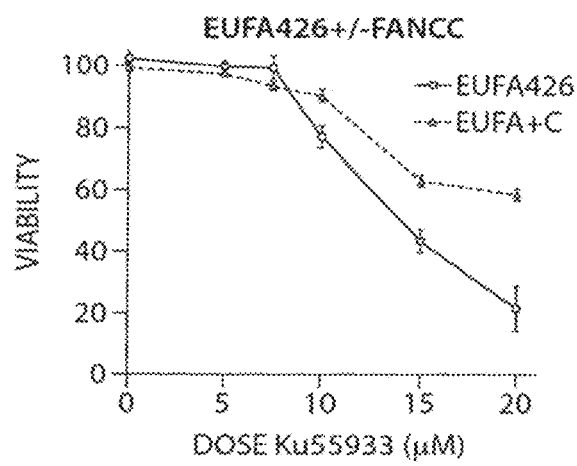
FIG. 4A is a graph showing a 72 hr dose viability curve following treatment with increasing concentrations of KU55933 in FANCC deficient EUFA426 cells.
Figure 4B:
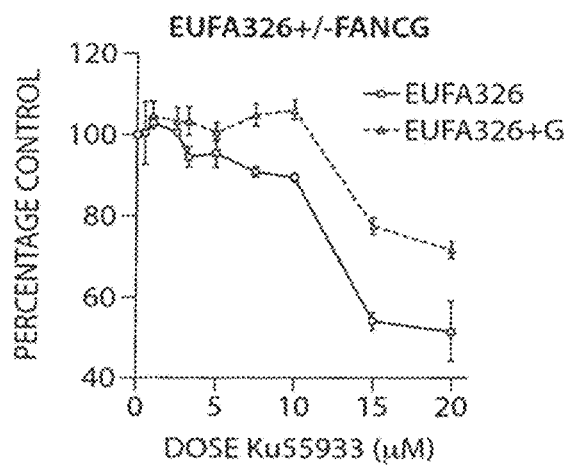
FIG. 4B is a graph showing a 72 hr dose viability curve following treatment with increasing concentrations of KU55933 in FANCG deficient EUFA326 cells.
Figure 4C:
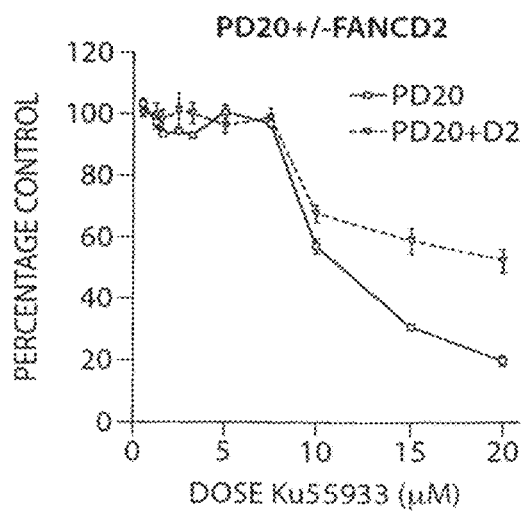
FIG. 4C is a graph showing a 72 hr dose viability curve following treatment with increasing concentrations of KU55933 in FANCD2 deficient PD20 cells.
Figure 4D:
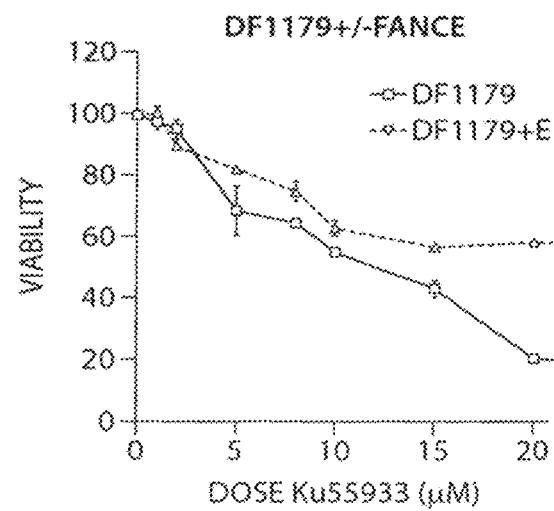
FIG. 4D is a graph showing a 72 hr dose viability curve following treatment with increasing concentrations of KU55933 in FANCE deficient DF1179 cells.
Figure 4E:
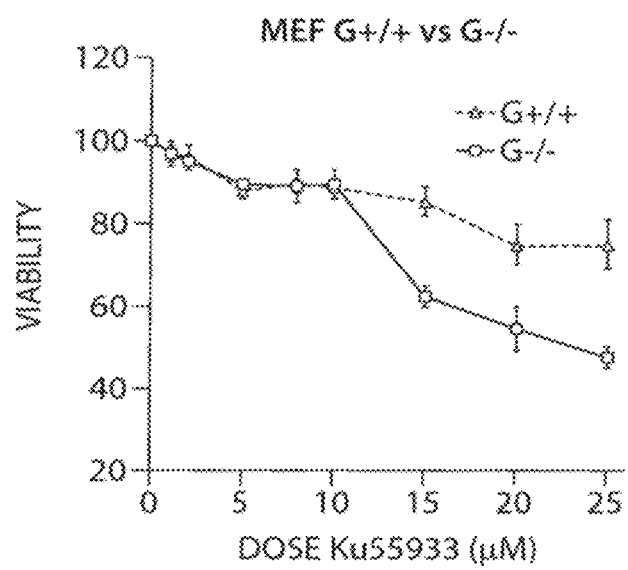
FIG. 4E is a graph showing a 72 hr dose viability curve following treatment with increasing concentrations of KU55933 in Fancg−/− versus Fancg+/+ MEF cells.
Figure 4F:
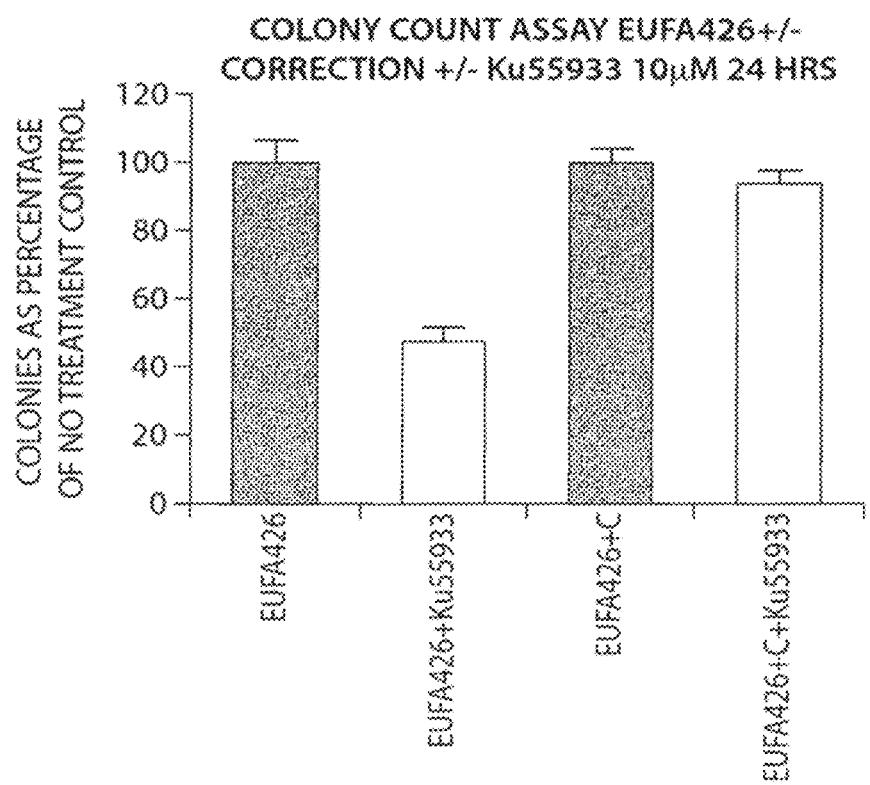
FIG. 4F is a graph showing a 14 day colony count assay comparing the number of colonies in FANCC mutant EUFA426 cells.
Figure 4G:
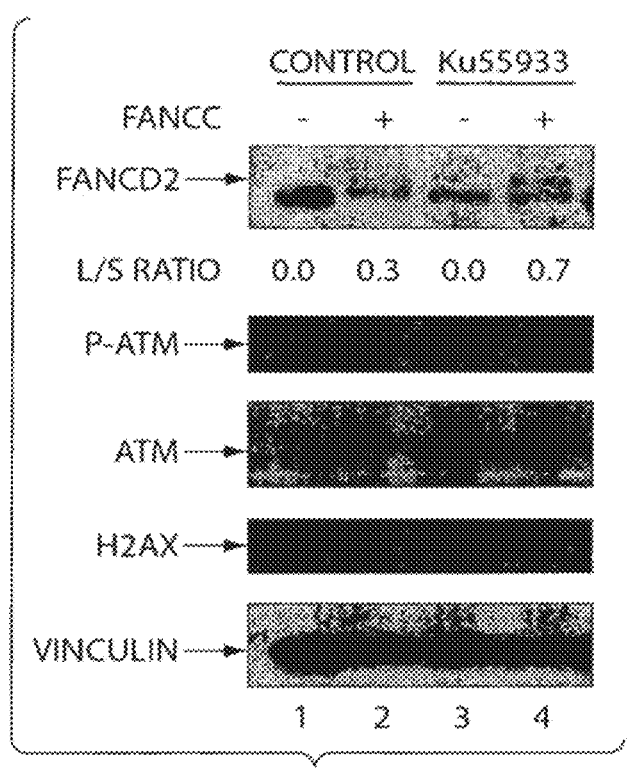
FIG. 4G is a photograph of an immunoblot showing FANCD2 monoubiquitination, ATM autophosphorylation and H2AX phosphorylation in the FANCC mutant EUFA426 cell line.

The compound KU55933 has recently been reported to be a highly specific, competitive ATP binding site inhibitor of ATM (Hickson et al., Cancer Res 64(24): 9152-9159, 2004). In the light of the siRNA data, it was reasoned that FA pathway deficient cells should be selectively sensitive to treatment with this inhibitor. To test this hypothesis, the dose viability curves of isogenic pairs of FA pathway deficient and corrected cell lines treated with increasing doses of KU55933 was compared. FIGS. 4A-4G show that FA pathway deficient cells are selectively sensitive to the ATM inhibitor KU55933. 72 hr dose viability curves (calculated as a percentage of no treatment control) from 3 separate experiments with standard error bars comparing the response to increasing concentrations of KU55933. FIG. 4A shows FANCC deficient EUFA426 cells (solid line) versus an isogenic FA pathway corrected cell line (dotted line). FIG. 4B shows FANCG deficient EUFA326 cells (solid line) versus an isogenic FA pathway corrected cell line (dotted line). FIG. 4C shows FANCD2 deficient PD20 cells (solid line) versus an isogenic FA pathway corrected cell line (dotted line). FIG. 4D shows FANCE deficient DF1179 cells (solid line) versus an isogenic FA pathway corrected cell line (dotted line). FIG. 4E shows Fancg−/− MEF cells (solid line) versus Fancg+/+ MEF cells (dotted line). FIG. 4F shows a 14 day colony count assay comparing the number of colonies in FANCC mutant EUFA426 cells (lanes 1 and 2) versus the isogenic FANCC corrected cell line (lanes 1 and 2). Lanes 1 and 3 represent no treatment controls. Lanes 2 and 4 represent cells treated for 24 hours with 10 μM KU55933 prior to seeding. Colonies counts are represented as a percentage of the untreated control for each cell line. The experiment was repeated three times and the standard error of the mean is represented for each data set. FIG. 4G shows a Western blot comparing FANCD2 monoubiquitination, ATM autophosphorylation and H2AX phosphorylation in the FANCC mutant EUFA426 cell line (lanes 1 and 3) and the isogenic FANCC corrected cell line (lanes 2 and 4). Lanes 1 and 2 represent a no treatment control. Lanes 3 and 4 represent cells treated for 24 hrs with 10 μM KU55933. The sensitivity of FancG−/− MEFs to KU55933 was also tested when compared to wildtype MEFs. In each case, the FA pathway deficient cell line demonstrated increased sensitivity to KU55933. The effective dose range for KU55933 in each case was between 5 μM and 20 μM which corresponded to the previously published concentration range for specific ATM inhibition (Hickson et al., 2004).

To ensure that the observed sensitivity to KU55933 in the FA pathway deficient cells was not assay dependent, colony counts were performed using the FANCC mutant and corrected EUFA426 cell line. This cell line was chosen as it forms distinct colonies when seeded at low density. Each cell line was treated with KU55933 10 μM for 24 hrs and then cells were seeded for colony count assays. After 14 days the FANCC mutant cell line demonstrated an approximately 50% reduction in colonies when compared to the FA pathway proficient EUFA426C cell line (FIG. 4F).

At the same time as EUFA426 and EUFA426C cells were seeded for the colony count assay a proportion were collected for analysis of ATM and FANCD2 activity by Western blotting. Following treatment with KU55933, ATM phosphorylation was no longer observed in the EUFA426 cell line, consistent with complete inhibition (FIG. 4G compare Lanes 1 and 3). Interestingly, H2AX phosphorylation was also decreased, indicating that ATM is primarily responsible for H2AX phosphorylation in FA pathway deficient cells (FIG. 4G compare Lanes 1 and 3). An increase in FANCD2 monoubiquitination in the FA pathway functional EUFA426C cell line was also observed following KU55933 treatment (FIG. 4G, Lane 4) when compared to the no treatment control (FIG. 4G, Lane 2). This result indicates that the FA pathway is activated in following inhibition of ATM activity by KU55933.

Until recently, pharmacological inhibition of ATM was relatively non-specific with drugs such as Wortmanin which also targeted ATR and DNA-PK. Recently, the specific ATM inhibitor KU55933 has been developed and has been reported not to demonstrate these off target effects at effective concentrations (Hickson et al., 2004). It was asked if this drug could be selectively toxic to FA pathway defective cells, thereby offering a possible treatment strategy for FA pathway deficient tumors. In the FA cell lines tested, loss of FA pathway function specifically sensitized the cells to KU55933 suggesting that this compound may have a therapeutic role.

Treatment of FA pathway deficient cells with KU55933 resulted in marked chromosomal breakage when compared to the corrected cell line. These chromosomal breaks most likely represent the persistence of DS DNA breaks that have not been repaired during S phase. Interestingly, there was no evidence of chromosomal breaks in the FA pathway proficient cell line suggesting that either the FA pathway repaired the forks efficiently without DS DNA breakage thereby negating the requirement for ATM or the FA pathway was able to repair DS DNA breaks independent of ATM. In support of the second hypothesis, increased activity of the FA pathway was observed in FA pathway competent cells following KU55933 treatment, as measured by increased FANCD2 monoubiquitination.

Together these data demonstrate the specificity of KU55933-mediated cytotoxicity to cells deficient in the FA pathway. As regards to cancer therapy, this is encouraging as it displays a potential therapeutic window between normal cells and cancer cells for ATM inhibitors. Moreover, the identification of loss of FANCD2 monoubiquitination or the presence of constitutive ATM activation in tumor tissue may represent useful biomarkers to select patients for this type of treatment.

Example 6

KU55933 Treatment Results in Chromosomal Breakage and Cell Death in FA Pathway Deficient Cells Since ATM primarily responds to double strand DNA breaks and the aforementioned data indicated a requirement in FA pathway deficient cells, it was hypothesized that these cells may demonstrate chromosomal breakage following treatment with KU55933. To test this, the FANCE mutant (EUFA1179) and corrected (EUFA1179E) lymphoblast cell lines were used. The FANCE corrected cell line EUFA1179 demonstrates complete correction of mitomycin C induced chromosomal breakage when compared to the FANCE mutant EUFA1179 cell line indicating a complete correction of the FA pathway. Therefore, these cell lines were ideal to measure the effect of FA pathway status on genomic stability following KU55933 treatment.

Figure 5A:
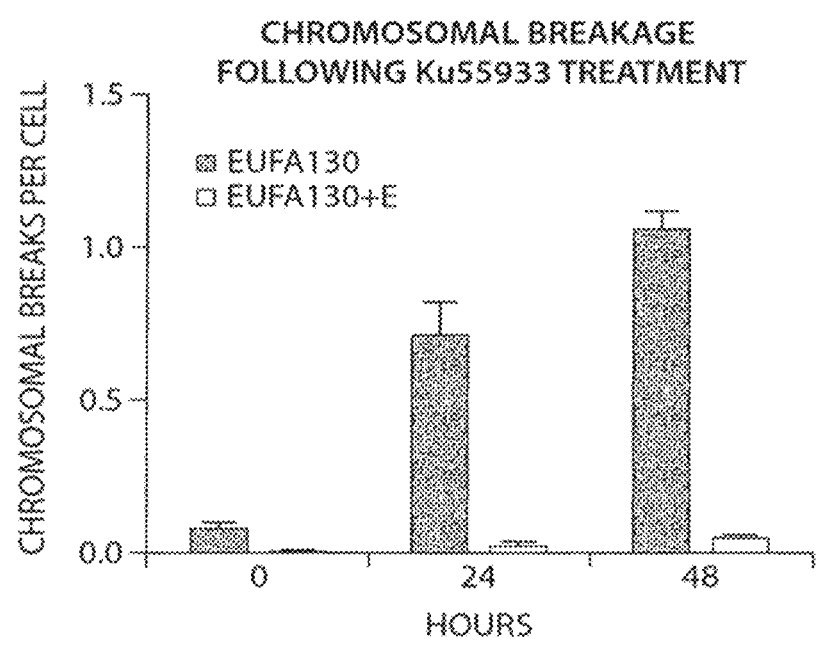
FIG. 5A is a graph showing the number of chromosomal breaks per cell as measured on a metaphase spread 0, 24 and 48 hrs after treatment with KU55933.
Figure 5B:
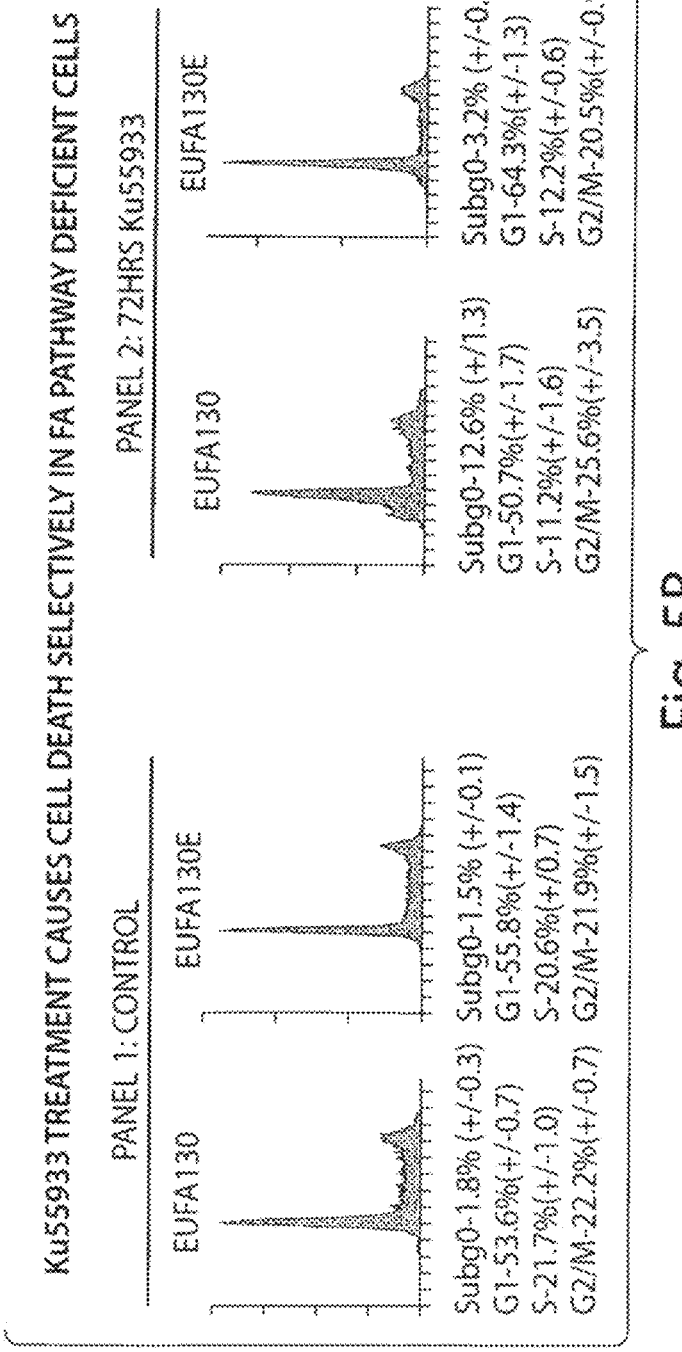
FIG. 5B is a representation of propidium iodide flow cytometry demonstrating the cell cycle profile of the FANCE deficient EUFA130 cell line before and after treatment with KU55933.
Figure 5C:
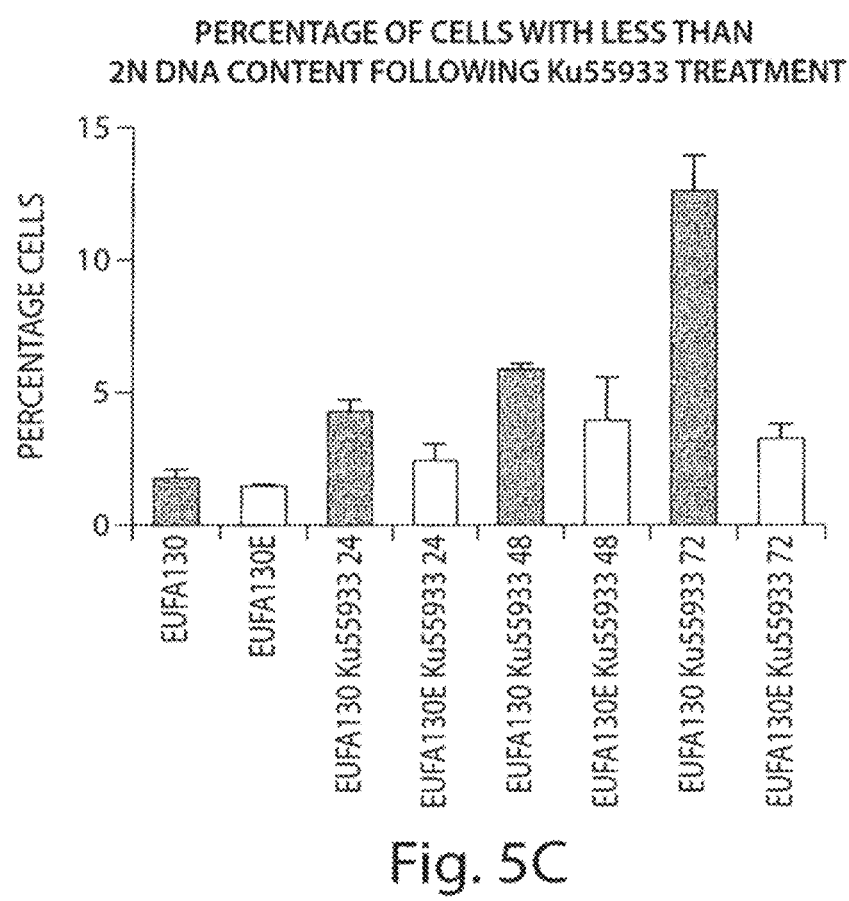
FIG. 5C is a graph showing the representation of cells containing less than 2N DNA (sub G0 population) at 0, 24, 48 and 72 hrs after KU55933.

FIGS. 5A-5C show that KU55933 treatment results in selective Chromosomal breakage and cell death in FA pathway deficient cells. FIG. 5A shows a graphical representation of the number of chromosomal breaks per cell as measured on a metaphase spread 0, 24 and 48 hrs after treatment with 20 µM KU55933. The black bars represent the FANCE deficient EUFA130 cell line. The white bars represent the isogenic FANCE corrected cell line. Mean values were calculated from 3 separate experiments and the SEM is represented for each bar. FIG. 5B shows propidium iodide flow cytometry demonstrating the cell cycle profile of the FANCE deficient EUFA130 cell line versus the isogenic FANCE corrected cell line prior to treatment (panel 1) and 72 hrs after 20 µM KU55933 (panel 2). Mean percentages were calculated from 3 independent experiments and the SEM is given for each value. FIG. 5C shows a graphical representation of cells containing less than 2N DNA (sub G0 population) at 0, 24, 48 and 72 hrs after KU55933. The black bars represent the FANCE deficient EUFA130 cell line. The white bars represent the isogenic FANCE corrected cell line. Mean percentages were calculated for 3 separate experiments and the SEM is represented for each bar.

Each cell line was treated with 20 µM KU55933 for 24 and 48 hrs and chromosomal breakage was assessed by microscopy on metaphase spreads (FIG. 5A). Prior to treatment, a small but significantly greater number of chromosomal breaks per cell were observed in the EUFA1179 cell line when compared to the corrected EUFA1179E cell line (0.080 (SEM 0.02) compared to (0.005 (SEM 0.005)), consistent with the spontaneous chromosomal damage previously reported for FA cells. After 24 hrs and 48 hrs of KU55933 treatment the EUFA1179 cell line demonstrated a 9 fold (0.710 (SEM 0.110)) and 12 fold (1.060 (SEM 0.060)) increase in chromosomal breaks per cell whereas the EUFA1179E cell line had no significant change in chromosomal breakage from baseline.

Next, it was asked if KU55933 could be exerting its selective toxicity in FA pathway deficient cells through cell cycle effects. The EUFA130 and EUFA130E cell lines are useful for cell cycle analysis as they have comparable profiles at baseline (FIG. 5B, Panel 1). Each cell line was treated with KU55933 and the cell cycle profile was measured at 24, 48 and 72 hrs using propidium iodide flow cytometry. At 24 hours each cell line demonstrated a similar, modest, accumulation in the G1 phase. However at later time points the FANCE mutant EUFA130 cell line demonstrated an increased accumulation of cells with less than 2N DNA content (a sub G0 population) when compared to the EUFA130E cell line (the 72 hour time point is shown in FIG. 5B, Panel 2). This sub G0 population represents cell death and is shown graphically at 24, 48 and 72 hrs following Ku55933 treatment in the EUFA130 and EUFA130E cell lines (FIG. 4C). At each time point, the FA pathway deficient EUFA130 cell line demonstrated significantly more cell death than the EUFA130E cell line. Together, these data indicate that inhibition of ATM in FA pathway deficient cells results in catastrophic DNA damage consequently leading to cell death.

Example 7

Relationship Between ATM and the FA Pathway

Figure 6A:
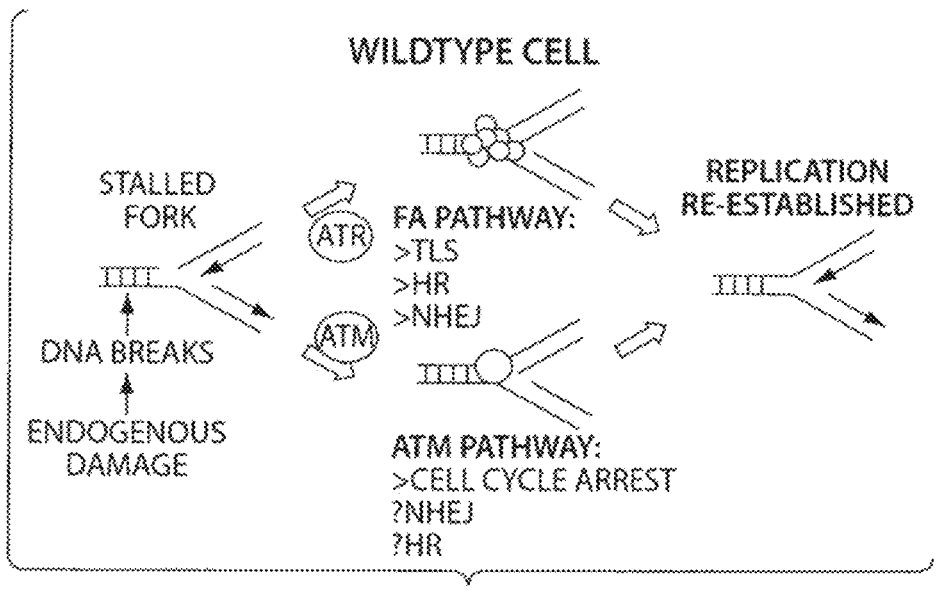
FIG. 6A is a schematic representation showing that endogenous DNA damage results in DNA breaks that cause a replication fork to stall and the ATM and ATR repair pathways in a wild type cell.
Figure 6B:
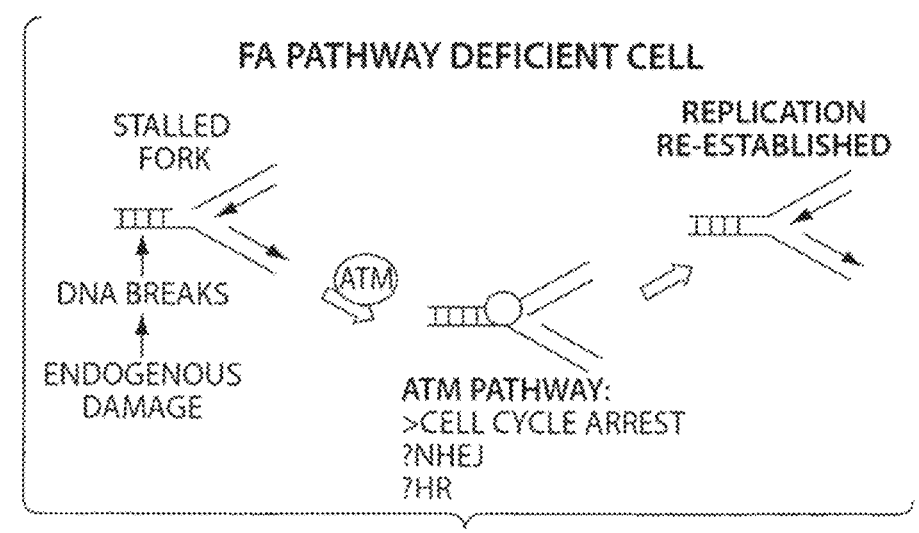
FIG. 6B is a schematic representation showing that in the absence of a functional FA pathway the cell is reliant on the ATM-dependent pathway for the repair of stalled replication forks.
Figure 6C:
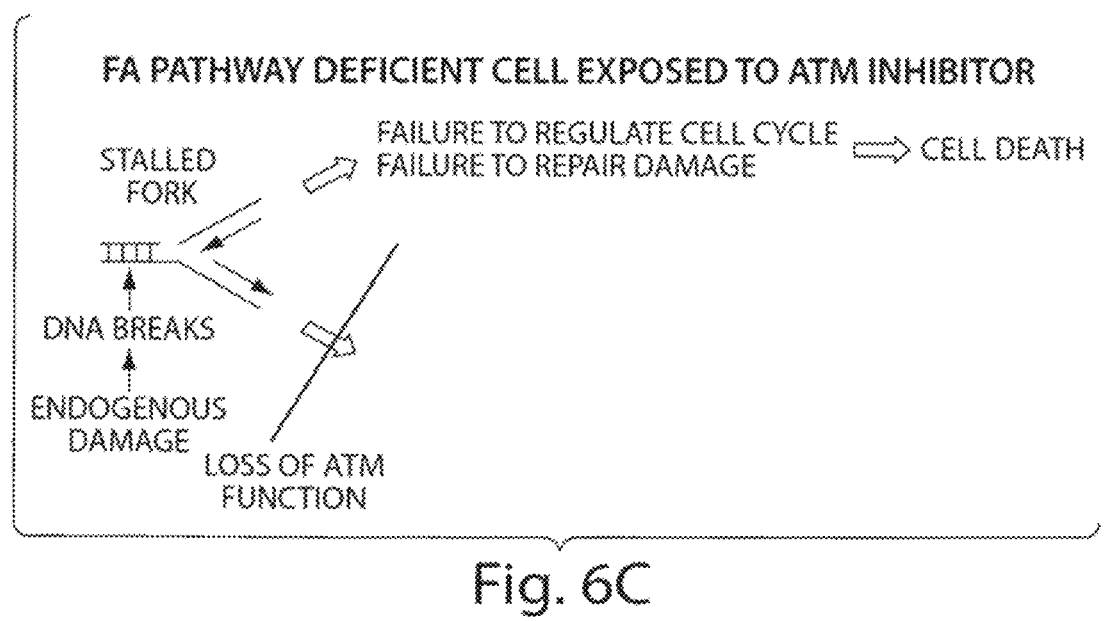
FIG. 6C is a schematic representation showing that if ATM function is lost in a FA pathway deficient cell there is no mechanism to reestablish stalled DNA replication, resulting in catastrophic DNA damage and death.

FIGS. 6A-6C depict a model of how the FA pathway and ATM may compensate for each other following stalled DNA Replication. FIG. 6A shows endogenous DNA damage results in DNA breaks that cause a replication fork to stall. In response to a stalled fork, ATR activates the FA pathway that coordinates DNA repair pathways allowing the reestablishment of DNA synthesis. ATM can also detect double strand DNA breaks at stalled DNA replication forks and can reestablish DNA synthesis independently of the FA pathway, possibly through a role in cell cycle regulation and DNA repair. FIG. 6B shows in the absence of a functional FA pathway the cell is reliant on the ATM-dependent pathway for the repair of stalled replication forks. FIG. 6C shows if ATM function is lost in a FA pathway deficient cell there is no mechanism to reestablish stalled DNA replication, resulting in catastrophic DNA damage and death.

FIG. 6A represents normal cells in which endogenous damage results in DNA breaks, which cause a DNA replication fork to stall which activates ATR and then the FA pathway. The FA pathway in turn, stabilizes and coordinates repair of the fork. An alternative ATM-mediated pathway also exists. In this pathway, ATM detects a DS DNA break at the stalled fork and phosphorylates mediator proteins that result in cell cycle arrest and repair. FIG. 6B represents the sequence of events in FA pathway deficient cells. In these cells stalled forks are primarily repaired through an ATM-dependent pathway. Although the exact role for ATM in the response to a stalled DNA replication fork is unclear, it may activate DNA damage response checkpoints that allow time for efficient repair through homologous recombination or non-homologous end-joining. Recent data also suggest that ATM may have a direct signaling role to NHEJ through phosphorylation of Artemis (Riballo et al., Mol Cell 16(5): 715-724, 2004). Interestingly FA pathway deficient cells displayed increased H2AX phosphorylation (FIG. 4G, Lane 1) compared to corrected cells (FIG. 4G, Lane 2). KU55933 inhibited this H2AX phosphorylation (FIG. 4G, Lane 3). H2AX can be phosphorylated by ATM, ATR and DNA-PK. The data indicate that ATM is primarily involved in H2AX phosphorylation in response to collapsed replication forks in FA pathway deficient cells.

The ATM-mediated pathway may be less efficient in the absence of the FA pathway, accounting for the sporadic chromosomal breaks seen in FA cells, but is sufficient to allow the majority of cells to survive. However the addition of KU55933 to FA pathway deficient cells (FIG. 6C) inhibits the ATM mediated pathway leaving no mechanism of repair for stalled forks. This results in persistent DS DNA breaks, chromosomal damage and ultimately cell death. In the murine model, the death of the ATM FANCG double knockout embryo is predicted to occur very early due to catastrophic DNA damage.

Example 8

Analysis of Fancd2, Pkrdc and Mlh1

Several genetic experiments were carried out following the generation of Fancd2/Pkrdc, Fancd2/Rad52, Fancd2/Mlh1 knockout mice. Both male and female Fancd2−/− mice were infertile and displayed the onset of epithelial tumors at 15-18 months. Slightly decreased birth rate was also observed on some strain backgrounds. Fancd2/Pkrdc mice were not embryonic lethal, showed normal Mendellsian ratios at birth and displayed no striking adult phenotypes.

Figure 7:
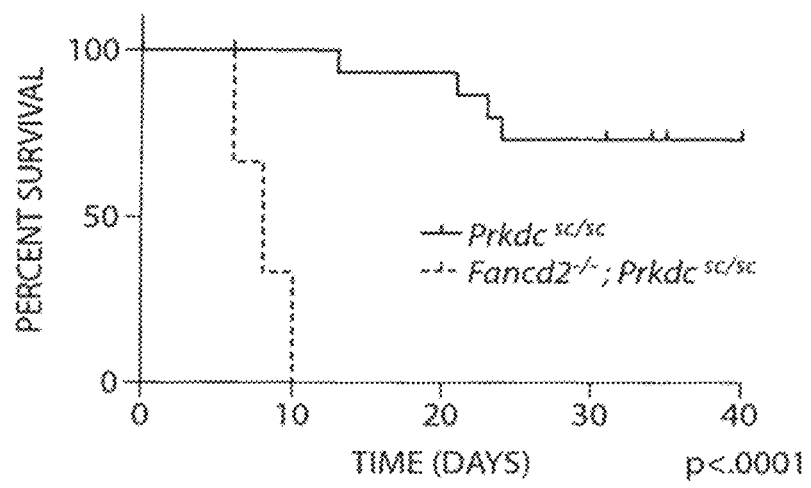
FIG. 7 is a graph showing the percent survival of $Prkdc^{sc/sc}$ and $Fancd2^{-/-}$; $Prkdc^{sc/sc}$ mice following treatment with ionizing radiation.

To further support our findings, double mutant mice were irradiated with 420 rads of ionizing radiation. While only 3 of 11 scid mice died at the same dose, 3 of 3 double mutant mice died very quickly following administration of IR indicating that Fancd2 operates in a pathway distinct from NHEJ in the repair of IR induced DNA damage (FIG. 7). These results indicate that double mutant mice have increased radiosensitivity.

Figure 8:
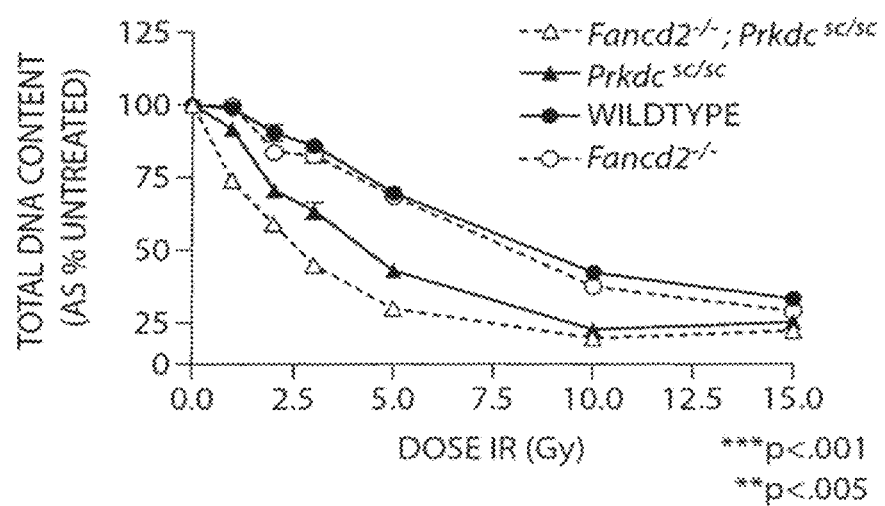
FIG. 8 is a graph showing the total DNA content of Wildtype, $Fancd2^{--}$, $Prkdc^{sc/sc}$ and $Fancd2^{-/-}$; $Prkdc^{sc/sc}$ mice following treatment with ionizing radiation.

To investigate the role of Fancd2 in repair of DSBs, we crossed Fancd2 knockout mice to scid mice. Scid mice have a defect in NHEJ due to a nonsense mutation in the gene encoding the catalytic subunit of DNA-PK, a protein required for NHEJ. Wildtype, Double mutant cells, scid cells, and singly mutant Fancd2 cells were compared in a cell growth assay following increasing doses of IR. While Fancd2 and wt cells are not particularly sensitive to increasing doses of IR scid cells are sensitive (FIG. 8). Interestingly, double mutant cells are more sensitive that scid cells indicating that Fancd2 operates in a DSB response pathway that is distinct from NHEJ.

Figure 9:
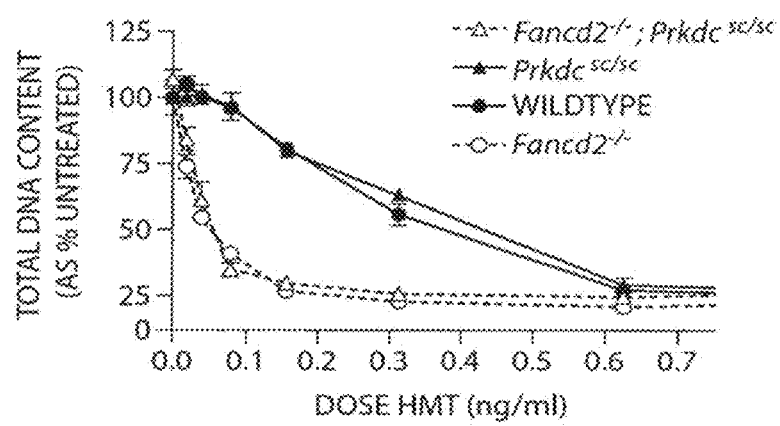
FIG. 9 is a graph showing the total DNA content of Wildtype, Fancd2$^{-/-}$, Prkdc$^{sc/sc}$ and Fancd2$^{-/-}$; Prkdc$^{sc/sc}$ mice following treatment with photoactivated psoralen.

The identical genotypes were exposed to increasing doses of photoactivated psoralen. Scid cells are no more sensitive than wt cells and double mutant cells are equally sensitive as scid cells (FIG. 9). These results indicate that NHEJ plays little to no role in the repair of ICLs.

The results in FIGS. 7-9 show that NHEJ plays little to no role in the repair of ICLs. The results also show that Fancd2 functions in a DNA damage response pathway that is distinct from NHEJ both in vitro and in vivo following IR induced damage; Fancd2 functions in repair of restriction enzyme induced DSBs and Fancd2 may function to control a homologous recombination step, following DSB formation, during ICL repair.

Fancd2/Mlh1 mice were not embryonic lethal, showed normal Mendellian ratios at birth and developed tumors (e.g., intestinal, leukemia) later in life. Fancd2/Mlh1 crossed mice are predicted to yield 1/16 double mutants. However, no double mutants were obtained. Specifically, 73 embryos were harvested and cultured at ED15 with an expected double mutant yield of 6. No double mutants were observed. 40 embryos were harvested and cultured at ED12 and no double mutants were observed.

Figure 10:
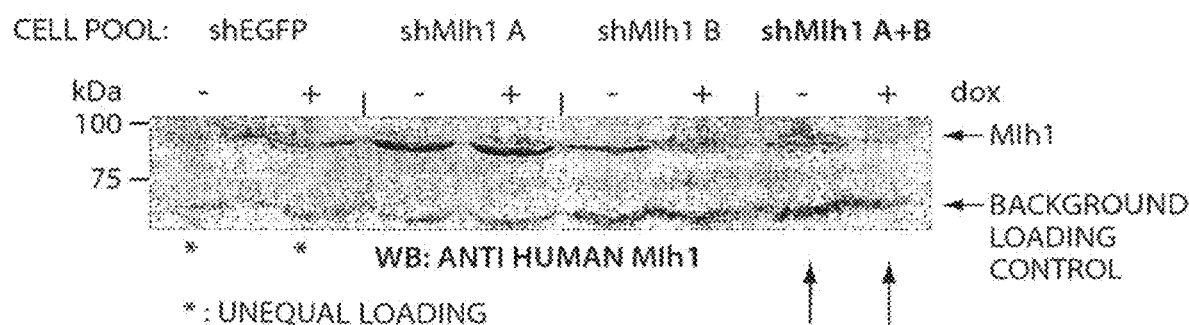
FIG. 10 is a photograph of an immunoblot showing the expression of Mlh1 in human FA-A fibroblasts following treatment with shMlh1 A, shMlh1 B or combinations thereof.
Figure 11:
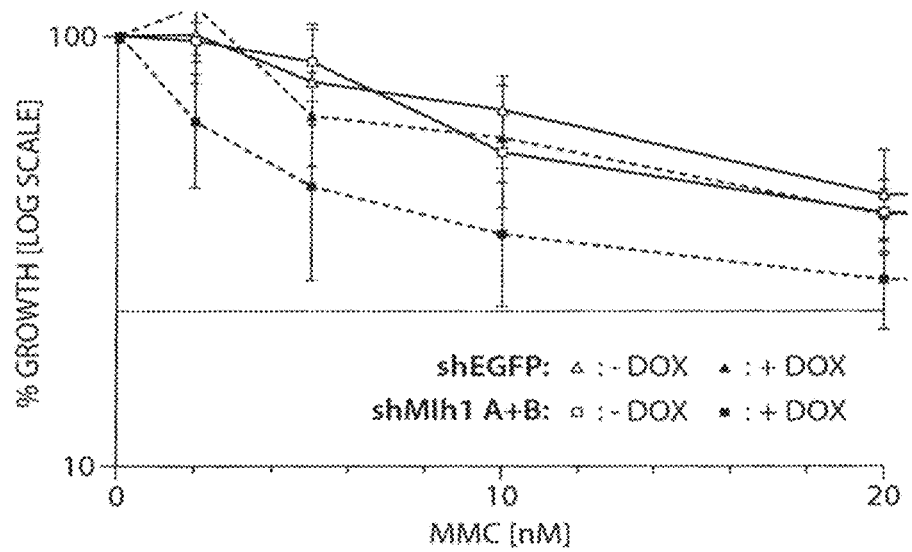
FIG. 11 is a graph showing the decreased growth of cells treated with the combination of shMlh1 A and shMlh1 B following DOX treatment.
Figure 12:
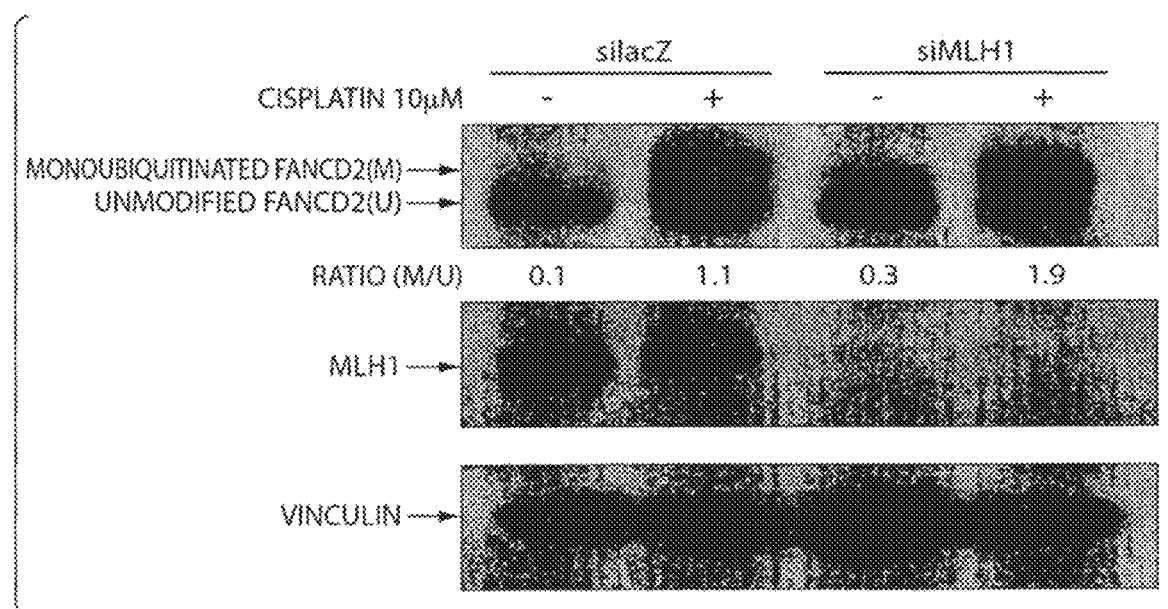
FIG. 12 is a photograph of an immunoblot showing the expression of Mlh1 and the ubiquitination of FANCD2 in HeLa cells transfected with Mlh1 siRNA and following treatment with or without cisplatin.
Figure 13:
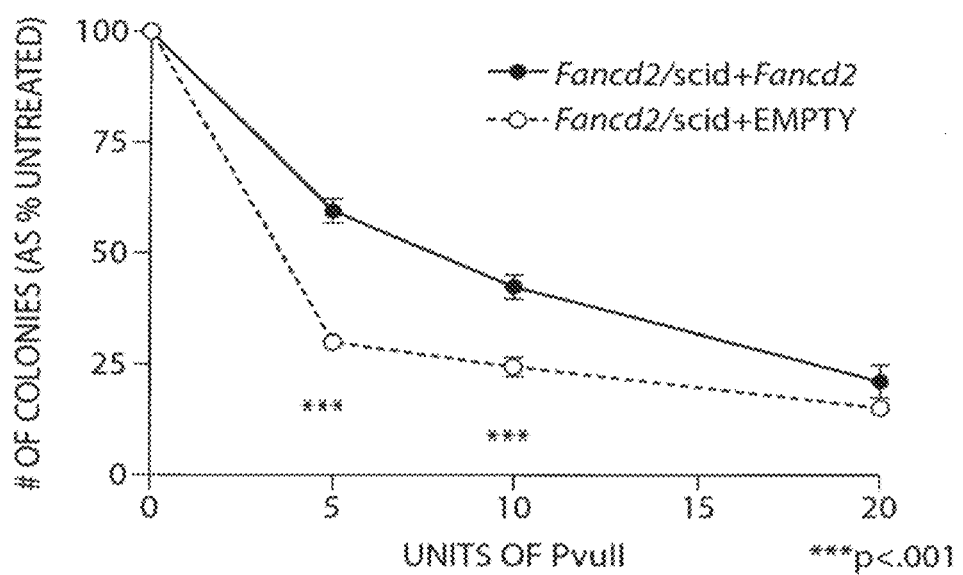
FIG. 13 is a graph showing the number of colonies formed in double mutant cells following retroviral correction with Fancd2 cDNA with PVUII.
Figure 14:
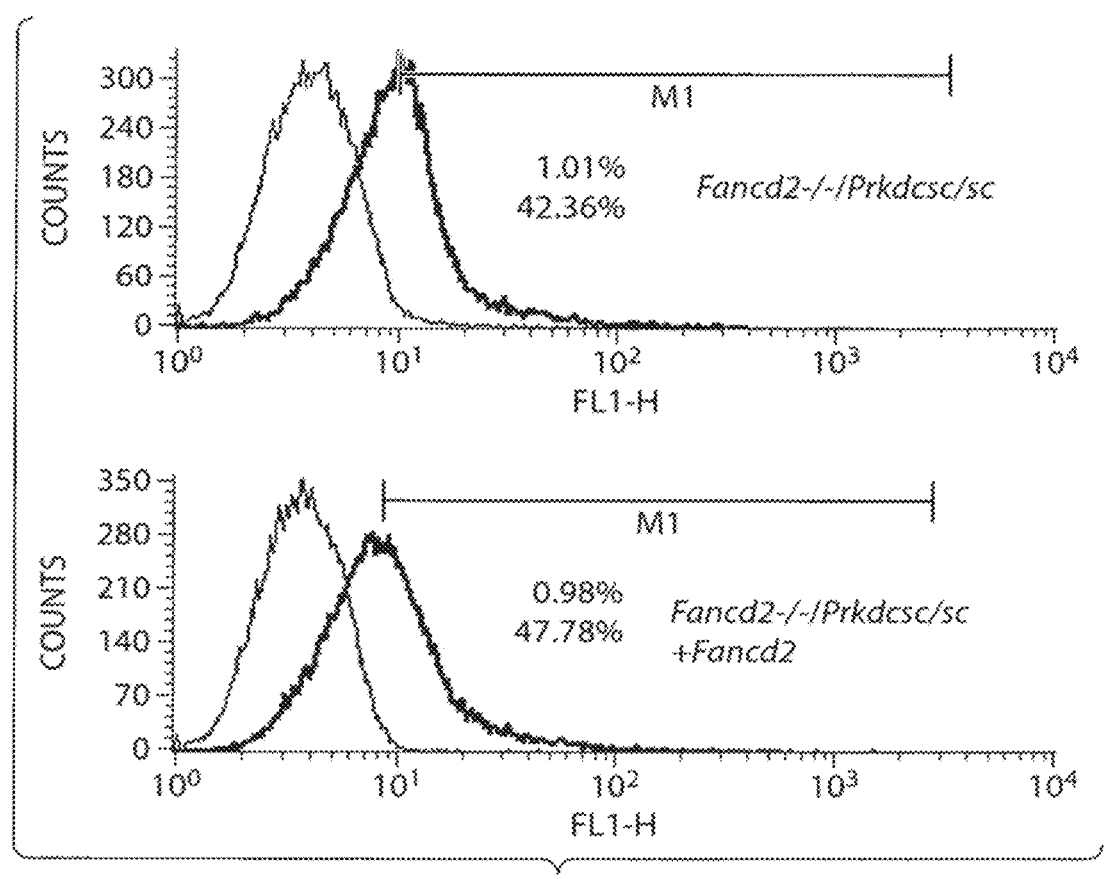
FIG. 14 is a representation of a FACS analysis demonstrating that the decreased colony forming ability of double mutant cells following retroviral correction with Fancd2 cDNA with PVUII is not the result of increased protein uptake in non corrected cells.

Inducible knockdown of Mlh1 was carried out in human FA-A fibroblasts and DOX induced expression of shRNA (shMlh1 A and shMlh1 B or combinations thereof) was examined. The immunoblot results in FIG. 10 show that the combination of shMlh1 A and shMlh1 B efficiently silences Mlh1 protein expression. FIG. 11 graphically shows the decreased growth of cells treated with the combination of shMlh1 A and shMlh1 B following DOX treatment in a 96 well proliferation assay (n=4). To further assess the role of Mlh1, HeLa cells were transfected with Mlh1 siRNA for 72 hours and then treated with or without 10 µM cisplatin for 24 hours (FIG. 12). These results show the monoubiquination of Fancd2 following Mlh1 siRNA induction and Cisplatin treatment. Because IR induces a variety of DNA damage, double mutant and double mutant cells retrovirally corrected with Fancd2 cDNA with PVUII were electroporated. PVUII is a restriction enzyme that causes blunt ended DSBs. This colony forming assay demonstrates that double mutant cells have a reduced colony forming ability (FIG. 13). As a control for the ability of the cells to uptake protein, both genotypes were electroporated with GFP. As shown by FACS analysis in FIG. 14, both genotypes are roughly equivalent in their ability to uptake GFP indicating that the decreased colony forming ability following PvuII electorporation is not due to increased protein uptake in non corrected cells.

The results in FIGS. 10-14 indicate that Mlh1 mediated S-phase checkpoint is required for survival of FA mutant cells. This may be the result of Atm-mediated phosphorylation of Mlh1. However, p53 deletion also abrogates the check-point but is not a synthetic lethal. The results also indicate that the inability to suppress recombination results in mitotic catastrophe (deletions, translocations etc.). Fancd2/Mlh1 double mutants are an early embryonic lethal and the Fancd2−/−/Mlh1+/− and Fancd2+/−/Mlh1−/− are underrepresented. Inducible knockdown of Mlh1 in FANCA fibroblasts has been shown to significantly enhances MMC sensitivity. This result is significant. Since 20-25% of human colon cancers have microsatellite instability due to silencing of Mlh1, inhibitors of the FA pathway may target colon tumors specifically.

Example 9

Phosphorylation of FANCE on Two Conserved Sites is Required for MMC Resistance

Figures 19A, 19B:
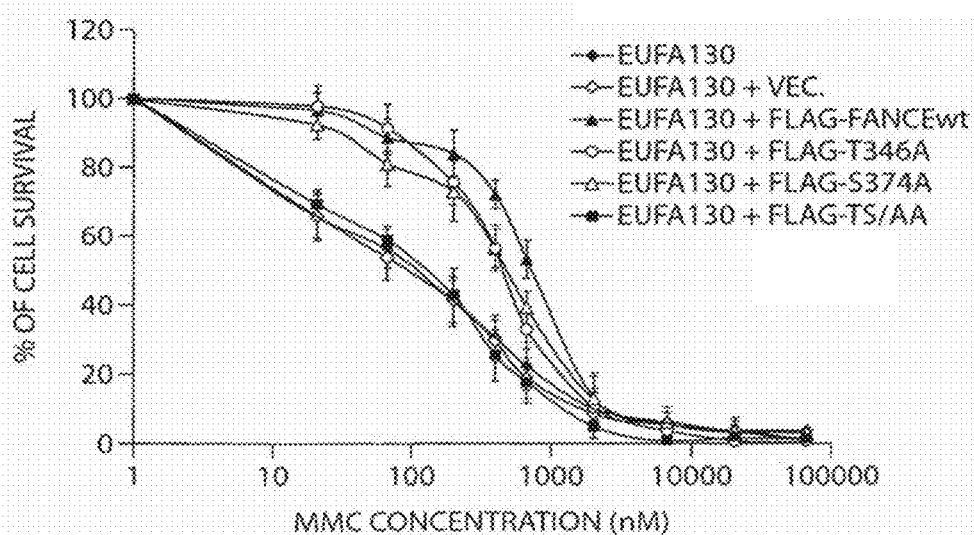
FIG. 19A is schematic of an alignment of sequences surrounding the phosphorylation motif for Chk1 (R-X-X-S/T) in human FANCE with FANCE sequences in other organisms: human (SEQ ID NO: 8), Mouse (SEQ ID NO: 9), Rat (SEQ ID NO: 10), Dog (SEQ ID NO: 11), Cattle (SEQ ID NO: 12), Chicken (SEQ ID NO: 13), Pufferfish (SEQ ID NO: 14), and Zebrafish (SEQ ID NO: 15).
FIG. 19B is a line graph showing somplementation of MMC sensitivity of an FA-E lymphoblast cell line, EUFA130, with empty vector (pMMP), pMMP-FLAG-FANCE, pMMP-FLAG-T346A, pMMP-FLAG-S374A, pMMP-FLAG-TS/AA (the double mutant of T346A, S374A). The indicated retroviral supernatants were generated and used to transduce EUFA130 cells. Puromycin-resistant cells were selected, and Mitomycin C (MMC) sensitivity was determined as described in "Materials and Methods". The values shown are the mean±standard deviation (SD) from four separate experiments.

To examine the role of Chk1 in the FA/BRCA pathway, the primary amino acid sequence of the eleven FA proteins were scanned (A, B, C, D1, D2, E, F, G, L, M, J) for the Chk1 phosphorylation consensus sequence (−7(Leu/Arg)−6 (Xaa)−(Leu/hydrophobic/Arg)−4(basic/Val)−3(Arg/Lys)−2 (Tyr/Xaa)−1(Xaa) Ser+1(Phe/Met/hydrophobic). Two highly conserved phosphorylation sites were identified in the carboxy terminal region of the FANCE protein, Thr346 and Ser374 (FIG. 19A). To determine the functional relevance of these putative phosphorylation sites, each site, was mutated either individually or in combination, within the full length FANCE protein. Patient-derived FA-E cell lines, EUFA130 lymphoblasts and DF1179 fibroblasts, were retrovirally transduced with the cDNA encoding either wild-type FANCE (FLAG-FANCEwt), mutants FANCE (FLAG-T346A or FLAG-S374A), or the double point mutant FANCE (FLAG-TS/AA) (FIG. 19B), (FIGS. 25A-25D). While cells expressing FLAG-FANCEwt were MMC resistant, cells expressing the double mutant FANCE (FLAG-TS/AA) remained hypersensitive to MMC. Cells expressing the single point mutants of FANCE exhibited less MMC sensitivity (FIG. 19B).

The ability of the FANCE mutant proteins to restore FANCD2 monoubiquitination was examined (FIG. 19C). As previously described FLAG-FANCEwt restored FANCD2 monoubiquitination (FIG. 19C, lanes 6-10), and DNA damage generated by IR further activated FANCD2 monoubiquitination. The double mutant FANCE (FLAG-TS/AA) also restored monoubiquitination of FANCD2. Cells expressing the double mutant FANCE (FLAG-TS/AA) had elevated basal levels of FANCD2 monoubiquitination (FIG. 19C, compare lanes 11 and 6), and failed to exhibit further FANCD2 monoubiquitination following DNA damage (FIG. 19C, lanes 11-15).

The assembly of FANCD2 nuclear foci in the FA-E cells expressing the double mutant FANCE (FLAG-TS/AA) (FIG. 19 D,E) was determined. Both wild-type and the double mutant (FLAG-TS/AA) of FANCE restored FANCD2 foci formation (FIG. 19 D). Cells expressing the double mutant of FANCE protein (FLAG-TS/AA) had increased basal levels of FANCD2 foci, and failed to upregulate FANCD2 foci after DNA damage (FIG. 19E), thus correlating with FANCD2 monoubiquitination levels (by Western blot, FIG. 19 C). Taken together, these results suggest that phosphorylation of Thr346 and Ser374 on FANCE is not required for FANCD2 monoubiquitination and foci formation, but is required for MMC resistance.

Example 10

Phosphorylation of FANCE by Chk1 In Vitro and In Vivo

To demonstrate whether Chk1 directly phosphorylates FANCE, phosphorylation of the two highly conserved threonine and serine residues by Chk1 in vitro was examined. Glutathione S-transferase (GST) peptide fusion proteins containing different regions of FANCE (FIG. 20A, left panel) were generated. Three GST peptide fusion proteins, (332-365) WT, (349-382) WT and (332-382) WT containing either Thr346 or Ser374 or both residues, but not the GST fusion proteins with Thr to Ala or Ser to Ala single or double mutations, were phosphorylated by Chk1 in vitro. (FIG. 20A, right panel).

To further study the phosphorylation of FANCE on T346 and S374 by Chk1, rabbit polyclonal antisera were produced against FANCE peptides containing the putative phosphorylated residues, SDLGLLRLCpT(346)WL (anti-pT346) or against LFLGRILpS (374) LTSS (anti-pS374). Purified recombinant wild-type (rFANCEwt) or the double mutant (rTS/AA) of FANCE proteins were incubated with Chk1 or with the two related checkpoint kinases, Chk2 and MAP-KAP2 (MK2) in vitro (FIG. 20B). The anti-phospho-antibodies for FANCE (anti-pT346 and anti-pS374) specifically recognized the recombinant FANCE (rFANCEwt) protein phosphorylated by Chk1 in vitro (FIG. 20B, lane 3). Recombinant FANCE (rFANCEwt) was not phosphorylated by Chk2 or MAPKAP2 in vitro (FIG. 20B, lanes 4 and 5). The specificity of the antibodies was demonstrated by the lack of reactivity with the double mutant protein of FANCE (rTS/AA) and GST (FIG. 20B, lanes 6-15).

Figure 20C:
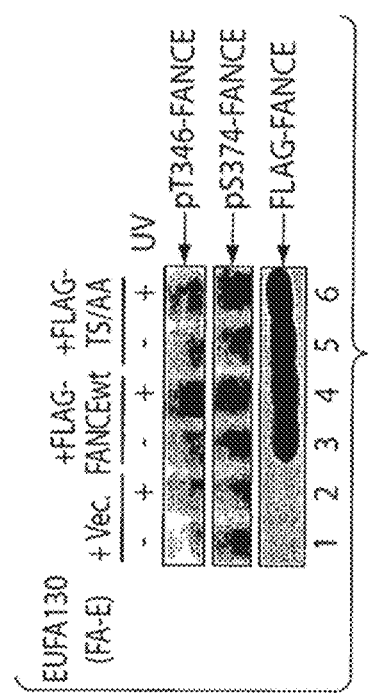
FIG. 20C is a photograph of an immunoblot showing Chk1 phosphorylates FANCE in vivo. EUFA130 (FA-E) lymphoblasts were stably expressed with empty vector, FLAG-FANCEwt, FLAG-TS/AA (the double mutant) as indicated. Cells were either untreated or treated with UV (60 J/m$^2$), after 3 hr, immunoprecipitation was performed using anti-FLAG antibody, and analyzed by SDS-PAGE, followed by Western blot with anti-pT346-FANCE and anti-pS374-FANCE phosphospecific antibodies and anti-FLAG antibody.

It was then determined whether FANCE is phosphorylated in vivo following DNA damage (FIG. 20C). Using the two anti-phospho-antibodies of FANCE (anti-pT346, anti-pS374), FLAG-FANCE immune complexes were immunoblotted from FA-E cells stably expressing wild-type FANCE (FLAG-FANCEwt) or the double mutant (FLAG-TS/AA). Following cellular exposure to UV light, a potent activator of the FA/BRCA pathway, the anti-pT346 and anti-pS374 antisera detected the FANCEwt, but not the double mutant protein (TS/AA). Taken together, these results confirm the specificity of the antibodies and the DNA damage-inducible phosphorylation of these two residues.

Figure 20D:
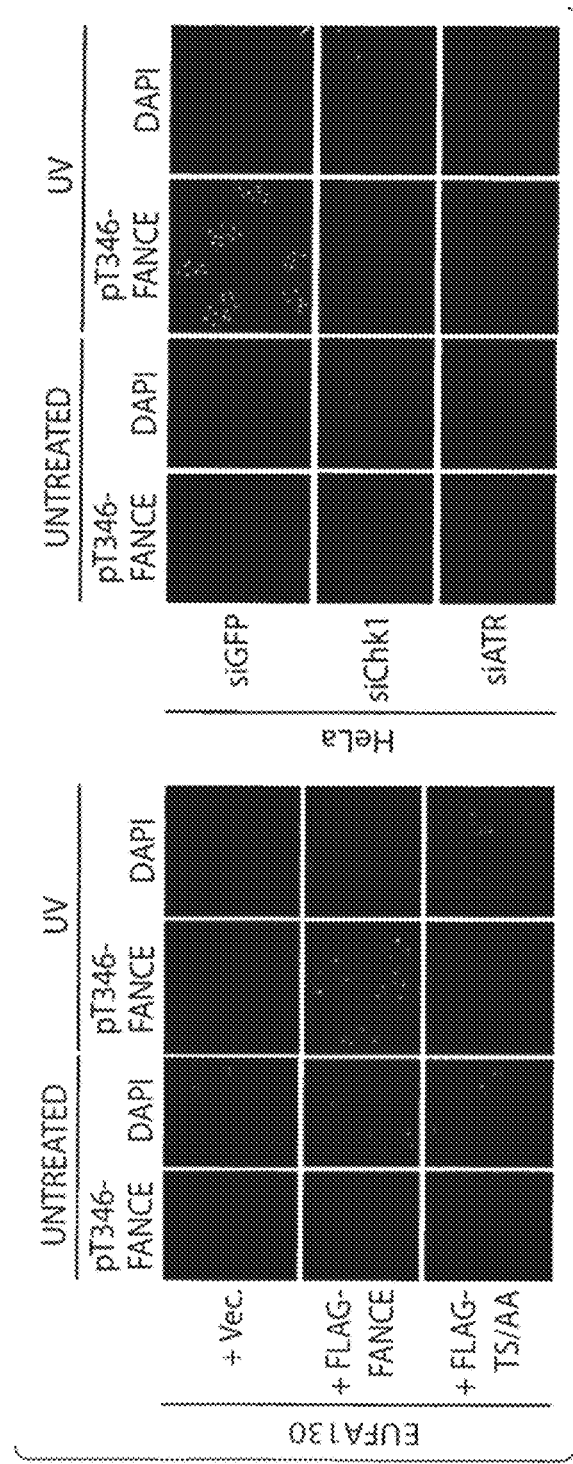
FIG. 20D are photographs of EUFA130 (FA-E) lymphoblasts stably expressing empty vector (EUFA130+Vec.) and FLAG-FANCEwt (EUFA130+FLAG-FANCE) were either untreated or treated with UV (60 J/m$^2$) and fixed two hours later, immunofluorescence was performed using anti-pT346-FANCE antibody (left panel). Magnification, ×630. HeLa cells were transiently transfected with siRNA targeted against GFP (control), Chk1, or ATR. After 72 hr of transfection, cells were either untreated or treated with UV (60 J/m$^2$) and incubated two hours before fixation, immunofluorescence was performed using anti-pT346-FANCE antibody (right panel). Magnification, ×400.
Figure 20E:
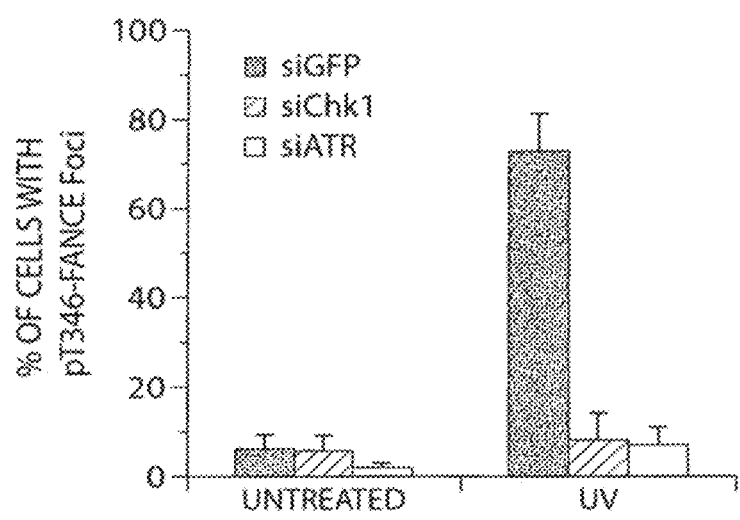
FIG. 20E is a bar chart showing the quantification of pT346-FANCE foci. Cells with more than four distinct foci were counted as positive. 100 cells/sample were analyzed. The values shown are the mean±SD from three separate experiments. The formation of pT346 FANCE foci with the treatment of UV (60 J/m$^2$) was strongly decreased in HeLa cells in which ATR or Chk1 had been suppressed with siRNA.
Figure 26A:
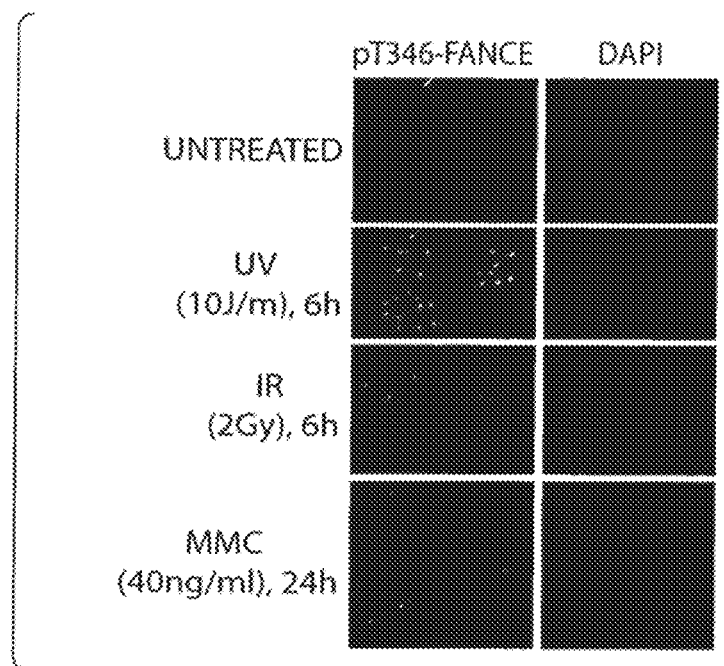
FIGS. 26A-D illustrate phospho-T346-FANCE foci formation in response to DNA damage.
Figure 26B:
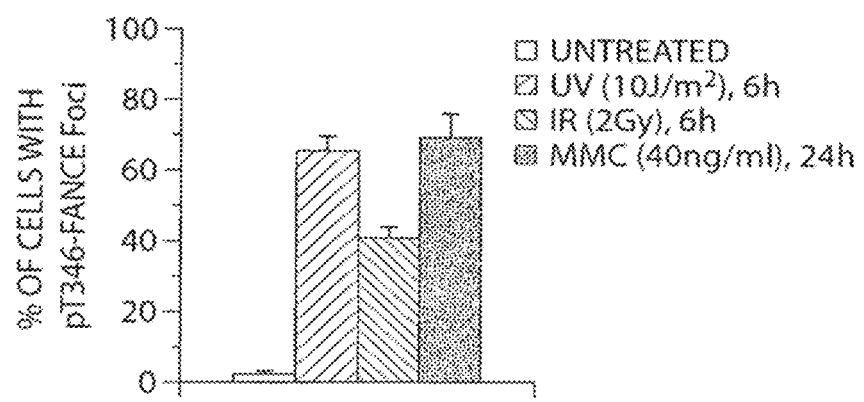
Figure 26C:
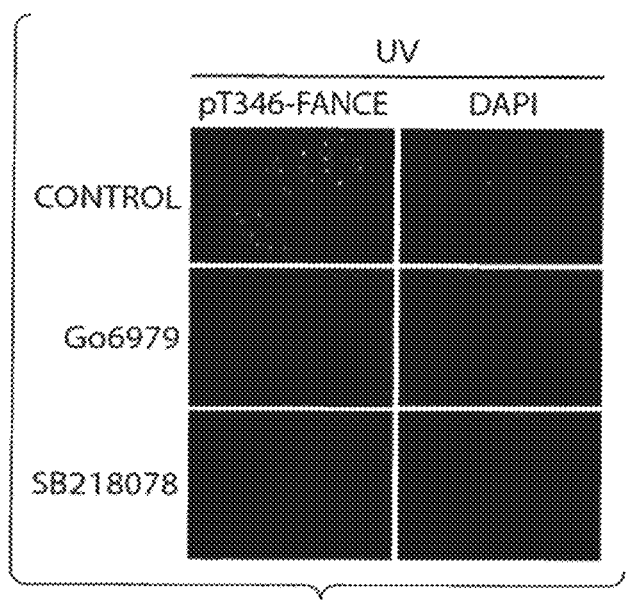
Figure 26D:
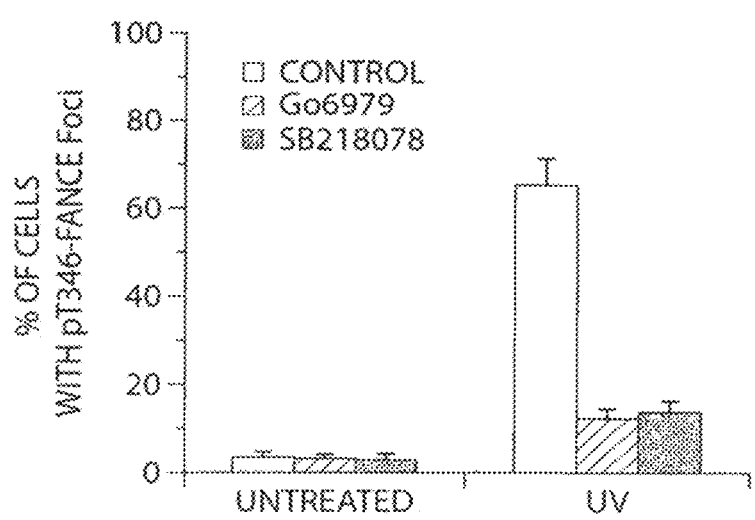

Immunofluorescence was used to demonstrate the in vivo phosphorylation of FANCE by Chk1. The anti-pT346 antiserum detected activated FANCE protein in corrected FA-E lymphoblasts (EUFA130+FLAG-FANCE) after cellular exposure to DNA damage, but not in FA-E cells stably expressing vector and the double mutant (TS/AA) (FIG. 20D, left panel). Interestingly, the phosphorylated FANCE protein, detected by anti-pT346 antibody, assembled in DNA damage-inducible nuclear foci (FIG. 20D, Figure S2, A and B). UV also activated pT346-FANCE foci in HeLa cells, and siRNA directed against ATR or Chk1 decreased the UV-inducible pT346-FANCE foci (FIG. 20D-E). Pretreatment with Chk1 inhibitors (Gö6976 or SB218078) decreased the pT346-FANCE foci formation after UV exposure (FIGS. 26C and 26D).

Example 11

Figure 21A:
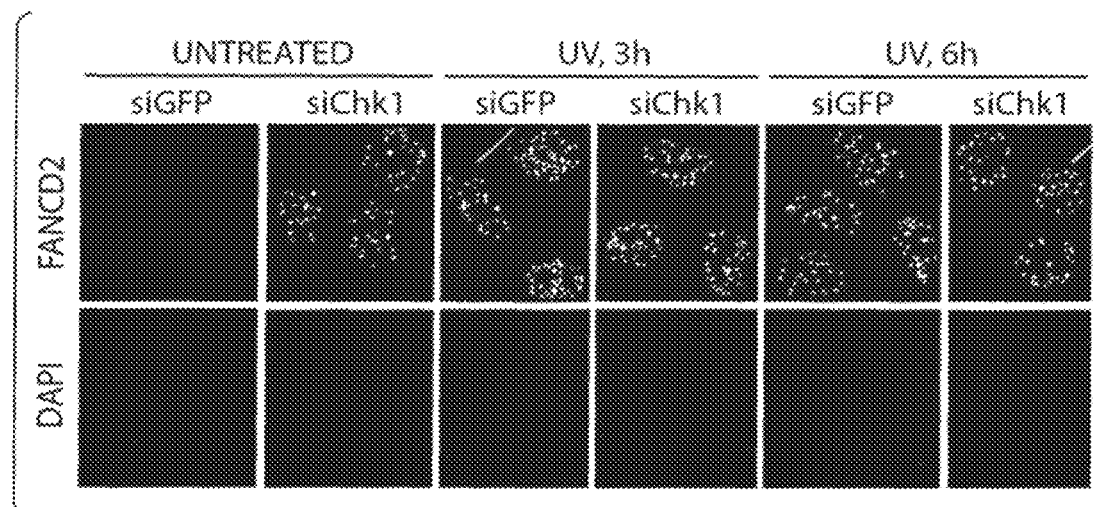
FIG. 21A is a series of photographs showing HeLa cells were transfected with siRNAs targeted against GFP (control) or Chk1. After 72 hr of transfection, cells were treated with UV (60 J/m$^2$) and incubated for 3 hr or 6 hr before fixation and lysis, immunofluorescence was performed using anti-FANCD2 antibody. Magnification, ×400
Figure 21B:
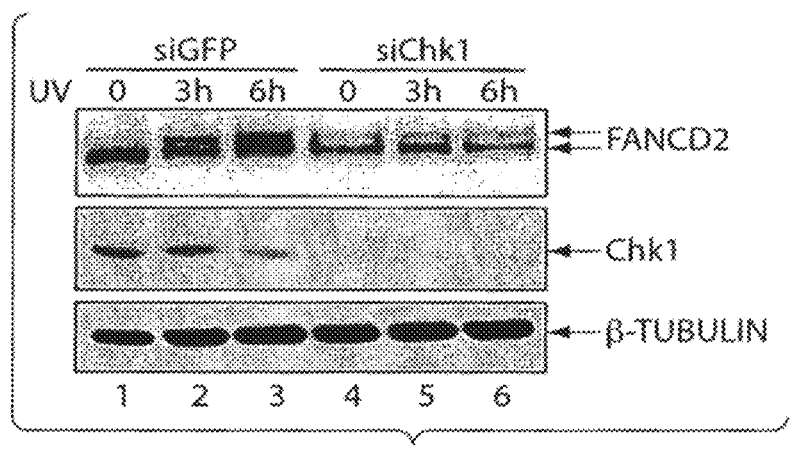
FIG. 21B is a photograph of a Western blot of whole cell extracts Anti-β-Tubulin blot was used as a loading control (B).
Figure 21C:
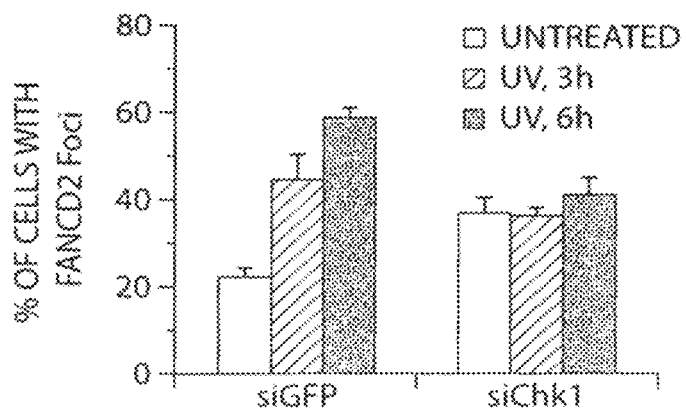
FIG. 21C is a bar chart showing the quantification of FANCD2 foci. Cells with more than four distinct foci were counted as positive. 200 cells/sample were analyzed. The values shown are the mean±SD from three separate experiments.

SiRNA Knockdown of Chk1 Results in an Elevated Basal Level of FANCD2 Monoubiquitination and FANCD2 Foci The effect of siRNA knockdown of Chk1 on FANCD2 monoubiquitination and FANCD2 foci formation after DNA damage was examined (FIGS. 21A-21C). SiRNA knockdown of Chk1 resulted in an elevated basal level of FANCD2 foci formation (FIG. 21A) and FANCD2 monoubiquitination (FIG. 21B, lane 4). Monoubiquitination and nuclear foci formation of FANCD2 were not further increased following DNA damage (FIG. 21B, lanes 4-6 and FIG. 21C). These results indicate that the disruption of Chk1 activity mimics the cellular phenotype of the FANCE(TS/AA) double mutant.

Example 12

Colocalization of FANCD2 Foci and Phospho-T346-FANCE Foci

Figure 22A:
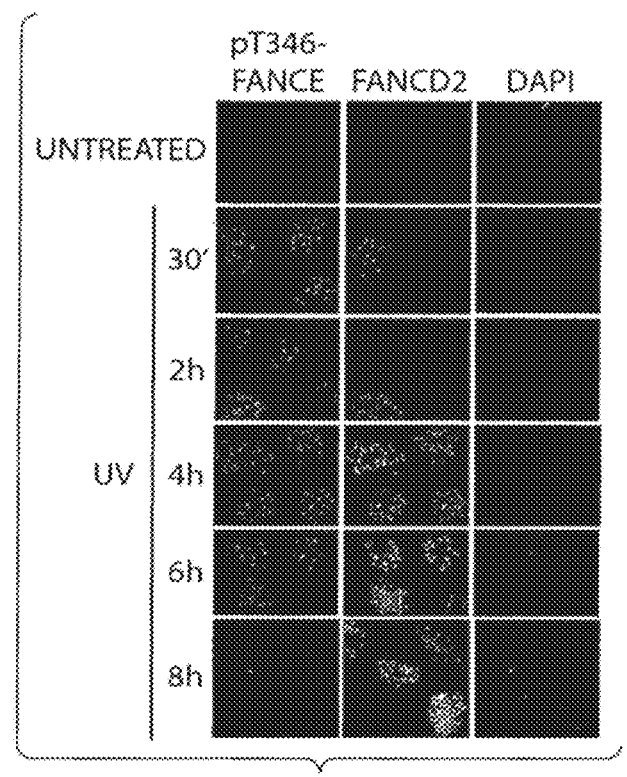
FIG. 22A is a series of photographs showing T\the kinetics of phospho-T346-FANCE foci and FANCD2 foci were followed after DNA damage. HeLa cells were either untreated or treated with UV (60 J/m2) and incubated for different periods of time (30', 2 h, 4 h, 6 h, 8 h) as indicated before fixation, immunofluorescence was performed using anti-pT346-FANCE and anti-FANCD2 (FI-17) antibodies. Magnification, ×400.
Figure 22B:
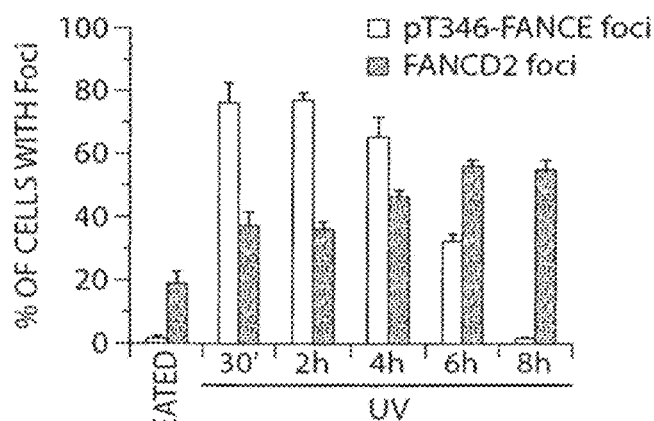
FIG. 22B is a bar chart showing the analysis of cells with more than four distinct foci were counted as positive. 200 cells/sample The values shown are the mean±SD from three separate experiments.
Figure 22C:
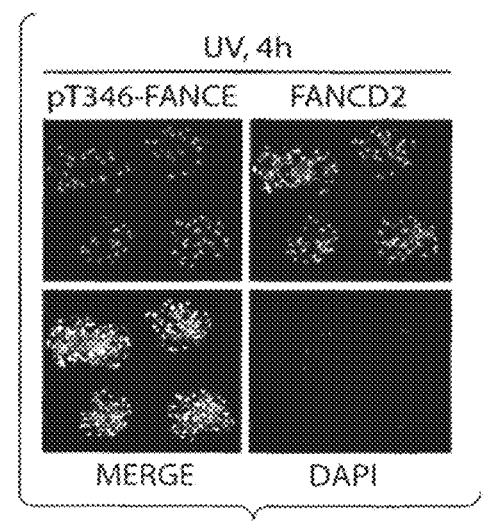
FIG. 22C is a series of photographs after 4 hours of UV irradiation, colocalization of phospho-T346-FANCE foci and FANCD2 foci in HeLa cells i, Magnification, ×630.

The assembly of phospho-T346-FANCE foci and FANCD2 foci following DNA damage was examined (FIGS. 22A-22C). Untreated HeLa cells exhibited no phospho-T346-FANCE foci or FANCD2 foci (FIG. 22A). DNA damage from UV light activated the phosphorylation of FANCE on T346 and foci formation by 30 minutes, and these foci were no longer observed after eight hours. FANCD2 foci began to accumulate at 30 minutes after UV, and peaked at eight hours. The kinetics of phospho-T346-FANCE foci formation and FANCD2 foci formation are shown graphically in FIG. 22B. Double staining revealed that pT346-FANCE foci and FANCD2 foci colocalize (FIG. 22C), but exhibit distinct kinetics (FIG. 22B).

Example 13

Figure 23A:
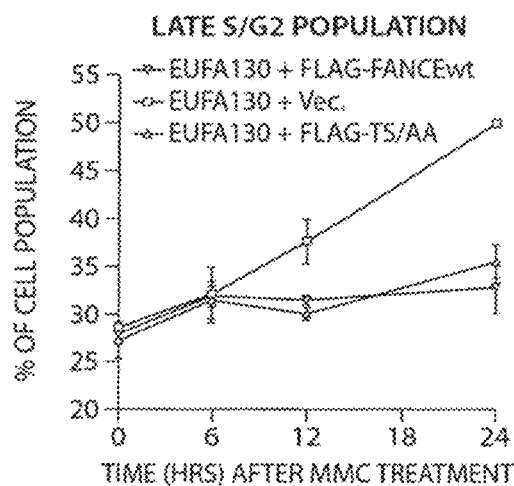
FIG. 23A is a bar chart showing FANCE phosphorylation by Chk1 does not correct MMC-mediated cell death but corrects cell cycle progression and promotes DNA synthesis following MMC treatment. FA-E cells (EUFA130) stably expressing wild-type FANCE (EUFA130+FLAG-FANCEwt) or the double mutant of FANCE (EUFA130+FLAG-TS/AA) do not accumulate in the late S/G2 phase of the cell cycle after 24 hr of MMC treatment when compared to cells stably expressing empty vector (EUFA130+Vec.). The values shown are the mean±SD from three separate experiments.
Figure 23B:
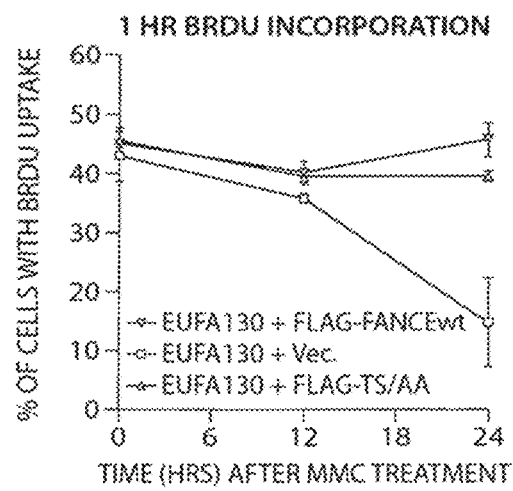
FIG. 23B is a bar chart showing FANCE phosphorylation by Chk1 does not correct MMC-mediated cell death but corrects cell cycle progression and promotes DNA synthesis following MMC treatment. FA-E cells stably expressing empty vector (EUFA130+Vec.) have decreased DNA synthesis after 24 hr of MMC 160 ng/ml treatment when compared to FA-E cells stably expressing wild-type FANCE (EUFA130+FLAG-FANCEwt) or the double mutant of FANCE (EUFA130+FLAG-TS/AA). The values shown are the mean±SD from three separate experiments.

Chk1-Mediated Phosphorylation of FANCE is Required for MMC Resistance but not Required for DNA Replication or Normal Cell Cycle Progression Recent studies indicate that the FA core complex has additional replication and checkpoint activities which are discrete from FANCD2 monoubiquitination. To address whether phosphorylation of FANCE by Chk1 is required for normal S phase progression, we compared the ability of FANCE wild-type (FLAG-FANCEwt) or the double mutant (FLAG-TS/AA) to restore DNA replication and S phase progression (FIGS. 23 A and B). After 24 hours of MMC treatment, FA-E cells (EUFA130), expressing either wild-type FANCE (FLAG-FANCEwt) or the double mutant (FLAG-TS/AA), were equally competent for DNA replication and did not accumulate in the late S and G2 cell cycle phase. As expected, FA-E cells containing the empty vector arrested and accumulated in late S and G2 phase and demonstrated decreased DNA synthesis (FIGS. 23 A and B). Moreover, the double mutant protein (FLAG-TS/AA) stabilized the FA core complex, and restored FANCD2 monoubiquitination (FIG. 19C).

Figure 23C:
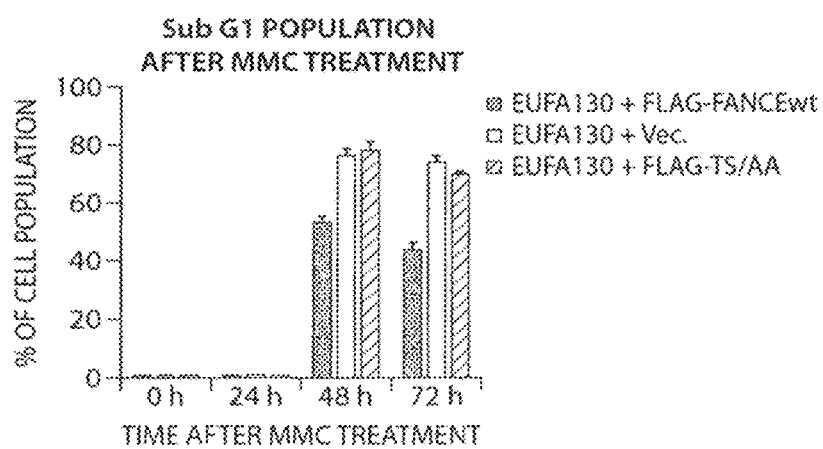
FIG. 23C is a bar chart showing FANCE phosphorylation by Chk1 does not correct MMC-mediated cell death but corrects cell cycle progression and promotes DNA synthesis following MMC treatment. FA-E cells stably expressing the double mutant of FANCE (EUFA130+FLAG-TS/AA) or empty vector (EUFA130+Vec.) demonstrate a higher percentage of sub G1 cells after 48 and 72 hours following MMC (160 ng/ml) treatment when compared to cells expressing wild-type FANCE. Values shown are the mean±SD from three separate experiments.

It was tested whether the double mutant of FANCE could prevent MMC-mediated cell death when expressed in the FA-E cell line. Cell death results in nuclear fragmentation (the sub G1 population), and this was assessed by flow cytometry following MMC treatment. As shown in FIG. 23C, equivalent levels of sub G1 cells were present in FA-E cells stably expressing empty vector and the double mutant of FANCE (FLAG-TS/AA) following MMC treatment. In contrast, FA-E cells corrected with the wild-type FANCE (FLAG-FANCEwt) demonstrated a significantly lower percentage of cells with fragmented nuclei. These results demonstrate that the intact FA core complex containing the double mutant of FANCE (FLAG-TS/AA) can correct the cell cycle abnormalities of FA-E cells but cannot confer resistance to MMC, confirming that Chk1-mediated phosphorylation of FANCE is required for crosslinker resistance (Table 5) (FIG. 22D).

Example 14

Chk1-Mediated Phosphorylation of FANCE Promotes FANCE Degradation

Figure 24A:
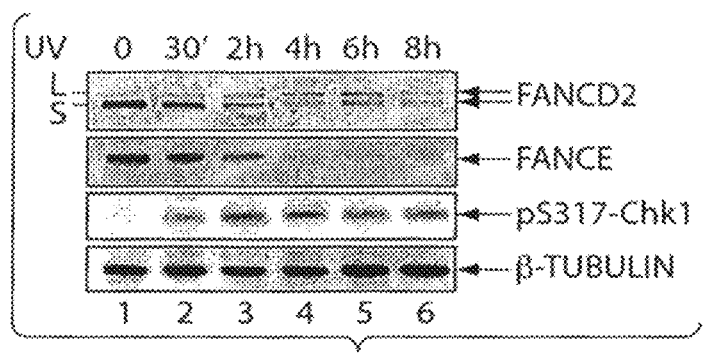
FIG. 24A is a photograph of a Western blot showing FANCE phosphorylation by Chk1 promotes its degradation. HeLa cells were either untreated or treated with UV irradiation at 60 J/m$^2$ and incubated for different periods of time as indicated before lysis. Whole cell extracts were immunoblotted with the indicated antibodies. Anti-β-Tubulin blot was used as a loading control.

The disappearance of phospho-FANCE-T346 foci after DNA damage (FIG. 22A) suggested that FANCE may undergo regulated proteolysis. To test this hypothesis, we examined the cellular levels of FANCE following UV damage (FIG. 24A), After only 30 minutes, Chk1 activation and FANCD2 monoubiquitination were observed (FIG. 24A, lane 2). By four to six hours, FANCD2 monoubiquitination was maximal and FANCE levels decreased (FIG. 24A, lane 4-6), FANCE degradation was also observed in a UV dose dependent manner.

Figure 24B:
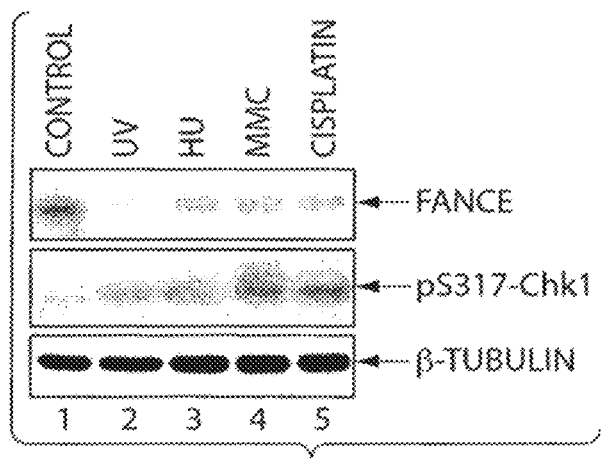
FIG. 24B is a photograph of a Western blot showing FANCE phosphorylation by Chk1 promotes its degradation. HeLa cells were synchronized by double-thymidine block, and then released into S phase. One hour after release, the cells were either untreated (Control) or treated with UV (60 J/m$^2$, 15 hr), HU, (2 mM, 24 hr), MMC (160 ng/ml, 24 hr) and Cisplatin, (10 μM 24 hr). Whole cell extracts were analyzed by Western blot with the indicated antibodies. Anti-β-Tubulin blot was used as a loading control.
Figure 27A:
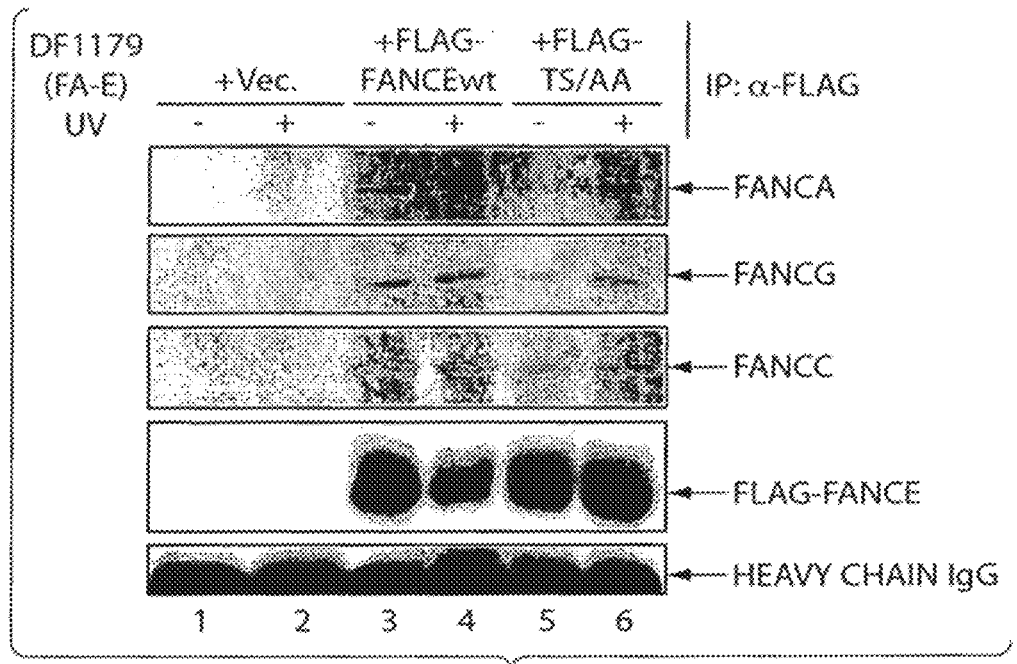
FIG. 27A. is a blot showing FA-E fibroblasts (DF1179) stably expressing empty vector (DF1179+Vec.), wild-type FANCE (DF1179+FLAG-FANCEwt) or the double mutant (DF1179+FLAG-TS/AA) were either untreated or treated with UV (60 J/m2) and incubated for 6 hr, whole cell extracts were subjected to immunoprecipitation with anti-FLAG, and the immune complexes were analyzed by SDS-PAGE, followed by Western blot analysis with anti-FANCA, anti-FANCG, anti-FANCC and anti-FLAG antibodies. Heavy chain IgG was used as a loading control.
Figure 27B:
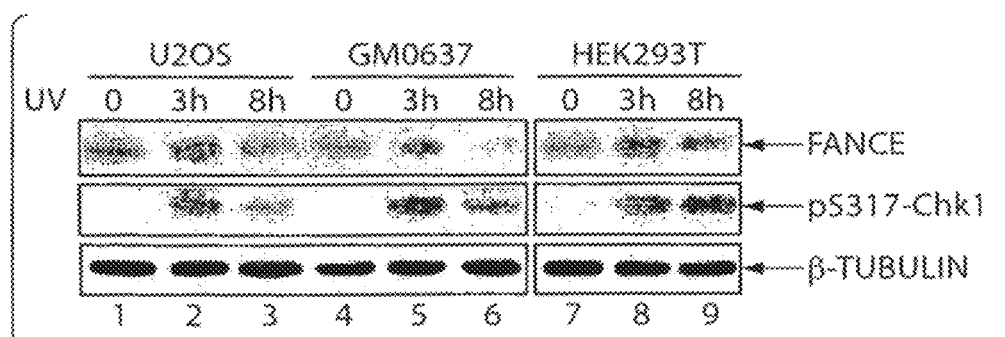
FIG. 27B is a blot showing U205, GM0637 or HEK293T cells were either untreated or treated with UV at 60 J/m2 and incubated for 3 hr or 8 hr, and whole cell extracts were analyzed for Western blot with indicated antibodies. Anti-β-Tubulin blot was used as a loading control.

HeLa cells were synchronized at the G1-S boundary with double-thymidine block and released the cells into S phase for 1 hour before DNA damage treatment. The level of FANCE protein was significantly decreased when a genotoxic stress (UV, HU, MMC or cisplatin) was delivered to cells undergoing DNA replication (FIG. 24B, lanes 2-5). UV-inducible FANCE degradation was also observed in other cell lines, including U2OS, GM0637 and HEK293T cells (FIG. 27B).

Figure 24C:
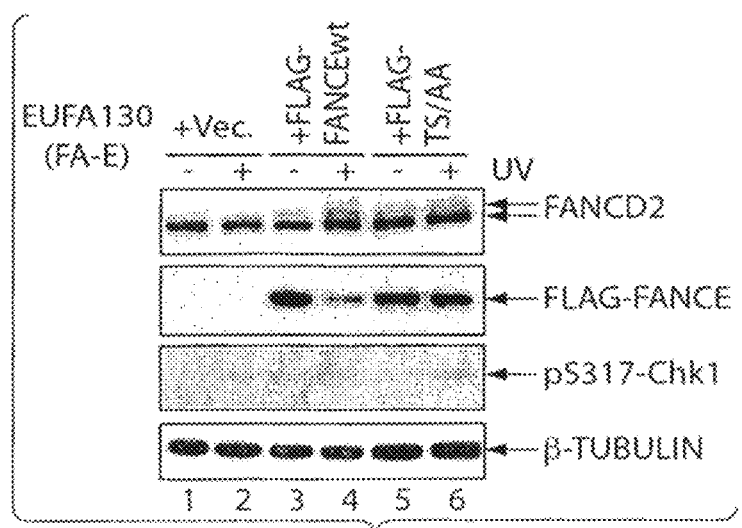
FIG. 24C is a photograph of a Western blot showing FANCE phosphorylation by Chk1 promotes its degradation. EUFA130 (FA-E) lymphoblasts were stably expressed with pMMP (empty vector), FLAG-FANCEwt, FLAG-TS/AA (the double mutant) as indicated. Cells were either untreated or treated with UV (60 J/m$^2$), after 8 hr, whole cell extracts were analyzed by Western blot with the indicated antibodies. Anti-β-Tubulin blot was used as a loading control.

It was tested whether Chk1-dependent phosphorylation regulates FANCE stability (FIG. 24C). FA-E (EUFA130) cells stably expressing wild-type FANCE (FLAG-FANCEwt) or the double mutant FANCE (FLAG-TS/AA) were examined. After UV treatment, wild-type FANCE (FLAG-FANCEwt) was degraded (FIG. 24C, compare lanes 3 and 4), but the double mutant FANCE (FLAG-TS/AA) was stable (FIG. 24C, compare lanes 5 and 6).

Figure 24D:
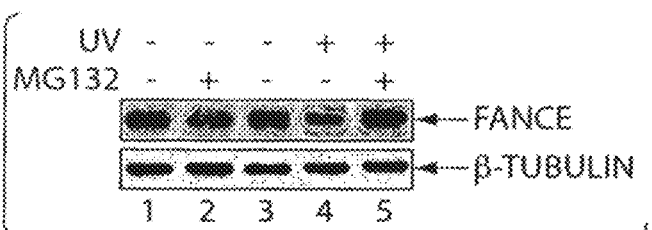
FIG. 24D is a photograph of a Western blot showing FANCE phosphorylation by Chk1 promotes its degradation. U2OS cells were either untreated or treated with UV(60 J/m$^2$) and incubated for 3 hr with or without 25 μM MG132 added to the indicated samples during the final 2 hr in cell culture. Whole cell extracts were analyzed by Western blot with the indicated antibodies. Anti-β-Tubulin blot was used as a loading control.
Figure 24E:
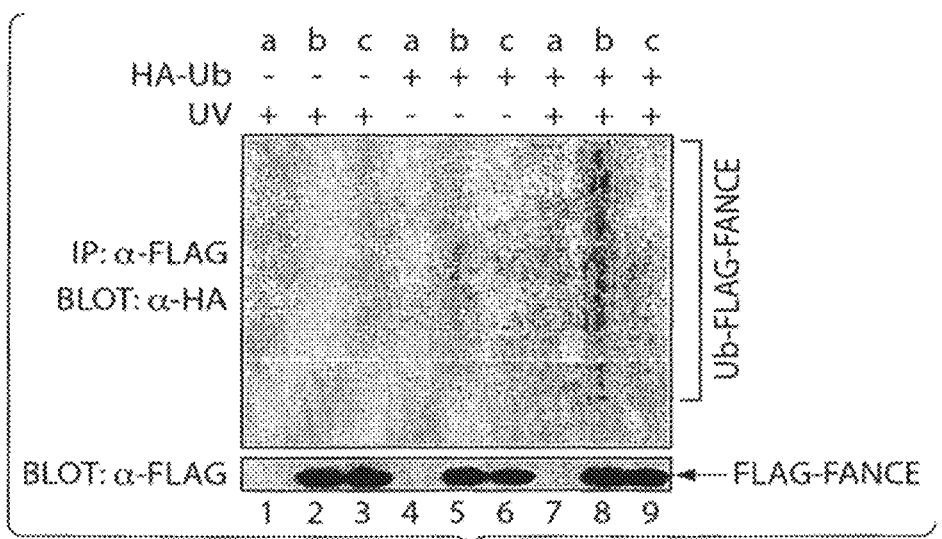
FIG. 24E is a photograph of a Western blot showing FANCE phosphorylation by Chk1 promotes its degradation. FANCE ubiquitination in vivo. U2OS stably expressing empty vector (a), FLAG-FANCEwt (b), and FLAG-TS/AA (the double mutant) (c) were transiently transfected without or with a cDNA encoding HA-ubiquitin, after 48 hr of transfection, cells were untreated or treated with UV (60 J/m$^2$), and incubated for 2 hr before cells were lysed in SDS denaturation buffer. FLAG-FANCEwt and the double mutant protein were isolated by anti-FLAG antibody immunoprecipitation. Immune complexes were run on SDS-PAGE and immunoblotted with anti-HA or anti-FLAG antibodies.
Figure 24F:
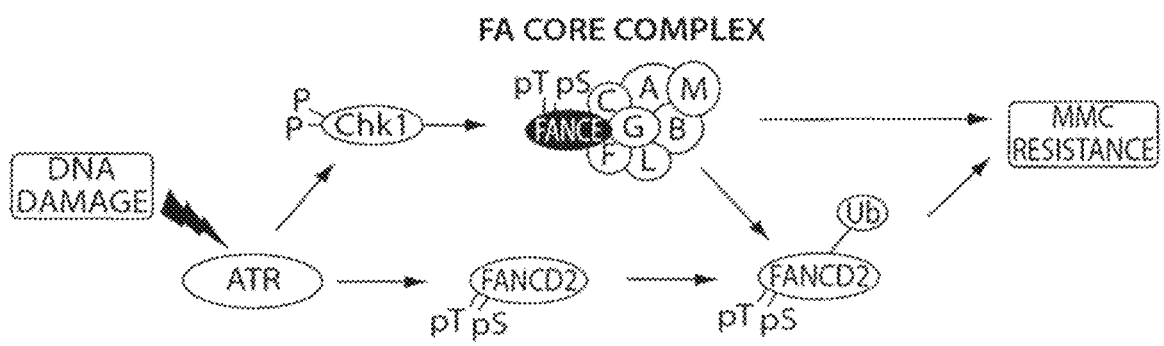
FIG. 24F is a schematic model showing the activation of the FA/BRCA pathway by ATR-Chk1 pathway. DNA damage or replication arrest (MMC, UV, IR, HU) activates the ATR-dependent phosphorylation of FANCD2 (6) and the Chk1-dependent phosphorylation of FANCE. Both monoubiquitinated FANCD2 and phosphorylated FANCE are required for MMC resistance. A non-ubiquitinated mutant of FANCD2 (K561R) or a non-phosphorylated mutant of FANCE (TS/AA) fails to correct MMC hypersensitivity.
Figure 25A:
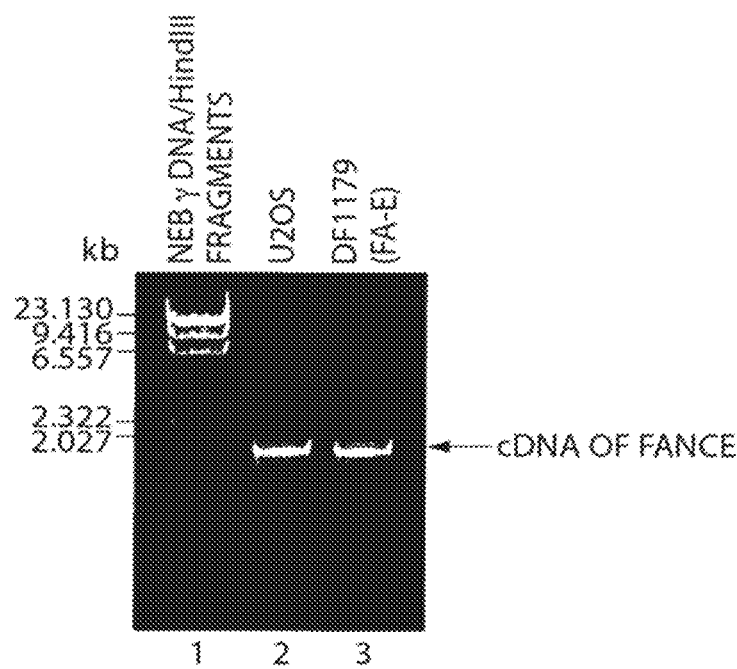
FIG. 25A is a photograph of a blot showing mutation analysis of a fibroblast line (DF1179) derived from an FA-E patient. RT-PCR amplification of RNA purified from DF1179 (FA-E) cells and U2OS cells (control) was performed using the specific primer pairs, and cDNA products were analyzed by agarose gel electrophoresis.
Figure 25B:
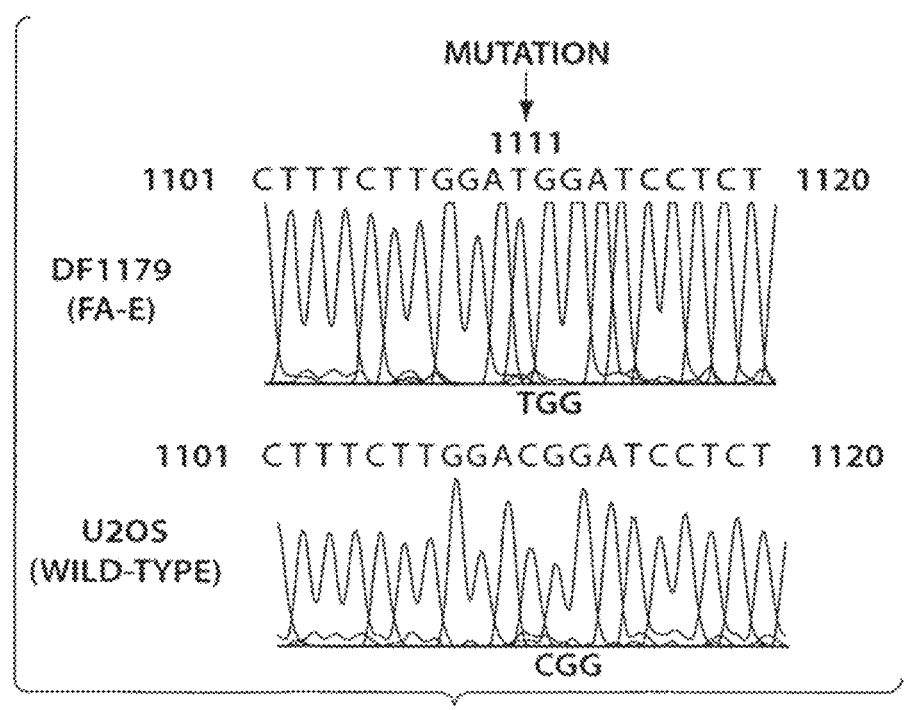
FIG. 25B is a schematic showing that mutation of the FANCE gene in FA-E fibroblast cell line (DF1179) was confirmed by direct DNA sequencing using different primers spanning from exon 1 to exon 10 of FANCE. The chromatograms shown indicate a C to T point mutation at 1111 of FANCE results in a missense mutation (R371W, Arg to Trp).
Figures 25C, 25D:
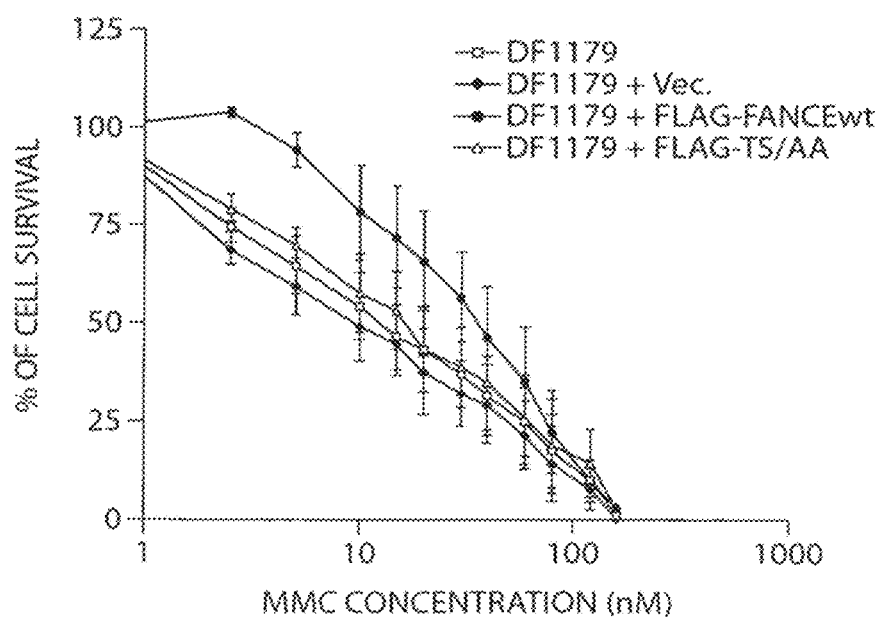
FIG. 25C is a schematic illustrating FANCE mutations.
FIG. 25D is a line graph showing complementation of MMC sensitivity of an FA-E fibroblast line, DF1179, with wild-type FANCE, but not with the double mutant of FANCE (TS/AA). MMC sensitivity of an FA-E fibroblast cell line, DF1179, with empty vector (pMMP), pMMP-FLAG-FANCEwt, pMMP-FLAG-TS/AA (the double mutant of T346A, S374A). The indicated retroviral supernatants were generated and used to transduce DF1179 cells. Puromycin-resistant cells were selected, and MMC sensitivity was determined as described below. The values shown are the mean±standard deviation (SD) from four separate experiments.

The role of the ubiquitin-proteasome pathway in the degradation of FANCE (FIG. 24D) was examined. Cells were treated with UV in the absence or presence of the proteasome inhibitor, MG132. MG132 treatment blocked the UV-inducible degradation of FANCE (FIG. 24D, lane 3). A cDNA encoding a HA-ubiquitin construct was transiently transfected into U2OS cells stably expressing wild-type FANCE (FLAG-FANCEwt) or the double mutant (FLAG-TS/AA). FLAG-tagged FANCE was immunoprecipitated, and immunoblotted with anti-HA and anti-FLAG antibodies. Following UV exposure, the high-molecular-weight ladder of polyubiquitinated products of the FLAG-FANCEwt was greatly enhanced by UV exposure (FIG. 24E, lane 8), which does not present in cells expressing empty vector or the double mutant (FLAG-TS/AA) (FIG. 24E, lanes 7 and 9, respectively), indicating that, following DNA damage, FANCE phosphorylation precedes its polyubiquitination. Taken together, these results indicate that the Chk1 mediated phosphorylation of FANCE promotes the ubiquitin-mediated degradation of FANCE. The specific E3 ubiquitin ligase complex required for FANCE degradation remains unknown.

Example 15

Figure 28:
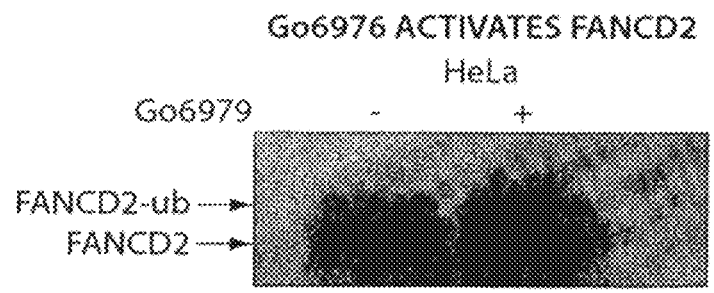
FIG. 28 is a photograph of a Western blot showing Hela cells treated with a Chk1 inhibitor show increased FANCD2 monoubiquitination. Human HeLa cells were treated with the Chk1 inhibitor, G06976. Fractionation of HeLa cell lysates on SDS-PAGE followed by immunoblotting with an antibody against the FANCD2 protein was then performed. Chk1 inhibitor-treated cells show increased levels of the ubiquitinated form of FANCD2, an indicator of Fanconi anemia pathway activity.

Human Cells Treated with Chk1 Inhibitors Show an Increased Activity of the Fanconi Anemia Pathway The activity of the Fanconi Anemia pathway can be monitored by evaluating FANCD2 monoubiquitination on the molecular level. Human HeLa cells were previously shown to have a viable FA-HR pathway by many criteria. The effect of a Chk1 inhibitor on HeLa cells by treating these cells with the inhibitor, G06976 was examined. Following treatment, HeLa lysates were examined by immunoblotting with the FANCD2 antibody (FIG. 28). The FANCD2-L band of higher mobility is the monoubiquitinated form of FANCD2. The lower band is FANCD2 that is not ubiquitinated. HeLa cells treated with G06976 show increased levels of FANCD2-monoubiquitination indicating that inhibition of Chek1 leads to an increased dependence of these cells on the FA-HR pathway.

Example 16

FA Cells are Hypersensitive to Chk1 Inhibition by Chk1 siRNA Depletion

EUFA426 human cells are FANCC-deficient cells isolated from a Fanconi Anemia patient. Previous experiments have demonstrated that these cells are deficient in the FANCC protein on the molecular level, and fail to activate downstream steps in the Fanconi Anemia-Homologous Recombination (FA-HR) DNA repair pathway, including a block of FANCD2 monoubiquitination following various DNA damage stresses by genotoxic agents and irradiation. EUFA426 levels complemented with a FANCC gene retrovirus were observed to restore FANCC levels, and to complement the hypersensitivity of these cells to genotoxic stresses and irradiation.

Figure 29:
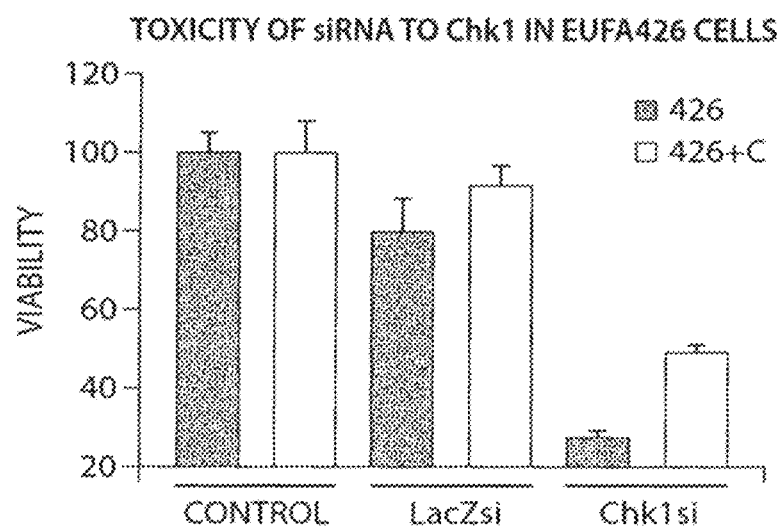
FIG. 29 is a bar chart showing toxicity of siRNA to Chk1 in EUFA426 (FANCC-deficient) cells. Cell viability determinations were applied for EUFA426 and EUFA426 cells complemented for expression of the FANCC gene with a FANCC-containing retrovirus. Cell viability assay was determined following introductions of LacZ or Chk1 siRNAs (LacZsi and Chk1si respectively) were performed by standard protocols.

EUFA426 and EUFA426+C cells were transfected with siRNAs for the Chk1 kinase according to standard protocols in previous experiments For controls, the same cells were also transfected with a control LacZ si RNA. Cell viability was scored for the cells that were not transfected (control) compared with LacZ and Chk1 siRNAs. It was found that EUFA426 cells had reduced viability after transfection with the Chk1 siRNA (FIG. 29). With EUFA426+C cells (having restored the FANCC levels), the level of cell viability in the presence of the Chk1 siRNA was significantly increased.

Therefore, FANCC-deficient cells are selectively hypersensitive to Chk1 kinase loss of activity by siRNA depletion.

Example 17

FA-HR Deficient Cells are Hypersensitive to Chk1 Inhibition

Figure 30:
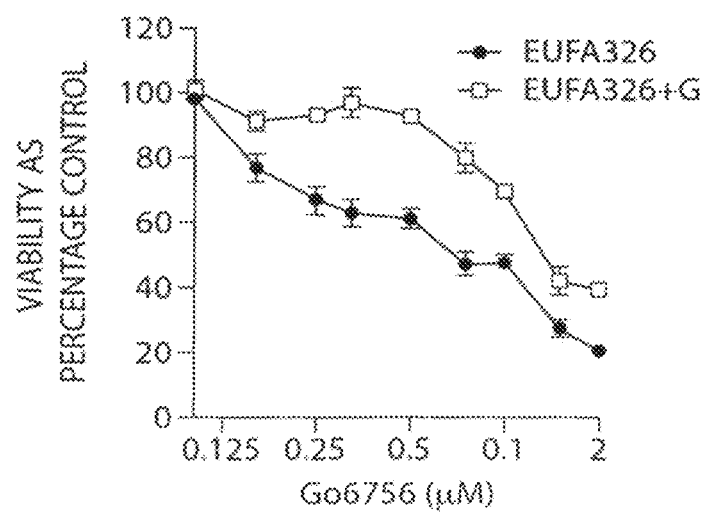
FIG. 30 is a line graph showing Fanconi Anemia Deficient cells are hypersensitive to a Chk1 inhibitor in cell viability measurements. Clonogenic cell survival assays were completed following the exposure of EUFA326 (FANCG-deficient) and EUFA326+G (FANCG-complemented) human cells to the Chk1 kinase inhibitor, G06976 at varying doses as shown. At each exposure dose, there is a differential cell killing to the FANC-cells.

The sensitivity of Fanconi Anemia deficient cells was also examined by testing with a known Chk1 kinase inhibitor, G06976. In the experiment, EUFA326 cells that are isolated from a Fanconi Anemia patient known to be deficient in the FANCG complementation group gene, were evaluated. In addition, EUFA326 cells that have been complemented with FANCG by retroviral transduction, were compared. Previous experiments have demonstrated that these cells are deficient in the FANCG protein by immunoblotting, and fail to activate downstream steps in the Fanconi Anemia-Homologous Recombination (FA-HR) DNA repair pathway, including a block of FANCD2 monoubiquitination following various DNA damage stresses by genotoxic agents and irradiation. EUFA326 levels complemented with a FANCG gene retrovirus were observed to restore FANCG levels, and to complement the hypersensitivity of these cells to genotoxic stresses and irradiation (FIG. 30).

The EUFA326 (FANCG-deficient) and EUFA326+G (FANCG-complemented) cells were tested for sensitivity to the Chk1 inhibitor. In cell viability determinations, EUFA326 cells were hypersensitive to the Chk1 inhibitor G06976 relative to the EUFA326+G cells at all doses.

Example 18

Treatment of FA-HR Deficient Cells with a Chk1 Inhibitor Leads to Extensive Chromosome Damage and Breakage The FANCE-deficient human fibroblast cell line, EUFA130, and EUFA130 complemented with a stably reintroduced FANCE expression from a retrovirus, were compared in several tests for genome stability and cell cycle control. EUFA130+E cells were shown to have restored FANCE levels by immunoblotting.

EUFA130 and EUFA130+E cells were plated at low density, and subsequently treated with 1 uM of the Chk1 inhibitor G06976 and then tested for the distribution of cells at different cell cycle phases. It was found that the Chk1 inhibitor caused an increased fraction of cells in G1 and the subG1 cell population by propidium iodide staining. SubG1 cells are indicative of cells entering apoptosis.

Figure 31:
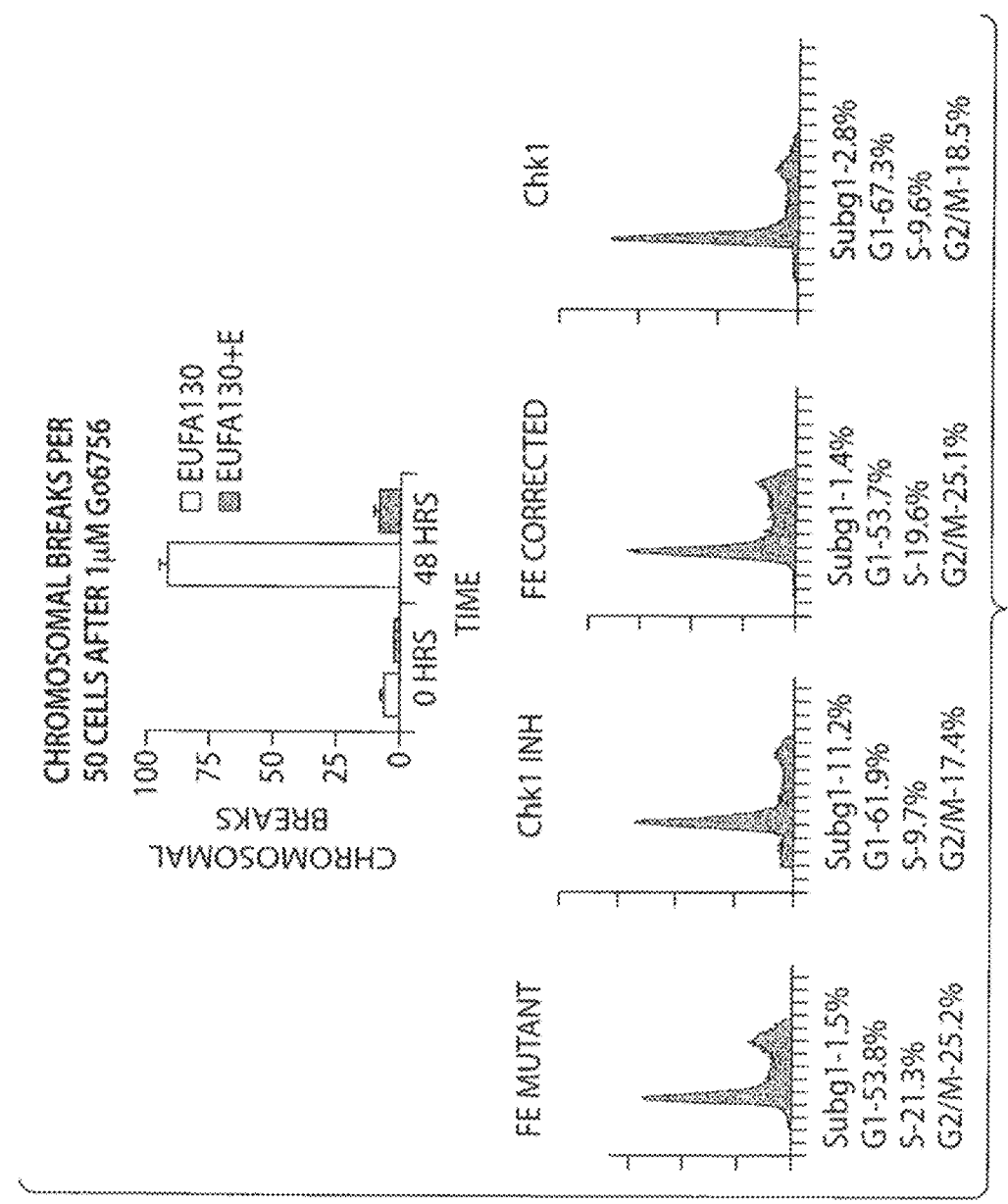
FIG. 31 is a bar chart and series of schematics showing Fanconi Anemia deficient cells are subject to increased chromosome breakage following incubation with a Chk1 inhibitor, and show cell cycle changes. The FANCE deficient cell line, EUFA130 (FE mutant) and EUFA130 corrected with the FANCE gene by complementation (FE Corrected) were compared by two analysis. In the top panel, the level of chromosome breakage was scored at 0 and 48 hours following exposure to 1 uM G06976. The number of chromosome breaks was quantitated from 50 cells. In the lower panel FE mutant and FE Corrected cells were compared for the fraction of cells in cell cycle phases.

In addition, the level of chromosome breaks was scored for EUFA130 and EUFA130+E cells treated with the Chk1 inhibitor. EUFA130 cells have a low level of chromosome breakage (FIG. 31). Following incubation with the Chk1 inhibitor, the level of chromosome breakage was dramatically increased. In contrast, EUFA130+E cells restored the low level of chromosome damage following treatment with a Chk1 inhibitor.

These experiments indicate the selective vulnerability of the FA-deficient cells to chromosome damage in the presence of a Chk1 inhibitor. The two parts of the experiment combined would indicate that the Chk1 inhibitor preferentially drives FA-deficient cells into cell death.

Example 19

Human Tumor Cell Lines are Sensitive to Inhibition of Chk1 Kinase or Atm Kinase

Human cancers show many genomic alterations including the chromosomal rearrangement, deletion, amplification, mutation and/or epigenetic silencing or overexpression of many genes. In the cases of DNA repair and DNA damage response pathway genes, there is significant evidence of modification of these genes in human cancers. For the Fanconi Anemia-Homologous Recombination pathway there is ample evidence to suggest that changed expression or mutation is often observed in tumors (FIG. 32).

The human ovarian tumor cell line, 2008, is known to be deficient in the FA-HR pathway because these cells have epigenetic silencing of the FANCF gene from the hypermethylation of the FANCF promoter. Hypermethylation of the FANCF promoter leads to reduction in FANCF transcription and consequently FANCF protein levels of the cells are significantly lower. Epigenetic silencing of FANCF is a frequently observed event in human tumors. The 2008 cell line was transfected with the FANCF gene, expressed separably, and these derivative cells (2008+F) shown to express elevated levels of FANCF.

The ovarian 2008 cells and 2008+F cells were then compared for cell survival following treatments with the Chk1 kinase inhibitor G06976, or the Atm kinase inhibitor KU55933 and cell viability and proliferation tested in a clonogenic assay. Cell colonies were stained by standard procedures and visualized (FIG. 33). Colony numbers scored indicate that the treatment with the Chk1 inhibitor led to a significant reduction in cell survival. Therefore, 2008 cells are hypersensitive to Chk1 inhibition. Similarly, the G06976 Atm inhibitor led to a comparable hypersensitivity. Therefore, FA-deficient cells are particularly vulnerable to two of the DNA damage checkpoint kinase blockades, indicating that these cells are dependent on these pathways for their survival.

Collectively, the experiments demonstrate that the biomarker identification of FA deficiency identifies a subgroup of cells where there would be a utility for the application of Chk1 inhibitors. The selective use of a Chk1 inhibitor can be defined by evaluating tumor specimens for FA-deficiency as is illustrated here with FANCE-deficient cells (FIG. 31) and FANCF-deficient ovarian human tumor cells (FIG. 33).

This discovery has important ramifications in oncology clinical settings as it points to the therapeutic utility of Chk1 kinase inhibitors in circumstances where the status of the DNA repair pathways is understood. In the examples shown here, it is clear that the status of the Fanconi Anemia-Homologous Recombination pathway is an important component of prediction for the hypersensitivity of tumors to Chk1 inhibitors. The status of the pathways is likely to be identifiable by multiple biomarker components reflecting different nodal points of the activity of the overall pathway. This invention discloses the means to evaluate DNA repair biomarkers from one or more than one pathway in conjunction.

The DNA repair biomarkers are particularly applicable in several settings. Biomarkers of this type will be useful for preclinical development, for the subsetting of patients, as pharmacodynamic biomarkers in the course of clinical trials, and for directing therapeutic decision-making in the oncology clinics.

Example 20

Evidence for DNA Repair Protein Changes in Human Cancers

DNA repair pathway proteins were monitored by immunohistochemistry (IHC) using pathway-, protein-, or post-translational epitope-specific changes as biomarkers of the pathway activity.

Human cancers may be surveyed by analysis of formalin-fixed paraffin-embedded (FFPE) specimens where multiple sections of whole specimens or tumor micro arrays (TMAs) may be evaluated. For TMAs, human cancers were arrayed in a format to display three sections of tumor and three sections of pathologically normal surrounding tissues for each patient with a designated cancer diagnosis. Alternatively, TMAs of identified tumor zones from patients are compared to one another.

Figure 35A:
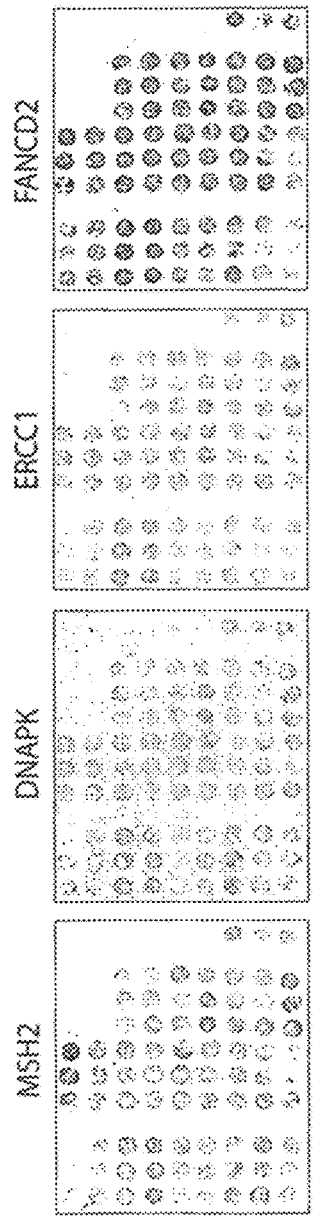
FIGS. 35A-C. Head and Neck Cancer Tumor Micro Array analyzed with Eleven DNA repair and DNA damage signaling biomarkers by immunohistochemistry. Serial sections of a Head & Neck TMA were prepared for IHC. The antibodies used for this experiment were against the following epitopes.
Figure 35B:
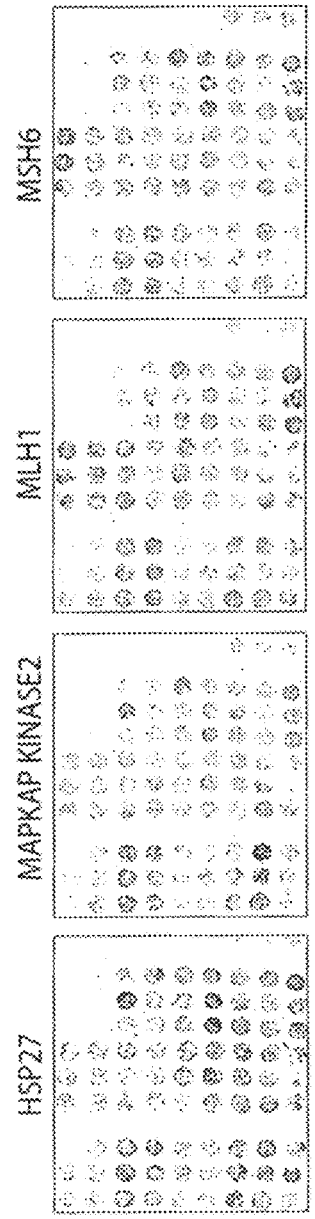
Figure 35C:
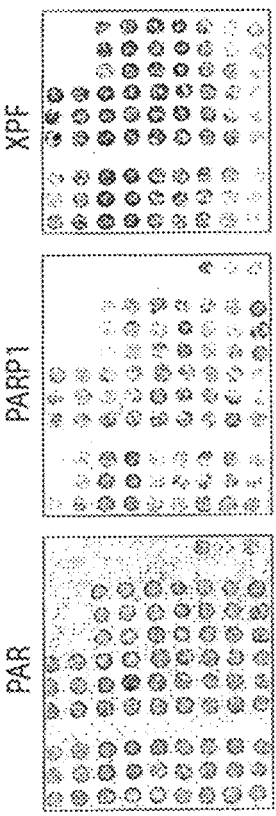

To illustrate the dynamic nature of DNA repair biomarker expression patterns in human cancers, TMAs of the same cancer type [head and neck squamous cell carcinomas] were analyzed extensively. FIG. 35A-C illustrates a human head & neck cancer tumor TMA where the tumor cores were IHC stained with antibodies against eleven DNA repair biomarkers. The biomarkers included a FA/HF component (FANCD2), Non-Homologous end joining biomarkers (PT2609 DNAPK), several Nucleotide Excision repair components (XPF, ERCC1), three Mismatch repair component (MLH1, MSH2, and MSH6), Base Excision repair biomarkers (PARP1, PAR), and DNA damage components (PT334 MapkapKinase2, S78 HSP27) from serial sections of the TMA. Each antibody has been optimized for IHC based on a survey of human cancers. Generally, the DNA repair and DNA damage proteins are expressed in these tissues, but the expression levels and cellular localization may vary.

Figure 36:
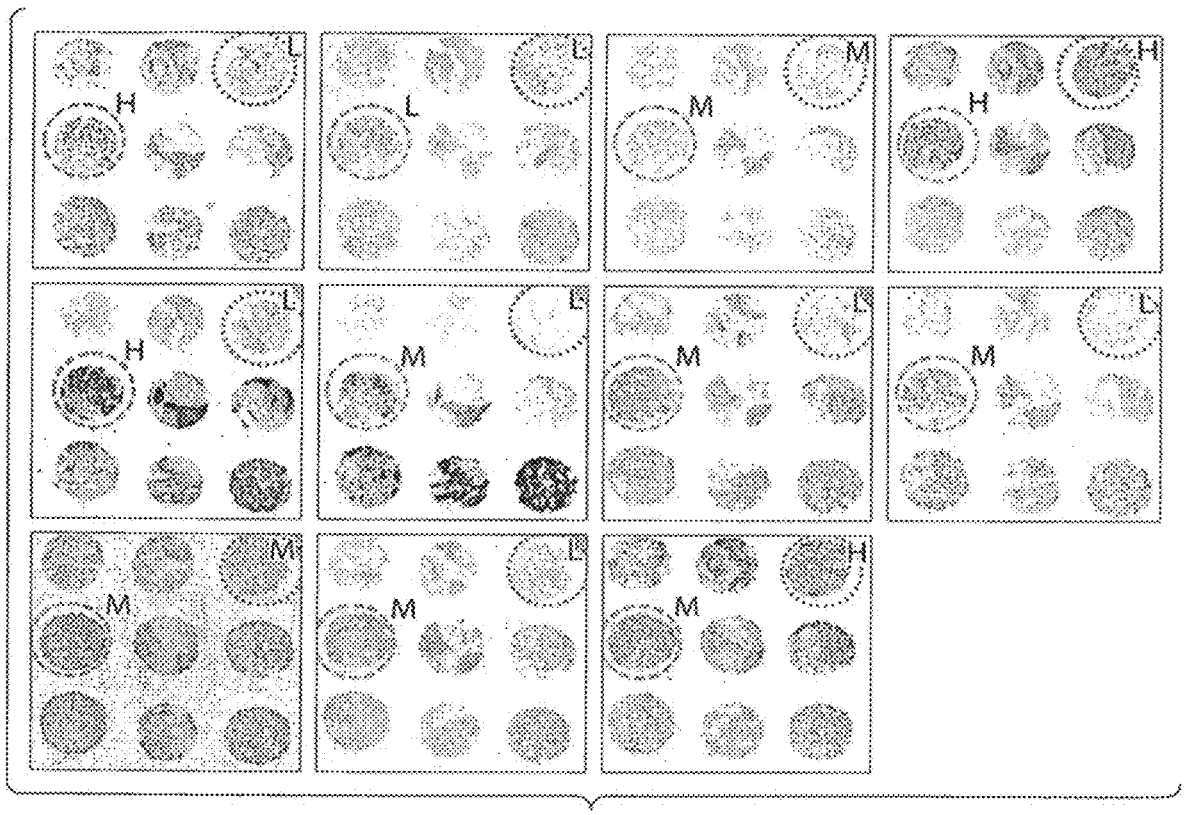
FIG. 36. Comparison of IHC staining pattern of 11 DNA repair and DNA damage signaling biomarkers with 9 tumor cores from patients with Head and Neck Cancer. A Tumor MicroArray (TMA) from patients with Head and Neck Cancer was investigated with a group of DNA repair and DNA damage signaling biomarkers. Dashed yellow circles indicate a single patient tumor in the array. Likewise, dashed purple circles delineate a second patient tumor in the TMA. The level of staining is approximated by H, high, M, medium, or L, low to indicate variations per marker and per tumor specimen. The biomarkers evaluated are from left to right (Top Row, MSH2, DNAPK, ERCC1, FANCD2) (Middle Row, HSP27, MapKapKinase2, MLH1, MSH6) (Bottom Row, PAR, PARP1, XPF)

The images are also viewable based on single patient tumor cores as shown in FIG. 36. In this patient subset a selection of 9 tumor cores from head and neck cancers is displayed from 9 patients. The highlighted cores are the same cancer core position on the TMA. Therefore, in the illustration, one patient core is identifiable with an orange dashed circle surrounding it, and a second patient core in the array has a purple dashed circle surrounding it. The relative staining intensity by IHC and a scoring evaluation is listed as H, high, M, medium, or L, low for comparisons. Note that there are several markers where the IHC intensity level changes in relative distribution from patient to patient. This example illustrates that utility in comparing multiple biomarkers of DNA repair and DNA damage signaling pathways in cancers.

Figure 37A:
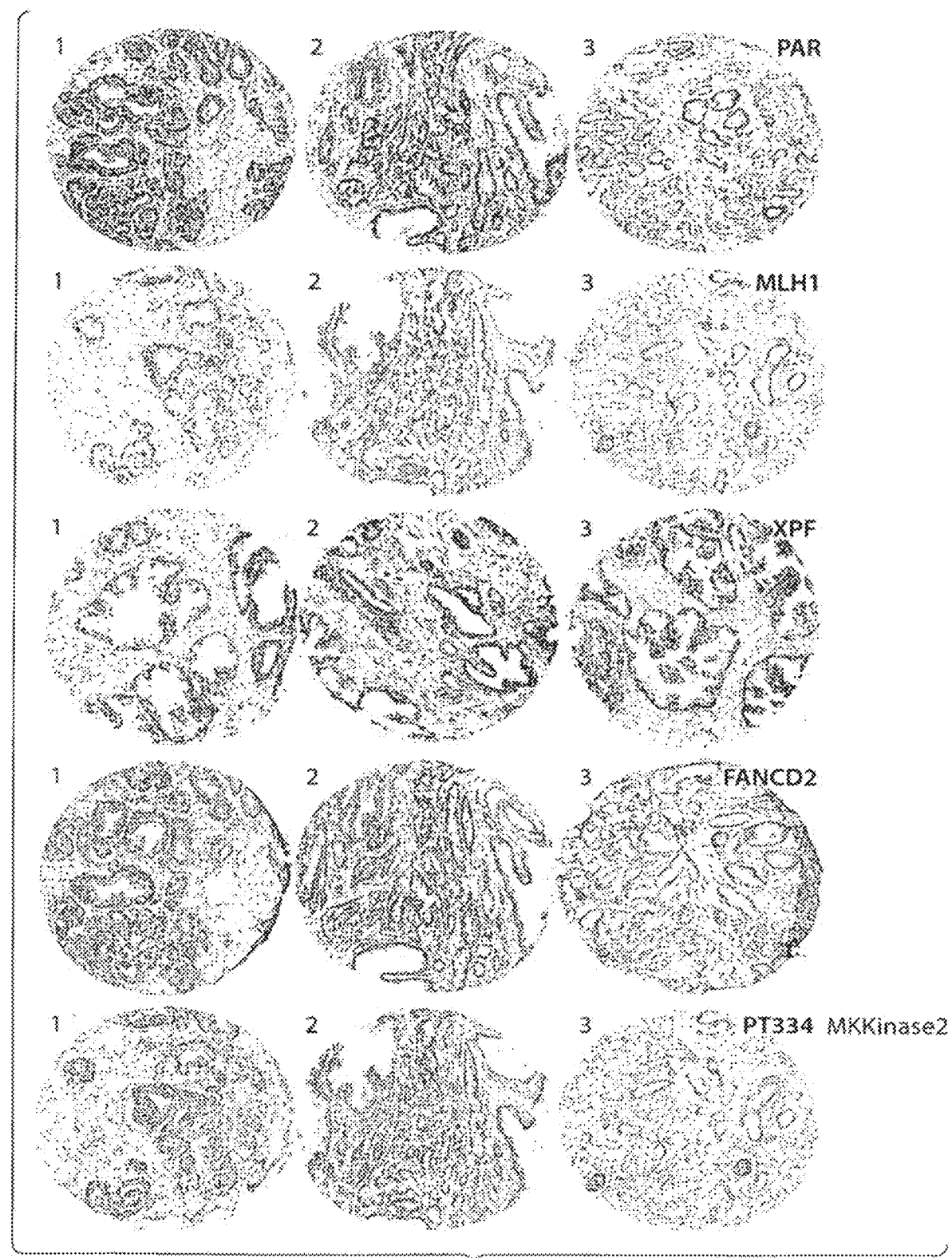
FIGS. 37A-B. Example of DNA repair biomarker analysis for human prostate cancer specimens.
Figure 37B:
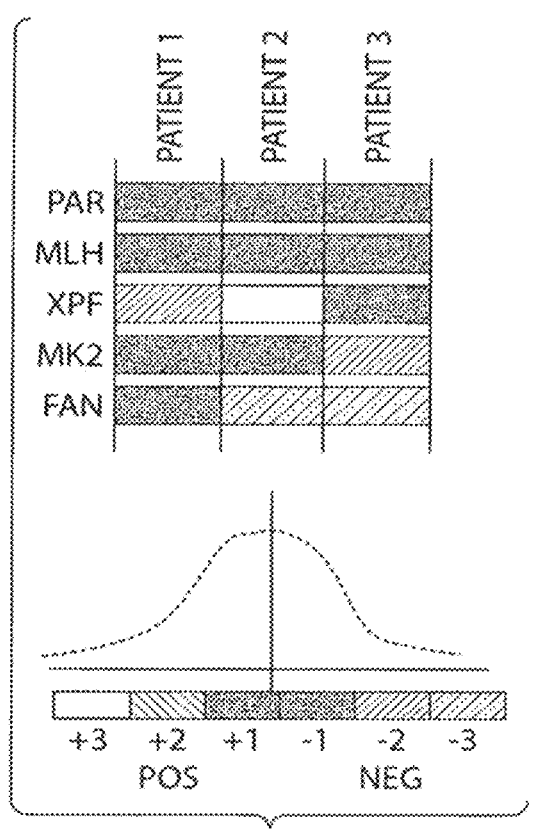

Another example of DNA repair biomarker analysis is shown for human prostate cancer specimens. In FIG. 37A, a representation of three patient tumor specimens is illustrated with five DNA repair and DNA damage signaling biomarkers from different pathways. Serial sections of the same TMA are IHC stained with each of the five biomarkers. The tumor core images are extracted from the TMA for a higher power view to interpret via image analysis. FIG. 37B shows the variation per biomarker for Patient 1, 2, and 3. A colorized output displays the prostate cancer patient variation for these three example specimens. Significantly, DNA repair biomarkers vary to differing extents depending on the patient. FIG. 37B illustrates incidences where the DNA repair biomarkers XPF and FANCD2 have significantly different expression outcomes.

Figure 38A:
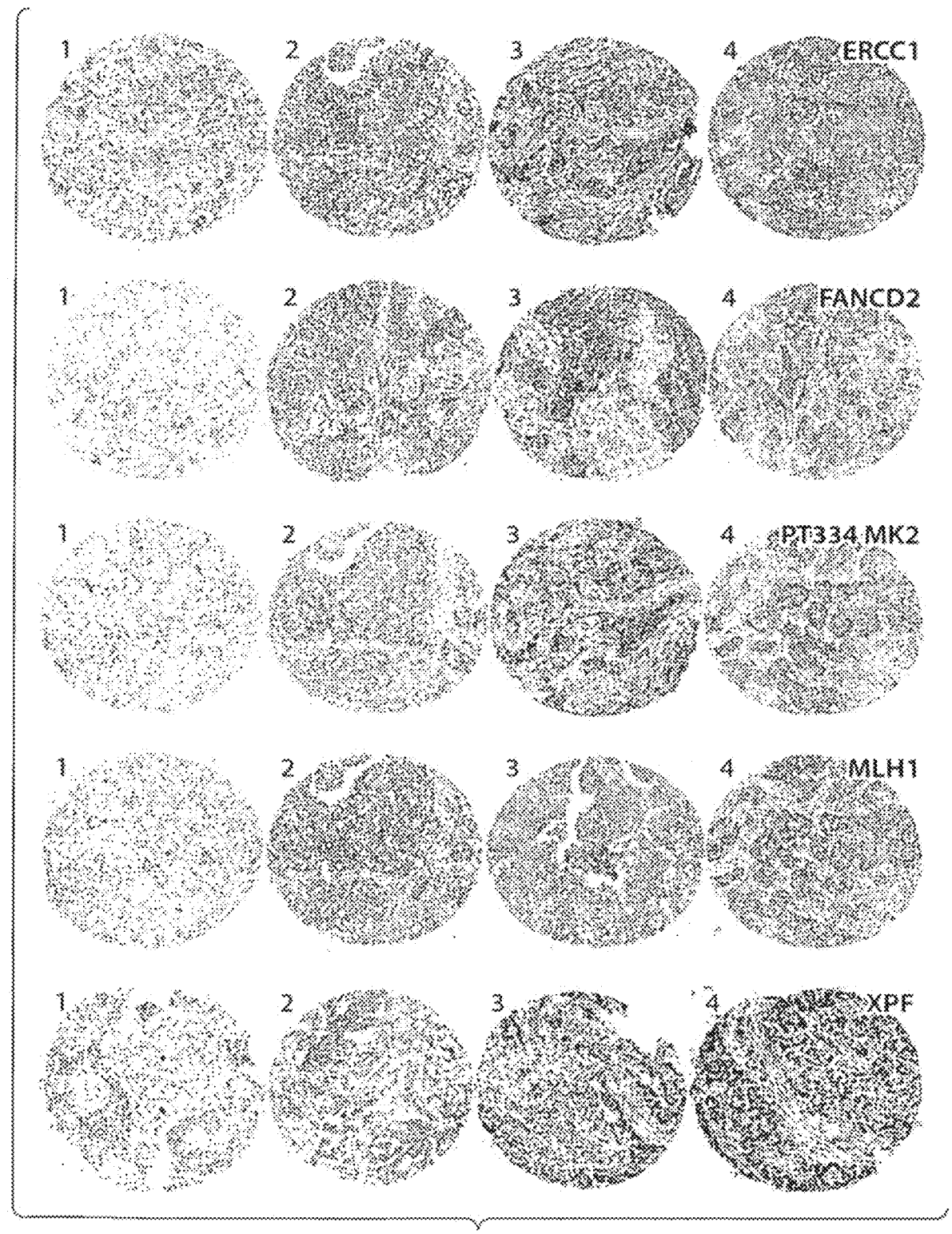
FIGS. 38A-B. Example of DNA repair biomarker analysis demonstrated for human Non-small cell lung cancer (NSCLC) specimens.
Figure 38B:
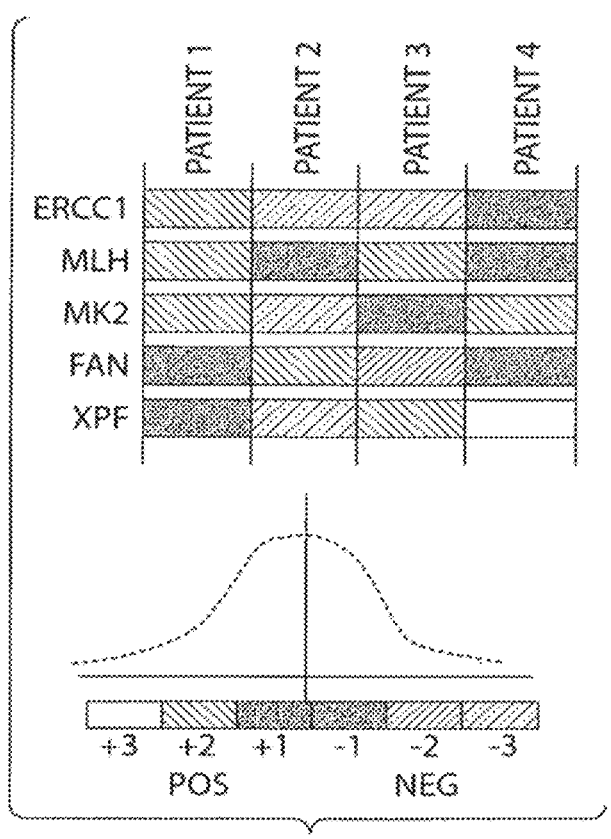
Figure 39A:
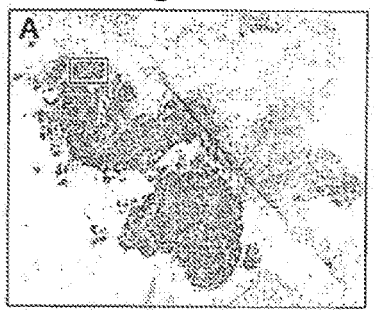
FIGS. 39A-F. Selection of Regions of Interest (ROI) from serial sections of an ovarian serous carcinoma. Serial sections of the tumor specimen. Boxes represent areas selected based on hematoxylin & eosin staining and bearing high tumor volume in the selected area.
Figure 39B:
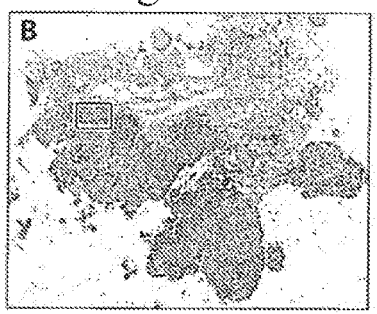
Figure 39C:
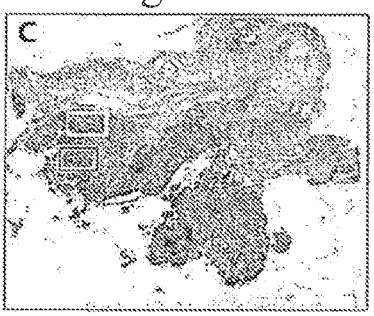
Figure 39D:
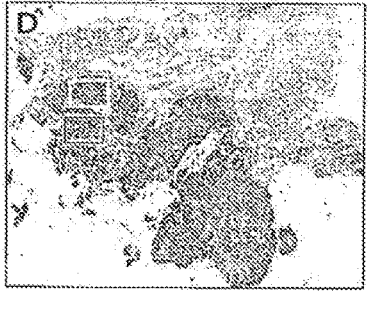
Figure 39E:
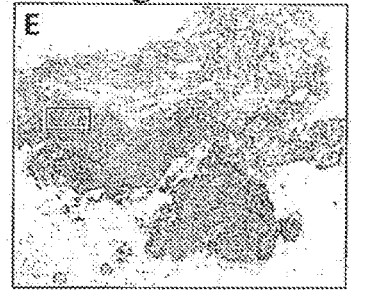
Figure 39F:
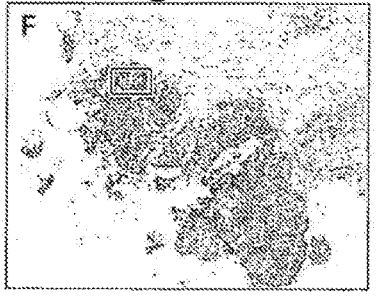
Figure 40A:
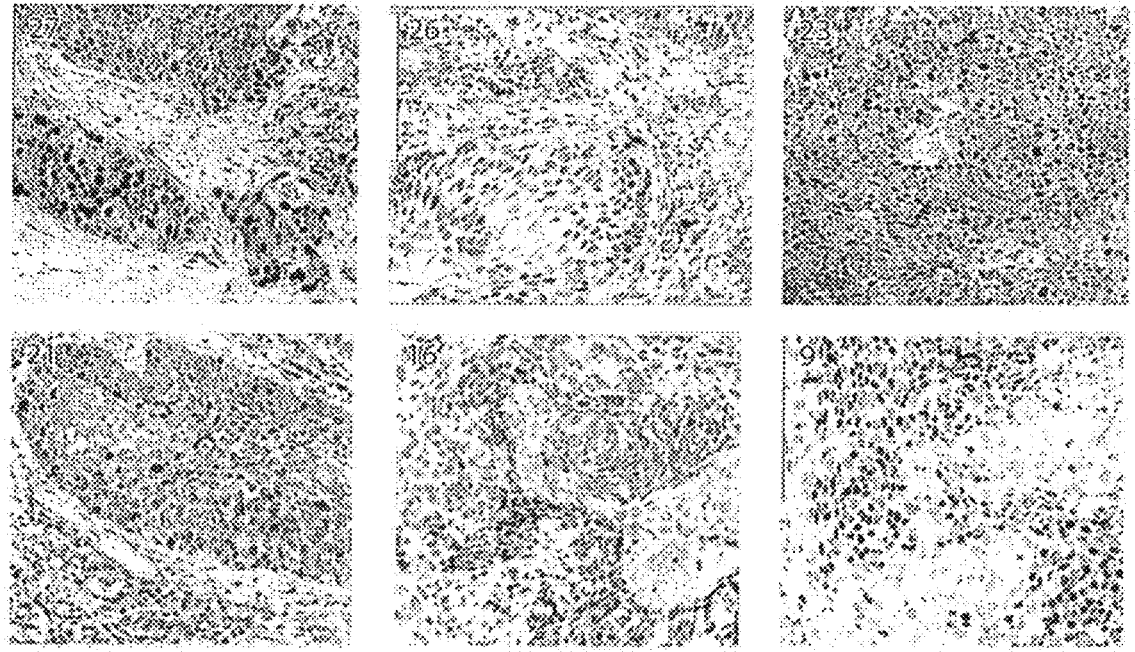
FIGS. 40A-D. Comparison of six patients with Head & Neck cancer for IHC staining patterns of DNA repair and DNA damage signaling pathways. IHC staining of the four markers is as shown with FIG. 40A, FANCD2, FIG. 40B, MLH1, FIG. 40C, XPF, and FIG. 40D, PT334 MapkapKinase2. In each of FIGS. 40A-D, the six head & neck cancer patients are as numbered 27, 26, and 23 (upper panel), and 21, 16, 9 (lower panel).
Figure 40B:
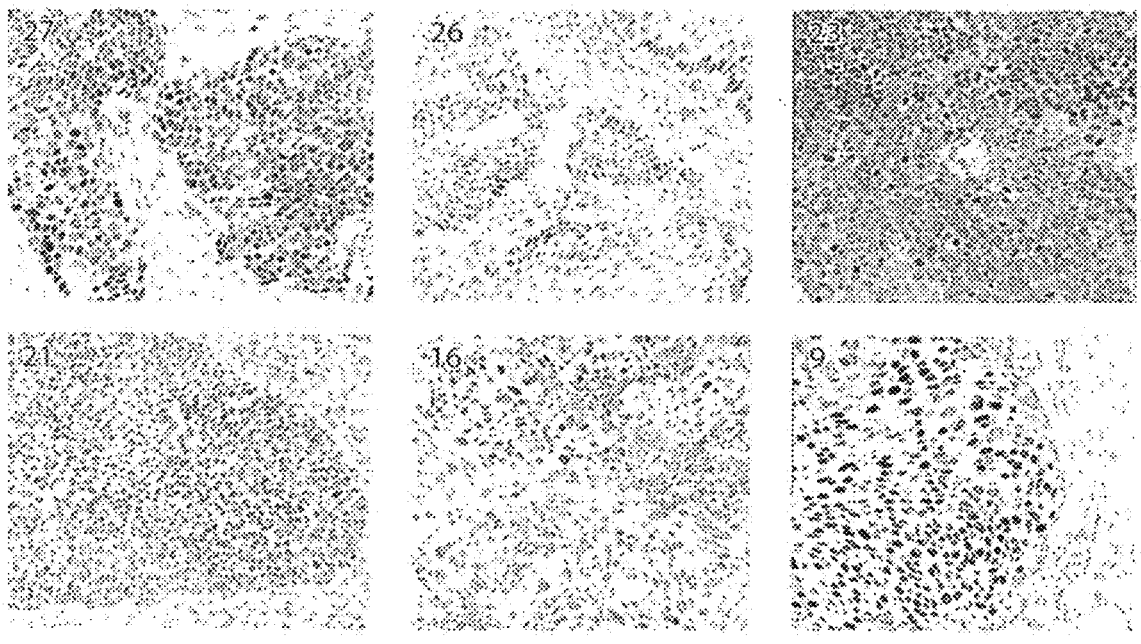
Figure 40C:
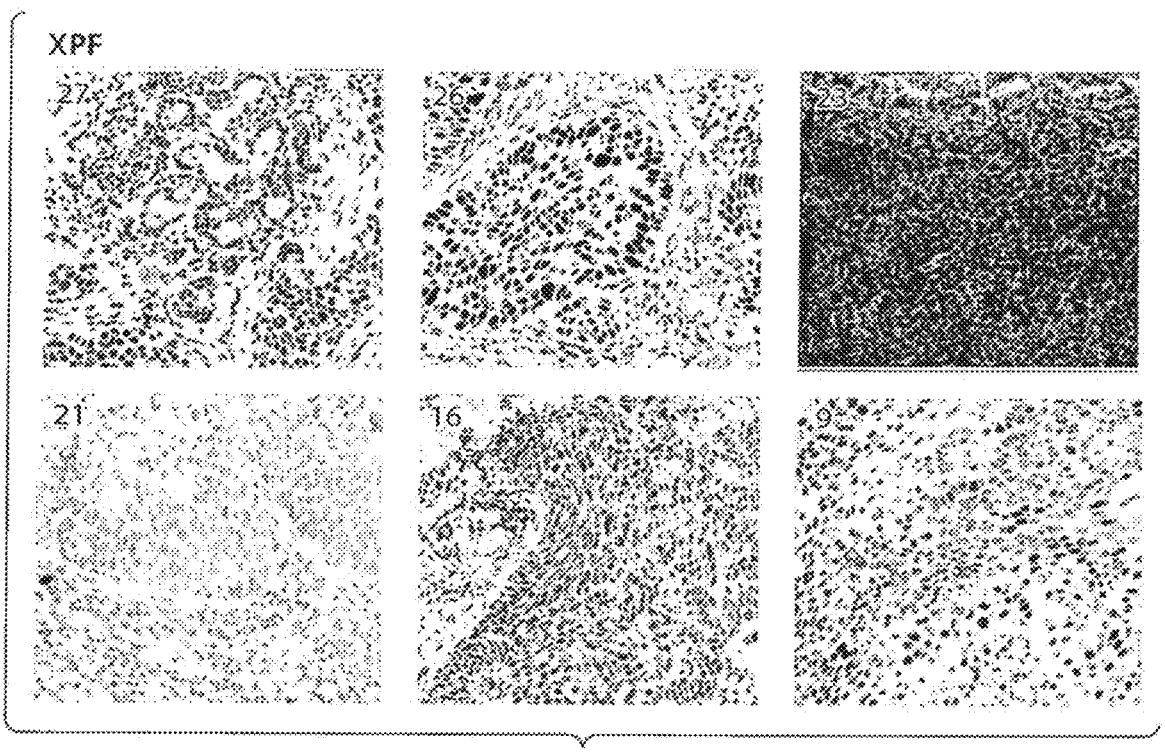
Figure 40D:
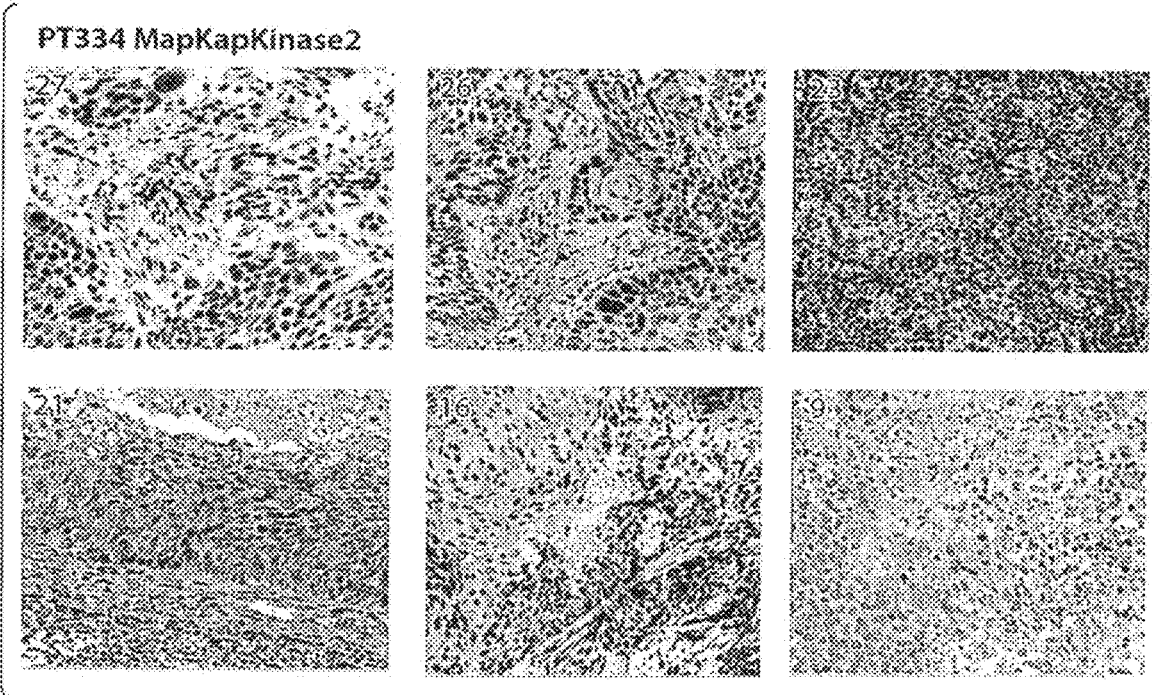
Figure 41C:
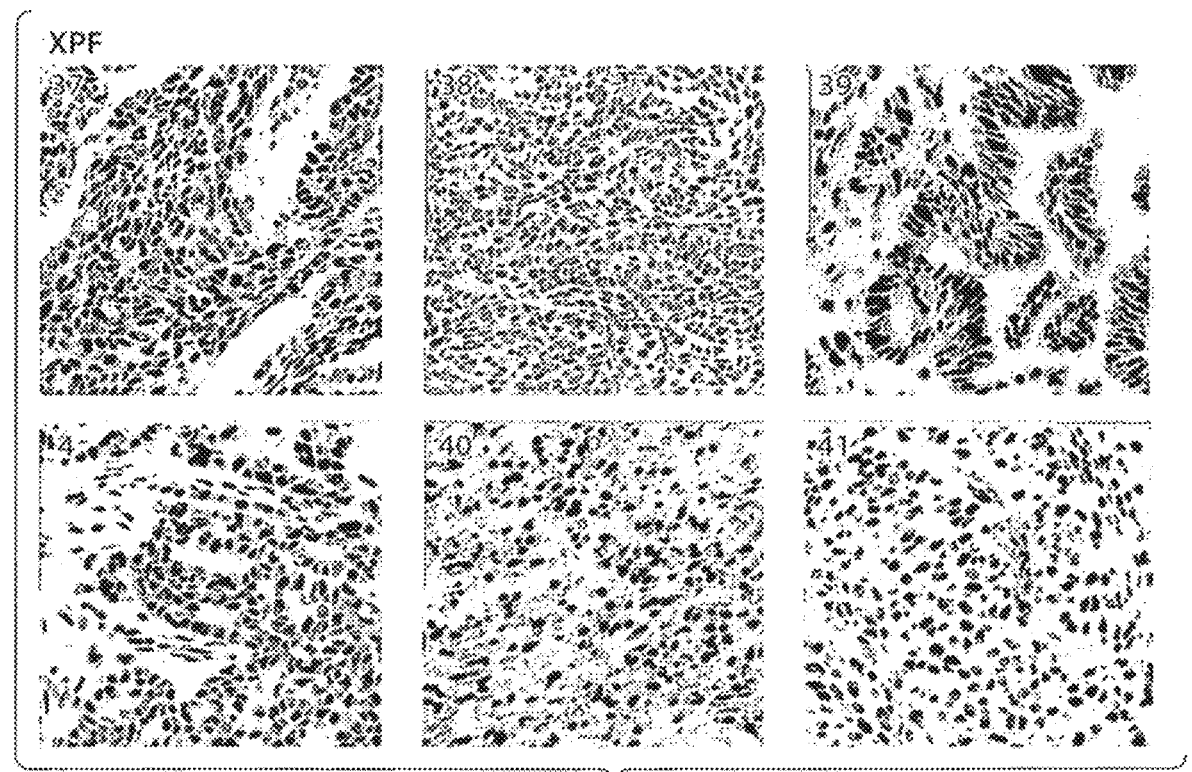
Figure 41D:
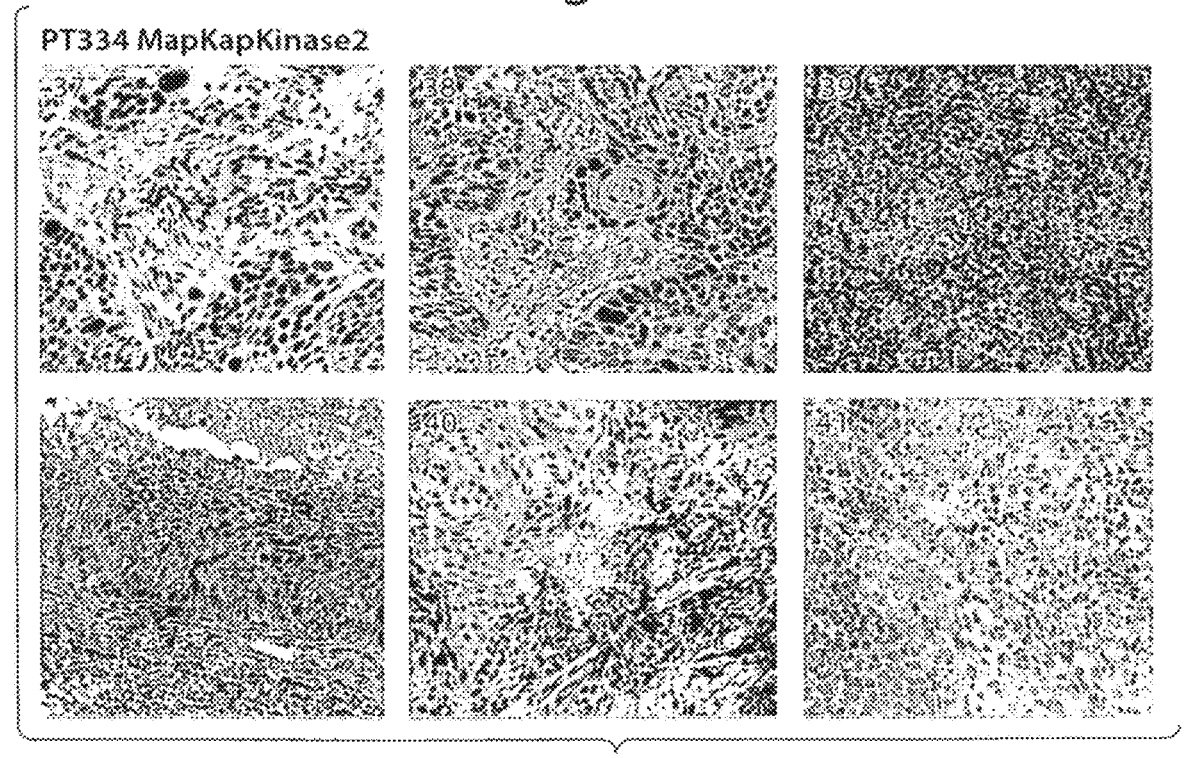
Figure 41E:
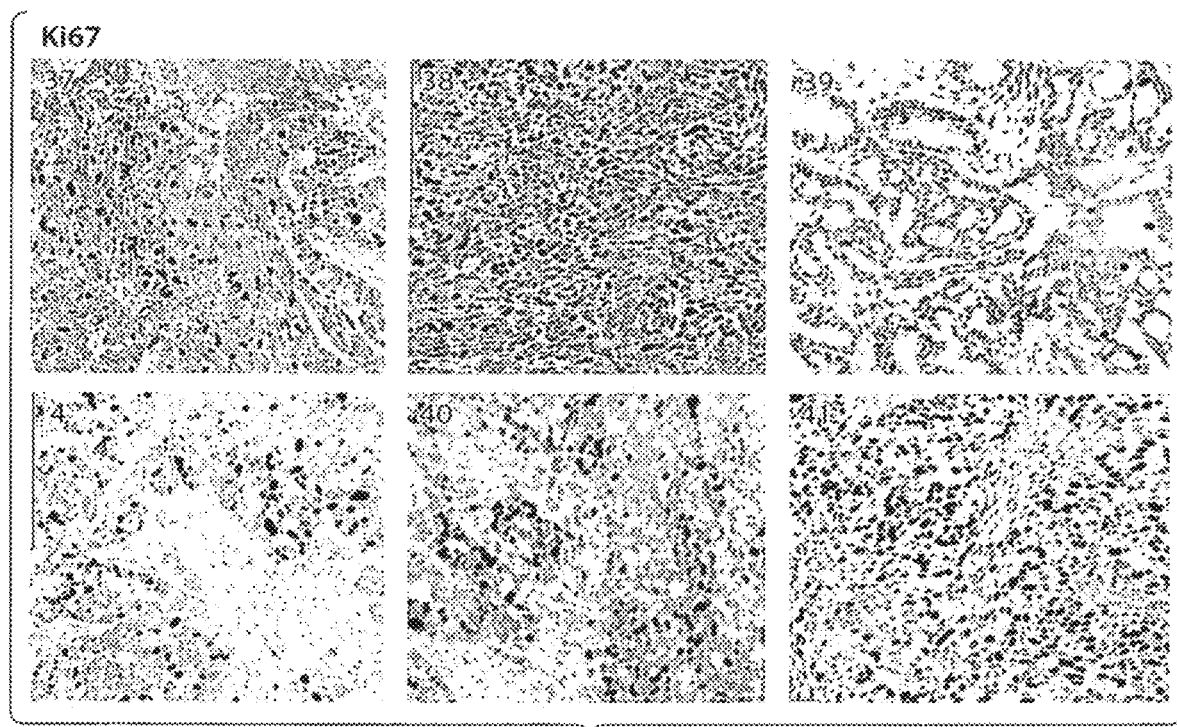

A further example of DNA repair biomarker analysis is demonstrated for human Non-small cell lung cancer (NSCLC) specimens. In FIG. 38A, a representation of four patient tumor specimens is illustrated with five DNA repair and DNA damage signaling biomarkers from different pathways. As above with other TMAs, serial sections of the NSCLC TMA are stained with each of the five biomarkers as shown in the figure. The tumor core images are extracted from the TMA for a higher power view to interpret via image analysis. FIG. 38B shows the variation per biomarker for Patient 1-4 using a colorization scheme to describe the output. Importantly, there is patient-to-patient variation regarding the relative expression of DNA repair biomarkers.

Whole sections of human tumors are evaluated by inspection of serial sections. The Region of Interest (ROI) within the tumor is identified by a pathology team of investigators by considering the Hematoxylin and Eosin staining pattern and by the collective staining patterns of the groups of biomarkers. The image file is manipulated and annotated to overlay the same zone of the tumors. The ROIs are designated in this example by boxes in FIG. 39A-F. Shown are a group of 6 serial sections stained by IHC with 6 different DNA repair antibodies for the biomarker analysis. It is evident from inspecting the morphology of the tumor that ROI zones are selecting comparable areas of each section for further image analysis. Note that the absolute orientation on the specimen slide may vary, but that the ROI selection is delineated so that the same tumor area may be evaluated with separate staining with the different DNA Repair and DNA damage signaling biomarkers.

Example 21

Comparison of Patients with Head and Neck Cancer for DNA Repair Biomarker Profiles Patients with head and neck cancer were evaluated using a group of DNA repair biomarkers as noted in the following figures. Patients were treated with chemoadjuvant (induction) therapies containing docetaxel, cisplatin, 5-FU, and received radiation therapies. However, the distinction of an ability to respond or fail to respond to this chemoradiation therapy regimen is not understood with regard to molecular markers. Tumor biopsies were received prior to the therapy, at which point tumor specimens were formalin-fixed and paraffin-embedded. The four markers (A=FANCD2, B=MLH1, C=XPF, and D=PT334 MAPKAPKINASE2) were co-analyzed with 6 patient tumor specimens, and the results are shown in FIGS. 40A-40D. In each subsection of FIGS. 40A-40D, the specimen material is in the same relative position in the figure per patient, and the patients are anonymously numbered (Patient 27, 26, 23, 21, 16, and 9).

Pathology scoring of DNA repair biomarkers can be conducted by routine pathology scoring. For example, specimens are examined for the integrity of the staining pattern. Quality analysis with these biomarkers at higher power than is shown in the example indicates that the staining is entirely nuclear for the biomarkers FANCD2, XPF, MLH1, and Ki67 shown below. In addition, the biomarker PT334 MAPKAPKinase2 has nuclear and cytoplasmic staining depending on the context of the tumor. For example, ovarian tumors show a combination of nuclear and cytoplasmic staining whereas head and neck cancers show principally nuclear staining. An alternative strategy is to use machine-driven collection of IHC signals and algorithms to interpret the staining pattern. For DNA repair proteins, generally the IHC pattern is nuclear. Positive pixels are seen either in a nuclear or subnuclear distribution, such as with nuclear foci. Shown in the FIG. 40 A-D is nuclear staining of the four biomarkers.

It should be noted that the biomarkers demonstrate patient-to-patient variations, and that these differences are not directly correlated, but may be inversely correlated.

Example 22

Comparison of Patients with Ovarian Cancer for DNA Repair Biomarker Profiles In this study, all patients had stage 3 or 4 ovarian or primary peritoneal carcinoma, and were treated with surgery followed by platinum-based chemotherapy. The ovarian cancer patients were evaluated using a group of DNA repair biomarkers as noted in FIG. 39A-F. The four biomarkers (A=FANCD2, B=MLH1, C=XPF, D=PT334 MAPKAPKINASE2, E=Ki67) are shown with 6 patients. In each subsection of FIGS. 41A-41E, the same patient is in the same position in the figure and the patients are anonymously numbered (Patient 37, 38, 39, 4, 40, and 41). The marker, Ki67, is not a DNA repair marker, but instead is an indicator of cell proliferation capacity within the tumor zone. Note that the 6 patients possess roughly equivalent levels of cell proliferation in this example. Like the example with head and neck cancers, the ovarian cancers are evaluated by pathology-directed scoring to discriminate differences in Intensity and Quantity of the nuclear biomarkers. The DNA repair biomarkers show significant variations in the intensity of staining by IHC, indicating that these biomarkers may be relevant to patient stratification and/or responsiveness to therapies.

Example 23

Analysis of Patient Cohorts for DNA Repair and DNA Damage Signaling Biomarkers Pathology scoring is used to differentiate the trends in expression changes with each of the biomarkers. Four pathologists established a scoring system where the intensity (I) and quantity (Q) measurements were made from each tumor specimen. I scores ranged from values 1, 2, and 3 with increasing intensity where 1 is weak, 2 is moderate, and 3 is strong. Q scores were determined to be 1 (1-9%), 2 (10-39%), 3 (40-69%), OR 4(70-100%) based on the fraction of nuclei that were positive with the marker. A combined score of I×Q yields a scoring in the range of 1-12.

Figure 42:
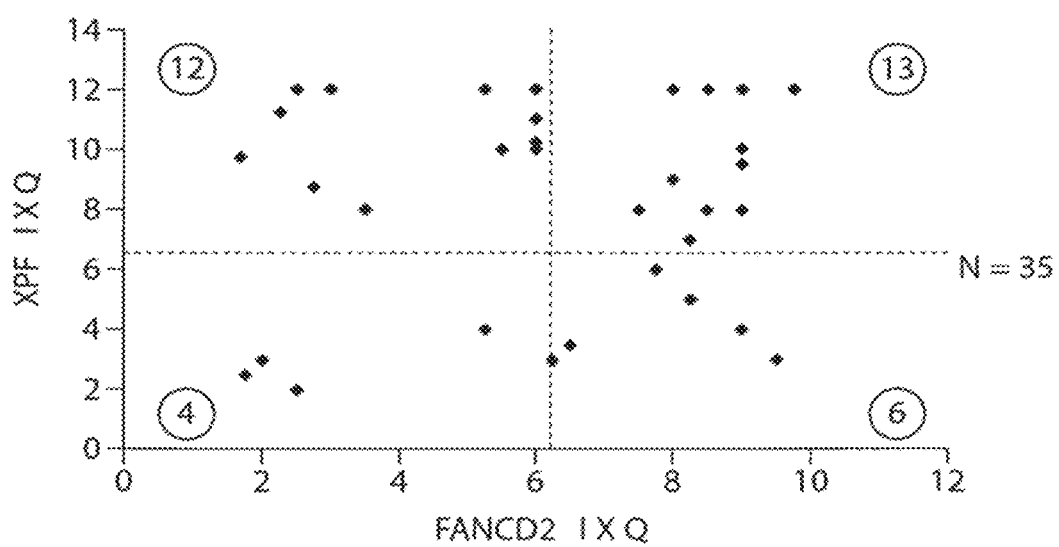
FIG. 42. Comparison of FANCD2 (FA/HR) and XPF (Nucleotide excision repair) biomarkers in head and neck cancers. Head and Neck cancer patients (N=35) were evaluated by IHC with FANCD2 and XPF biomarkers. The two markers are components of the Fanconi Anemia/Homologous Recombination and Nucleotide Excision Repair pathways respectively. Pathology scoring is expressed as I (Intensity)×Q (Quantity) on a scale of 1-12. Patients are divided into 4 quadrants based on biomarker scores of 6 or less versus >6 for each marker. Circled numbers represent the number of patients per quadrant.

Head and neck cancer specimens were evaluated by the above criteria and the scores for each patient per biomarker plotted against each other (FIG. 42). For XPF, 25/35 patients had higher range expression. Also, for FANCD2 biomarker 19/35 patients had higher expression levels. However, the same patients are not in the high expression group for both biomarkers most of the time. With the example of the FANCD2 and XPF markers, it is shown that approximately one-half of the patients have increased levels of one marker while having reduced levels of the other. It was observed that 13/35, or 37% of the patients had higher levels of both markers, whereas only 4/35, or 11% had reduced levels of both markers. Therefore, human cancer patients are able to be subgrouped or stratified based on the use of DNA repair and DNA damage biomarkers.

Example 24

Figure 43:
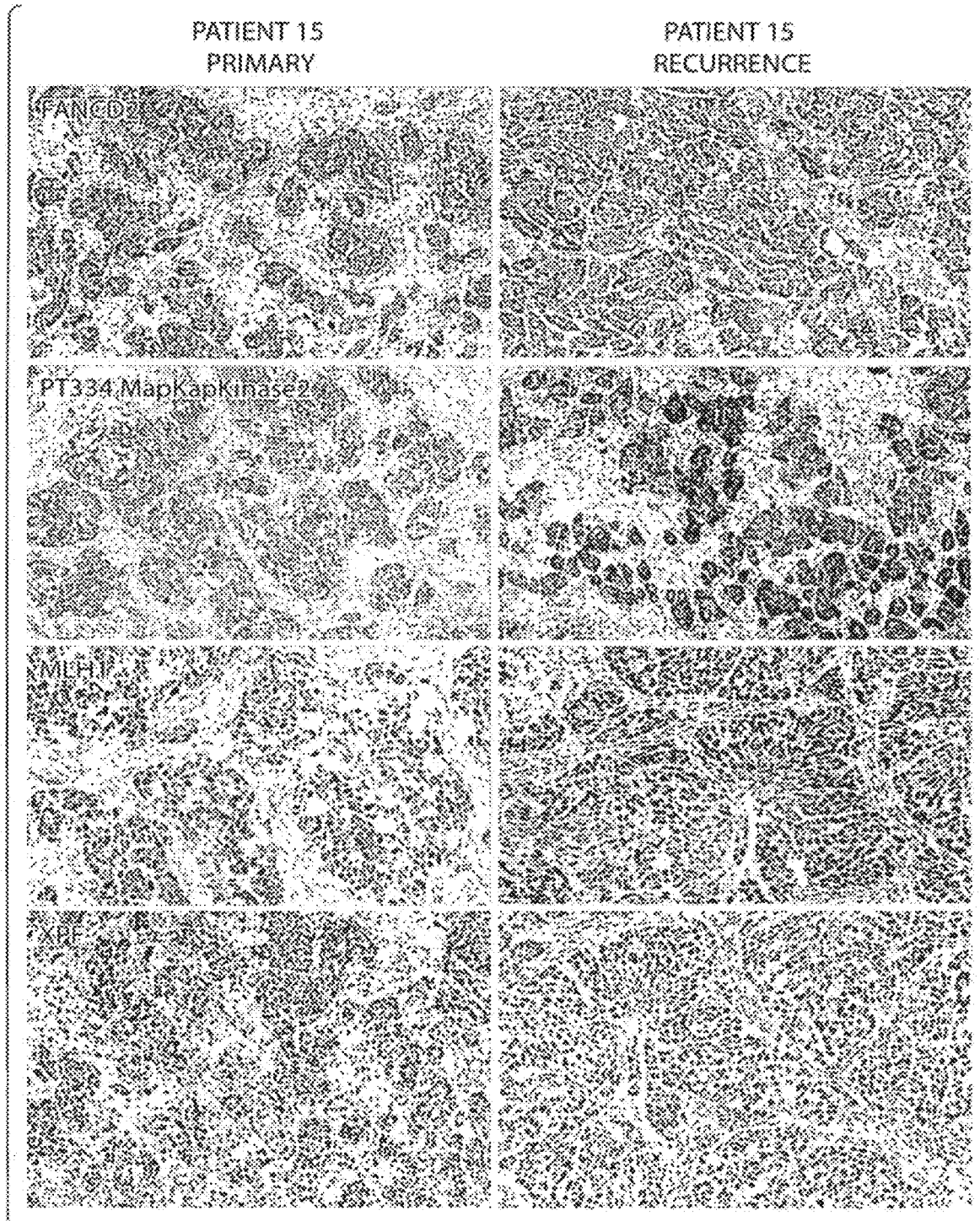
FIG. 43. DNA Repair biomarker evaluation of an Ovarian cancer patient tumor specimen after surgical resection compared with biopsy following recurrence. Image analysis was conducted over the same region of interest for the Patient15 and Patient15R (recurrence) specimens. The DNA repair and DNA damage signaling biomarkers are as noted in the insert to the photographs, listed are FANCD2, PT334 MapkapKinase2, MLH1, and XPF. The image data indicates a trend of increased expression of the FANCD2 and PT334 MapkapKinase2 levels upon recurrence, relatively little change for the MLH1 biomarker, and slightly reduced levels for the XPF biomarker.

Evaluation of Association Between Primary and Recurrence Status Using DNA Repair and DNA Damage Signaling Biomarkers Tumor specimens from a patient with ovarian cancer were evaluated in the primary biopsy (surgical resection of the tumor) and in follow-up when the ovarian cancer had a recurrence following chemotherapy with cisplatin. The patient had an ovarian serous carcinoma, FIGO grade 3, FIGO stage 3c. Four biomarkers of DNA repair and DNA damage signaling were co-investigated: FANCD2, MLH1, XPF, and PT334 MAPKAPKinase2. In FIG. 43, images from the four markers are assembled in tandem. It was observed that several of the biomarkers changed in the IHC expression pattern, and they were observed to vary to differing levels depending on the marker. Therefore, several of the DNA repair biomarkers may be influential markers in determining the response to platin-based therapies.

It has been demonstrated that the Fanconi Anemia proteins are important determinants of cisplatin-sensitivity of cells (Chirnomas and DAndrea, 2006). The identification of a biomarker such as FANCD2 that increases in intensity in ovarian cancer specimen that is from a recurrence is indicative of an association between increased FANCD2 and platin-resistance during therapy. Likewise, the observation that PT334 Mapkapkinase2 biomarker, which is indicative of hyperactivation of the Mapkapkinase2 enzyme and signaling pathway, would be a second indicator of the adaptive response to platin-based therapies in human cancers.

Example 25

General Methods

Cell Culture

HeLa cells, U2OS cells, GM6914 (FA-A), PD326 (FA-G), PD426 (FA-C), PD20 (FA-D2), and EUFA423 (FA-D1) were grown in DMEM supplemented with 15% heat-inactivated fetal calf serum (FCS) in a humidified 5% $CO_2$ incubator at 37° C. DF1179 (FA-E) fibroblasts derived from another FA-E patient were cultured in Chang medium (Irivine Scientific) (generously provided by Akiko Shimamura, Children's Hospital, Harvard Medical School, Boston, Mass.). Epstein-Barr virus EBV-transformed lymphoblasts EUFA130 (FA-E) were maintained in RPMI 1640 with 15% FCS.

Generation of DNA Damage

Cells were UV irradiated with a Stratalinker (Stratagene) at 50%-70% confluency without any medium after washing with PBS once in 100 mm dish without the lid. After UV irradiation, the fresh medium was added and cells were continuously cultured for the indicated time before lysis. Gamma irradiation was delivered using a Gammacell 40 apparatus (MDS Nordion). For MMC (Sigma) treatment, cells were continuously exposed to the drug for the indicated time before lysis. MMC sensitivity assays of human fibroblasts, and lymphoblasts was performed essentially as described with modifications as below (5, 7). Human fibroblasts and lymphoblasts were seeded in duplicate in 96-well microplates at a density of 1000 cells/well in appropriate medium. MMC was added at a final concentration of 0-200 µM. Cells were then incubated at 37° C. in 5% $CO_2$ incubator for 5 days, and cell survival was then determined by staining nucleic acids with a proprietary dye (CyQUANT; Molecular Probes) and subsequently analyzed by a Fluorescence microplate reader according to manufacturer's protocol.

Plasmids and Purification of Recombinant Proteins

Human FANCE cDNA (generously provided by J. deWinter and H. Joenje, Free University Medical Center, Amsterdam, The Netherlands) was subcloned into the retroviral vector pMMP-puro by adding the FLAG tag at the amino terminus of FANCE to generate pMMP-puro-FLAG- FANCE. Specific single, double mutations (pMMP-FLAG-T346A, pMMP-FLAG-S374A, pMMP-FLAG-T346A/S374A (TS/AA)) were introduced by using the QuikChange mutagenesis kit (Stratagene) according to the manufacturer's protocol. For construction of pGEX-FANCE (332-365), pGEX-FANCE (349-382) and pGEX-FANCE (332-382), PCR products of corresponding fragments were ligated to the EcoRI/NotI sites of the plasmid pGEX4T-1 (Pharmacia). The cDNAs of T346A, S374A and the double mutant of FANCE (T346A/S374A-TS/AA) were produced with the QuikChange mutagenesis kit (Stratagene). Recombinant FANCE (149-536) wild-type (rFANCEwt) construct was cloned to the EcoRI/Hind III sites of pET32a-PPS vector (Novagen). For recombinant double mutant FANCE (rTS/AA), the fragment of 149-536 with T346A and S374A was produced by PCR using pMMP-FLAG-TS/AA as a template, the product was cloned to the EcoRI/Hind III sites of pET32a-PPS vector. All constructs and mutants were confirmed by DNA sequencing.

GST-FANCE constructs spanning FANCE sequence (332-382) were expressed in *E. coli* BL21 cells. A GST-Cdc25C (200-256) construct (generously provided by Michael Yaffe, Massachusetts Institute of Technology, Boston, Mass.) was used as a positive control for in vitro kinase assay. The GST fusion proteins were then purified on glutathione S-Sepharose beads and used as substrates in the in vitro kinase reaction. Recombinant FANCE wild-type (rFANCEwt) and double mutants (rTS/AA) were expressed and induced in *E. coli* BL21(DE3)RP cells and then were purified by metal affinity chromatography using polyhistidine (His) binding HiTrap chelating HP columns (Pharmacia). After recombinant proteins were eluted from the column by incubation with precision protease to cleave its N-terminal His-tag sequence, further purification by HiTrapQFF anion exchange columns (Pharmacia) and S-200 gel filtration columns were performed.

Retroviral Infection

Production of pMMP retroviral supernatants and infection of fibroblasts or lymphoblasts were performed as previously described.

Generation of Anti-FANCE, Anti-FANCE-Phosphothreonine-T346, Anti-FANCE-Phosphoserine-S374 Antibodies A rabbit polyclonal antibody against FANCE was generated by Invitrogen (Zymed) using a C-terminal peptide 521-536 of FANCE as an antigen source. For generation of phosphospecific antibodies (anti-pT346-FANCE and anti-pS374-FANCE), rabbits were immunized with a KLH (Keyhole limpet hemocyanin)-conjugated FANCE phosphopeptide (SDLGLLRLC (pT) WL) (SEQ ID NO: 1), or phosphopeptide (LFLGRIL(pS)LTSS) (SEQ ID NO: 2) derived from amino acids 337-348 or 367-378 of FANCE, respectively. Antibodies were affinity purified using the corresponding phosphorylated and nonphosphorylated peptide-conjugated gels.

Immunoblotting

Cells were lysed, and whole cell extracts were subjected to SDS-PAGE, transferred to nitrocellulose membranes, and subjected to Western blot analysis (5). The following antibodies were used: anti-FANCD2 (FI-17) (Santa Cruz Biotech.), anti-HA (HA.11, Babcock), anti-FLAG (M2) (Sigma), anti-β-Tubulin (Santa Cruz Biotech.), anti-ATR (N-19) (Santa Cruz Biotech.), anti-phopsho-317-Chk1 (Cell Signaling technology), anti-Chk1(G-4) (Santa Cruz Biotech.).

In Vitro Kinase Assay

The GST-fusion proteins of FANCE (2 μg) were incubated with purified recombinant Chk1 (100 ng) (Upstate Technology) in 30 μl of kinase buffer (20 mM Tris HCL, 10 mM MgCl$_2$, 10 mM MnCl$_2$, 1 mm DTT, 10 μM ATP) containing 10 μCi of [γ$^{32}$P]-ATP. Kinase reactions were incubated for 30 min at 30° C., stopped by addition of SDS sample buffer, and boiled for 5 min, then analyzed by SDS-PAGE and X-ray film autoradiography. In vitro kinase assays were performed using GST-Cdc25C (200-256) and GST for positive and negative controls. Assay conditions were the same as described above. Recombinant FANCE proteins (rFANCEwt and rTS/AA) (3 μg) were incubated without or with 100 ng of purified recombinant Chk1, Chk2, MAPKAP K2 (MK2) (Upstate Technology) or GST in 30 μl of kinase buffer (20 mM Tris HCL, 10 mM MgCl$_2$, 10 mM MnCl$_2$, 1 mm DTT, 1 mM ATP) for 30 min at 30° C., the kinase reaction was stopped by addition of SDS sample buffer, and boiled for 5 min, then analyzed by SDS-PAGE, followed by Western blot with anti-pT346-FANCE, anti-pS374-FANCE antibodies.

Immunoprecipitation

Immunoprecipitation was performed as previously described.

SiRNA and Transfection

Expression of targeted genes was knocked down by transient expression of siRNA directed against GFP (5'-AACACTTGTCACTACTTTCTC-3') (SEQ ID NO: 3), Chk1 (5'-AAGAAGCAGTCGCAGTGAAGA-3') (SEQ ID NO: 4), ATR (5'-CAGGCACTAATTGTTCTTCAA-3') (SEQ ID NO: 5). Transfection of siRNAs was performed using Hiperfect (Qiagen) according to the manufacturer's protocol. At 72 hr of transfection, cells were treated with DNA damage.

Immunofluorescence Microscopy

Preparation of cells for immunofluorescence microscopy was performed as described. Lymphoblasts cell lines were grown on culture slide coated with poly-D-lysine (BD Bioscience) to promote adhesion for 36 hours before treatment. Images were acquired using a Axioplan 2 imaging microscope (Carl Zeiss) equipped with a digital camera and processed using Openlab software.

FACS Analysis

G2/M checkpoint analysis and DNA replication were performed as described previously (30). To detect of sub G1 population, cells were harvested at 0, 24, 48 and 72 hr after MMC (160 ng/ml) treatment, washed with PBS, fixed in 70% ethanol (10$^6$ cells per ml) for at least 1 hour at 4° C. and permeabilized in 0.25% Triton X-100/PBS at 4° C. for 15 min. Following washing with PBS, cells were resuspended in PBS containing 25/ml μg of propidium iodide (PI) (Sigma) and 0.1 mg/ml of RNase A (Sigma) prior to FACS analysis using a Becton Dickinson FACSCalibur flow cytometer. Cell death was measured as the sub G1 (less than 2N DNA content) population.

Mutation Analysis

The mutations were analyzed by RT-PCR amplification of total RNA purified from DF1179 cells (FA-E) and U2OS cells (control) using the specific primer pairs, then cDNA of both cell lines were analyzed by DNA sequencing using different primers spanning from exon 1 to exon 10 of FANCE.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating cancer in a human subject, comprising:
   a) determining whether a cell of said cancer is deficient in FANCA, FANCD2, FANCE, or FANCG as compared to a wild type control; and
   b) when said cell is deficient in FANCA, FANCD2, FANCE, or FANCG, administering to said subject an ATM inhibitor, wherein said subject is not administered a PARP inhibitor.

2. The method of claim 1, further comprising step c), wherein step c) comprises administering a chemotherapeutic agent or radiation therapy to said human subject.

3. The method of claim 2, wherein said chemotherapeutic agent is selected from the group consisting of a crosslinking agent, a strand break agent, an alkylating agent, an antimetabolite agent, a microtubule disruptor, a radiomimetic agent, a radiosensitizer, an intercalator, a DNA replication inhibitor, an anthracycline, an etoposide, and a topoisomerase II inhibitor.

4. The method of claim 1, wherein said cell is deficient in FANCA.

5. The method of claim 1, wherein said cell is deficient in FANCD2.

6. The method of claim 1, wherein said cell is deficient in FANCE.

7. The method of claim 1, wherein said cell is deficient in FANCG.

8. The method of claim 1, further comprising step c), wherein step c) comprises administering a Chk1 inhibitor to said human subject.

9. The method of claim 1, further comprising step c), wherein step c) comprises administering an Mlh1 inhibitor to said human subject.

10. The method of claim 1, further comprising step c), wherein step c) comprises administering a Chk1 inhibitor and an Mlh1 inhibitor to said human subject.

11. The method of claim 1, wherein said cancer is head and neck squamous cell carcinoma, prostate cancer, non-small cell lung cancer, ovarian cancer, or peritoneal carcinoma.

12. The method of claim 1, further comprising administering a chemotherapeutic agent or radiation therapy and a Chk1 inhibitor and/or an Mlh1 inhibitor to said human subject.

13. The method of claim 1, wherein said cancer is ovarian cancer, head and neck cancer, or non-small cell lung cancer (NSCLC).

* * * * *

SEQUENCE LISTING

```
<160> NUMBER OF SEQ ID NOS: 15

<210> SEQ ID NO 1
<211> LENGTH: 12
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: Phosphorylated

<400> SEQUENCE: 1

Ser Asp Leu Gly Leu Leu Arg Leu Cys Thr Trp Leu
1               5                   10

<210> SEQ ID NO 2
<211> LENGTH: 12
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Phosphorylated

<400> SEQUENCE: 2

Leu Phe Leu Gly Arg Ile Leu Ser Leu Thr Ser Ser
1               5                   10

<210> SEQ ID NO 3
<211> LENGTH: 21
<212> TYPE: DNA
<213> ORGANISM: Homo sapiens

<400> SEQUENCE: 3
aacacttgtc actactttct c                                              21

<210> SEQ ID NO 4
<211> LENGTH: 21
<212> TYPE: DNA
<213> ORGANISM: Homo sapiens

<400> SEQUENCE: 4
aagaagcagt cgcagtgaag a                                              21

<210> SEQ ID NO 5
<211> LENGTH: 21
<212> TYPE: DNA
<213> ORGANISM: Homo sapiens

<400> SEQUENCE: 5
caggcactaa ttgttcttca a                                              21

<210> SEQ ID NO 6
<211> LENGTH: 9
<212> TYPE: PRT
<213> ORGANISM: Homo sapiens

<400> SEQUENCE: 6

Leu Gly Leu Leu Arg Leu Cys Thr Trp
1               5

<210> SEQ ID NO 7
<211> LENGTH: 9
<212> TYPE: PRT
<213> ORGANISM: Homo sapiens
```

```
<400> SEQUENCE: 7

Leu Phe Leu Gly Arg Ile Leu Ser Leu
1               5

<210> SEQ ID NO 8
<211> LENGTH: 60
<212> TYPE: PRT
<213> ORGANISM: Homo sapiens

<400> SEQUENCE: 8

Leu Cys Ala Gln Leu Gln Leu Pro Gln Leu Ser Asp Leu Gly Leu Leu
1               5                   10                  15

Arg Leu Cys Thr Trp Leu Leu Ala Leu Ser Pro Asp Leu Ser Leu Ser
            20                  25                  30

Asn Ala Thr Val Leu Thr Arg Ser Leu Phe Leu Gly Arg Ile Leu Ser
        35                  40                  45

Leu Thr Ser Ser Ala Ser Arg Leu Leu Thr Thr Ala
    50                  55                  60

<210> SEQ ID NO 9
<211> LENGTH: 60
<212> TYPE: PRT
<213> ORGANISM: Mouse

<400> SEQUENCE: 9

Leu Cys Ser Glu Leu Gln Leu Pro Gln Leu Pro Asp Gly Gly Leu Leu
1               5                   10                  15

Gln Leu Cys Ser His Leu Met Gly Leu Thr Pro Ala Leu Ser Leu Ser
            20                  25                  30

Asn Ala Ser Val Leu Ala Arg Ser Leu Phe Leu Asp Arg Ile Arg Ser
        35                  40                  45

Leu Pro Ser Ser Ala Ser Arg Leu Leu Arg Val Ala
    50                  55                  60

<210> SEQ ID NO 10
<211> LENGTH: 60
<212> TYPE: PRT
<213> ORGANISM: Rat

<400> SEQUENCE: 10

Leu Cys Ser Gln Leu Gln Leu Pro Gln Leu Pro Asp Gly Gly Leu Leu
1               5                   10                  15

Gln Leu Cys Ser His Leu Leu Gly Leu Thr Pro Ala Leu Ser Ile Ser
            20                  25                  30

Asn Ala Ser Val Leu Ala Arg Ser Leu Phe Leu Asp Arg Ile Leu Ser
        35                  40                  45

Leu Pro Ser Ser Ala Ser Arg Leu Leu Arg Ala Ala
    50                  55                  60

<210> SEQ ID NO 11
<211> LENGTH: 60
<212> TYPE: PRT
<213> ORGANISM: Dog

<400> SEQUENCE: 11

Leu Cys Ala Gln Leu Gln Leu Pro Gln Leu Ser Asp Pro Ala Leu Leu
1               5                   10                  15

Gln Leu Cys Thr Trp Leu Leu Ser Leu Ser Pro Asp Leu Ser Leu Ser
            20                  25                  30
```

```
Asn Ala Thr Val Leu Thr Lys Ser Leu Phe Leu Arg Arg Ile Leu Ser
            35                  40                  45

Leu Thr Ser Ser Ala Ser Arg Leu Leu Met Thr Ala
        50                  55                  60

<210> SEQ ID NO 12
<211> LENGTH: 60
<212> TYPE: PRT
<213> ORGANISM: Cattle

<400> SEQUENCE: 12

Leu Cys Ala Gln Leu Gln Leu Pro Gln Leu Leu Asp Thr Gly Leu Leu
1               5                   10                  15

Gln Leu Cys Thr Trp Leu Leu Ala Leu Ser Pro Asp Leu Ser Leu Gly
            20                  25                  30

Asn Ala Thr Val Leu Thr Arg Ser Leu Phe Leu Gly Arg Ile Val Ser
            35                  40                  45

Leu Thr Ser Ser Ala Ser Arg Leu Leu Thr Thr Ala
        50                  55                  60

<210> SEQ ID NO 13
<211> LENGTH: 60
<212> TYPE: PRT
<213> ORGANISM: Chicken

<400> SEQUENCE: 13

Leu Cys Ser Phe Leu Gln Leu Ser Thr Cys Pro Glu Gln Leu Leu Gly
1               5                   10                  15

Arg Phe Cys Ser Trp Leu Leu Ala Leu Thr Pro Asp Leu Ser Tyr Thr
            20                  25                  30

Ser Ala Ala Val Leu Ala Glu Gln Leu Phe Leu Thr Arg Val Leu Ser
            35                  40                  45

Leu Ser Gln Pro Pro Ser Arg His Leu Met Ala Ala
        50                  55                  60

<210> SEQ ID NO 14
<211> LENGTH: 60
<212> TYPE: PRT
<213> ORGANISM: Pufferfish

<400> SEQUENCE: 14

Leu Cys Asn Met Leu Cys Leu Ser Asp Leu Pro Glu Gln Thr Leu Pro
1               5                   10                  15

Lys Leu Cys Ser Thr Ile Leu Ala Pro Ser Asn Asp Leu Ser Tyr Ile
            20                  25                  30

Thr Ala Thr Lys Phe Ile Lys Ser Leu Leu Lys Lys Val Leu Ser
            35                  40                  45

Leu Ser Glu Pro Ala Ser Arg Ser Leu Val Thr Ala
        50                  55                  60

<210> SEQ ID NO 15
<211> LENGTH: 60
<212> TYPE: PRT
<213> ORGANISM: Zebrafish

<400> SEQUENCE: 15

Leu Cys Asn Met Leu Cys Leu Ser Asp Leu Pro Glu Gln Thr Leu Pro
1               5                   10                  15

Lys Leu Cys Ser Thr Ile Leu Ala Pro Ser Asn Asp Leu Ser Tyr Ile
            20                  25                  30
```

```
Thr Ala Thr Lys Pro Ile Lys Ser Leu Leu Leu Lys Lys Val Leu Ser
        35                  40                  45

Leu Ser Glu Pro Ala Ser Arg Ser Leu Val Thr Ala
        50                  55                  60
```